(12) United States Patent
Griffioen et al.

(10) Patent No.: US 9,284,271 B2
(45) Date of Patent: Mar. 15, 2016

(54) COMPOUNDS FOR THE TREATMENT OF NEURODEGENERATIVE DISEASES

(75) Inventors: Gerard Griffioen, Linden (BE); Tom Van Dooren, Lier (BE); Verónica Rojas De La Parra, Haasrode (BE); Arnaud Marchand, Korbeek/Lo (BE); Sara Alassia, Mechelen (BE); Amuri Kilonda, Roosbeek-Boutersem (BE); Patrick Chaltin, Jodoigne (BE)

(73) Assignees: Katholieke Universiteit Leuven, K.U. Leuven R&D, Leuven (BE); reMYND, Heverlee (BE)

( * ) Notice: Subject to any disclaimer, the term of this patent is extended or adjusted under 35 U.S.C. 154(b) by 0 days.

(21) Appl. No.: 13/993,756

(22) PCT Filed: Dec. 13, 2011

(86) PCT No.: PCT/EP2011/072565
§ 371 (c)(1),
(2), (4) Date: Jun. 13, 2013

(87) PCT Pub. No.: WO2012/080220
PCT Pub. Date: Jun. 21, 2012

(65) Prior Publication Data
US 2013/0289033 A1 Oct. 31, 2013

(30) Foreign Application Priority Data
Dec. 13, 2010 (GB) .................... 1021104.3

(51) Int. Cl.
| | | |
|---|---|---|
| *C07D 209/14* | (2006.01) | |
| *C07D 209/18* | (2006.01) | |
| *C07D 401/12* | (2006.01) | |
| *C07D 409/12* | (2006.01) | |
| *C07D 471/04* | (2006.01) | |

(52) U.S. Cl.
CPC ............ *C07D 209/18* (2013.01); *C07D 209/14* (2013.01); *C07D 401/12* (2013.01); *C07D 409/12* (2013.01); *C07D 471/04* (2013.01)

(58) Field of Classification Search
CPC .. C07D 471/04; C07D 401/12; C07D 409/12; C07D 209/18; C07D 209/14
See application file for complete search history.

(56) References Cited

U.S. PATENT DOCUMENTS

| | | |
|---|---|---|
| 6,306,890 B1 | 10/2001 | Kalgutkar et al. |
| 2004/0058963 A1 | 3/2004 | Yamamoto et al. |
| 2005/0075356 A1 | 4/2005 | Di Francesco et al. |
| 2007/0021428 A1 | 1/2007 | Matthews |
| 2007/0083045 A1 | 4/2007 | Di Francesco et al. |
| 2008/0045527 A1 | 2/2008 | Matthews |
| 2009/0054235 A1 | 2/2009 | Mansfield et al. |
| 2009/0105308 A1 | 4/2009 | Mansfield et al. |
| 2009/0312334 A1 | 12/2009 | Matthews |
| 2012/0053165 A1 | 3/2012 | Allen et al. |
| 2012/0070395 A1 | 3/2012 | Amino et al. |

FOREIGN PATENT DOCUMENTS

| | | |
|---|---|---|
| CN | 1365971 A | 8/2002 |
| WO | 0115686 A1 | 3/2001 |
| WO | 0183471 A1 | 11/2001 |
| WO | 03035076 A1 | 5/2003 |
| WO | 03051877 A1 | 6/2003 |
| WO | 2004081011 A1 | 9/2004 |

(Continued)

OTHER PUBLICATIONS

Buchmann, et al. Document No. 150:55993, retrieved from STN; Dec. 18, 2008.*
Chaudhuri, et al. Document No. 150:237295, retrieved from STN; Feb. 19, 2009.*
Miller, et al. Document No. 134:311205, retrieved from STN; Apr. 20, 2001.*
Springer, et al. Document No. 126:74521, retrieved from STN; Dec. 18, 1996.*
Koppitz, et al. Document No. 152:238770, retrieved from STN; Feb. 4, 2010.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http:llwww.cnn.com12003lHEALTHlconditionslO91241alzheimers.drug.aplindexhtml>.*
PCT International Search Report, PCT/EP2011/072565, dated Apr. 24, 2012.
PCT International Preliminary Report on Patentability, PCT/EP2011/072565 dated Jun. 27, 2013.

(Continued)

*Primary Examiner* — Shawquia Jackson
(74) *Attorney, Agent, or Firm* — TraskBritt, P.C.

(57) ABSTRACT

This invention provides novel compounds and the novel compounds for use as a medicine, more in particular for the prevention or treatment of neurodegenerative disorders, more specifically certain neurological disorders, such as disorders collectively known as tauopathies, and disorders characterized by cytotoxic α-synuclein amyloidogenesis. The present invention also relates to the use of said novel compounds for the manufacture of medicaments useful for treating such neurodegenerative disorders. The present invention further relates to pharmaceutical compositions including said novel compounds and to methods for the preparation of said novel compounds. The compounds have the formula (A1), wherein $R^1$, $R^2$, $R^4$, $R^5$, $R^6$, E, n, $Y^1$, $Y^2$, $Y^3$, $Y^4$, $Y^5$, B, $R^8$, and m are as defined in the claims.

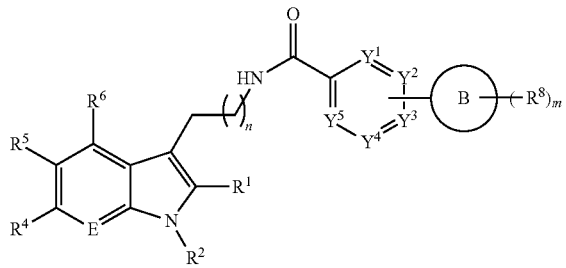

(A1)

13 Claims, 1 Drawing Sheet

(56) References Cited

FOREIGN PATENT DOCUMENTS

| WO | 2006007542 A1 | 1/2006 |
|---|---|---|
| WO | 2006067224 A2 | 6/2006 |
| WO | 2007006734 A1 | 1/2007 |
| WO | 2007006739 A1 | 1/2007 |
| WO | 2010012396 A1 | 2/2010 |
| WO | 2010100606 A1 | 9/2010 |
| WO | 2010110353 A1 | 9/2010 |
| WO | 2012080220 A1 | 6/2012 |
| WO | 2012080221 A1 | 6/2012 |

OTHER PUBLICATIONS

Augustinack et al., Specific Tau Phosphorylation Sites Correlate With Severity of Neuronal Cytopathology in Alzheimer's Disease, Acta Neuropathol, 2002, pp. 26-35, vol. 103.

Gerard et al., The aggregation of Alpha-Synuclein is Stimulated by FK506 Binding Proteins as Shown by Fluorescence Correlation Spectroscopy, the FASEB Journal, Mar. 2006, pp. 524-526, vol. 20.

Celik et al., Binding of Serotonin to the Human Serotonin Transporter. Molecular Modeling and Experimental Validation, J. Am. Chem. Soc., 2008, pp. 3853-3865, vol. 130.

Enzensperger et al., Dopamine/Serotonin Receptor Ligands. 13: Homologization of a Benzindoloazecine-Type Dopamine Receptor Antagonist Modulates the Affinities for Dopamine D1-D5 Receptors, J. Med. Chem., 2006, pp. 6408-6411, vol. 49.

Heredia-Moya et al., Syntheses of 7-fluoro- and 6,7-difluoroserotonin and 7-fluoro- and 6,7-difluoromelatonin, Journal of Fluorine Chemistry, 2006, pp. 1256-1260, vol. 127, Elsevier.

Terwel et al., Protein Synthesis, Post-Translation Modification, and Degradation: Changed Conformation of Mutant Tau-P301L Underlies the Moribund Tauopathy, Absent in Progressive, Nonlethal Axonopathy of Tau-4R/2N Transgenic Mice, The Journal of Biological Chemistry, 2005, pp. 3963-3973, vol. 280.

Mewshaw et al., Studies toward the Discovery of the Next Generation of Antidepressants. 3. Dual 5-HT1A and Serotonin Transporter Affinity within a Class of N-Aryloxyethylindolylalkylamines, J. Med. Chem., 2004, pp. 3823-3842, vol. 47.

Zhang et al., Retarded Axonal Transport of R406W Mutant Tau in Transgenic Mice with a Neurodegenerative Tauopathy, The Journal of Neuroscience, May 12, 2004, pp. 4657-4667, vol. 24, No. 19.

Vercammen et al., Parkin Protects against Neurotoxicity in the 6-Hydroxydopamine Rat Model for Parkinson's Disease, Molecular Therapy, Nov. 2006, pp. 716-723, vol. 16, No. 5.

Bertrand et al., The Pattern of Human Tau Phosphorylation is the Result of Priming and Feedback Events in Primary Hippocampal Neurons, Neuroscience, 2010, pp. 323-334, vol. 168.

Finaru et al., Microwave-Assisted Solid-Phase Synthesis of 5-Carboxamido-N-acetyltryptamine Derivatives, Organic Letters, 2002, pp. 2613-2615, vol. 4, No. 16.

Bennasar et al., Sequential N-Acylamide Methylenation-Enamide Ring-Closing Metathesis: Construction of Benzo-Fused Nitrogen Heterocycles, J. Org. Chem., 2006, pp. 7028-7034, vol. 71.

Finaru et al., Microwave-Assisted Synthesis of 5-carboxymethoxy-N-acetylryptamine Derivatives, Tetrahedron Letters, 2002, pp. 787-790, vol. 43.

* cited by examiner

COMPOUNDS FOR THE TREATMENT OF NEURODEGENERATIVE DISEASES

CROSS-REFERENCE TO RELATED APPLICATIONS

This application is a national phase entry under 35 U.S.C. §371 of International Patent Application PCT/EP2011/072568, filed Dec. 13, 2011, designating the United States of America and published in English as International Patent Publication WO 2012/080221 A1 on Jun. 21, 2012, which claims the benefit under Article 8 of the Patent Cooperation Treaty and under 35 U.S.C. §119(e) to Great Britain Patent Application Serial No. 1021103.5, filed Dec. 13, 2010.

FIELD OF THE INVENTION

The present invention relates to novel compounds and to the novel compounds for use as a medicine, more in particular for the prevention or treatment of neurodegenerative disorders, more specifically certain neurological disorders, such as disorders collectively known as tauopathies, and disorders characterised by cytotoxic α-synuclein amyloidogenesis. The present invention also relates to the compounds for use as a medicaments and to the use of said compounds for the manufacture of medicaments useful for treating such neurodegenerative disorders. The present invention further relates to pharmaceutical compositions including said novel compounds and to methods for the preparation of said novel compounds.

BACKGROUND OF THE INVENTION

TAU is an intracellular protein with the ability to bind and consequently stabilise and define microtubule structure and function. Apart from this physiological function TAU also plays a direct role in numerous neurodegenerative disorders collectively known as "tauopathies" with the most notable examples being Alzheimer's disease, Pick's disease, corticobasal degeneration, progressive supranuclear palsy, frontotemporal dementia and parkinsonism linked to chromosome 17 (FTDP-17).

Tauopathies are characterised by insoluble aggregates or polymers of tau which are formed by self-polymerisation of tau monomers. The precise molecular mechanisms involved in TAU aggregation is not clearly known but may involve partial denaturation or misfolding of the TAU protein in conformations with a high propensity to self-organise into higher order structures. An important aspect of the TAU aggregation is its inherent cytotoxicity, which reduces cellular integrity or even triggers cell death. In case of neurodegenerative diseases, loss of affected neurons leads to cognitive and/or motor dysfunctioning. A direct role of TAU in disease onset has been established unequivocally by the elucidation of familial mutations in TAU which appear to be responsible for a very early and sometimes aggressive form of tauopathy. Such mutations comprise changes in the amino acid sequence of TAU that promote toxic aggregation and thereby provoke loss of cellular integrity.

Treatments aimed to suppress cytotoxic TAU pathology are presently not available. Currently used treatments for Alzheimer's disease offer a small symptomatic benefit, but no treatments to delay or halt the progression of the disease are available.

α-Synuclein is a neuronal protein which originally has been associated with neuronal plasticity during Zebra finch song learning. Although its role at the molecular level is at present largely elusive it appears to have lipid bi-layer (or membrane) with binding properties important for preserving proper transport of neurotransmitter vesicles to the axonal ends of neurons presumably to ensure proper signalling at the synapse. Apart from its physiological role in brain cells, human α-synuclein also possesses pathological features that underlie a plethora of neurodegenerative diseases including Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, multiple system atrophy and Alzheimer's disease. These neurological disorders are characterised by the presence of insoluble α-synuclein polymers or aggregates usually residing within neuronal cells, although in the case of Alzheimer's disease α-synuclein (or proteolytic fragments thereof) constitutes the non-amyloid component of extracellular "amyloid-β plaques". It is widely believed that the amyloidogenic properties α-synuclein disrupt cellular integrity leading to dysfunctioning or death of affected neurons resulting in cognitive and/or motoric decline as it is found in patients suffering from such diseases. The aggregation of α-synuclein is at present very poorly defined, but constitutes most likely a multi-step process wherein self-polymerization of α-synuclein into insoluble aggregates is preceded by the formation of soluble protofibrils of α-synuclein monomers. Self-association may be triggered by the formation of alternative conformations of α-synuclein monomers with high propensity to polymerize. Several studies using neuronal cell lines or whole animals have shown that formation of reactive oxygen species (hereinafter abbreviated as ROS) appear to stimulate noxious α-synuclein amyloidogenesis. For instance paraquat (an agent stimulating ROS formation within the cell) has been recognized as a stimulator of α-synuclein aggregation. Like in animals, exposure to paraquat is believed to induce the formation of synuclein inclusions, and consequently neurodegeneration, especially of dopaminergic neurons in humans. Dopaminergic neurons appear to be particularly sensitive because the concurrent dopamine metabolism may on the one hand contribute significantly to the oxidative stress load but may on the other hand result in kinetic stabilisation of highly toxic protofibrillar α-synuclein species by dopamine (or its metabolic derivatives). Parkinson's disease is characterised by a selective loss of dopaminergic substantia nigra cells and therefore treatment of animals (or neuronal cells) with paraquat is a common well-accepted experimental set-up for studying synucleopathies, in particular Parkinson's disease.

Apart from ROS, mutations in the coding region of the α-synuclein gene have also been identified as stimulators of self-polymerization resulting in early disease onset as it is observed in families afflicted by such mutations. Finally, increased expression of α-synuclein also promotes early disease onset as evidenced by a duplication or triplication of the α-synuclein gene in the genome of some individuals. The molecular mechanism by which α-synuclein self-association triggers cellular degeneration is at present largely unknown. Although it has been speculated that insoluble aggregates affect cellular integrity, it has recently been suggested that soluble protofibrillar intermediates of the aggregation process are particularly toxic for the cell as opposed to mature insoluble fibrils which may be inert end-products or may even serve as cytoprotective reservoirs of otherwise harmful soluble species. Therapeutic attempts to inhibit formation of insoluble aggregates may therefore be conceptually wrong, possibly even promoting disease progress.

While the identification of pathological α-synuclein mutations unequivocally revealed a causative factor of a plethora of neurodegenerative disorders, treatments ensuring suppression of toxic α-synuclein amyloidogenesis are presently not available. Only symptomatic treatments of Parkinson's disease exist. These treatments aim e.g. at increasing dopamine levels in order to replenish its lowered level due to degeneration of dopaminergic neurons, for instance by administrating L-DOPA or inhibitors of dopamine breakdown. Although such treatments suppress disease symptoms to some extent, they are only temporarily effective and certainly do not slow down ongoing neuronal degeneration.

Thus there is a stringent need for new drugs for therapeutic and/or preventive applications that target the underlying molecular mechanism of TAU and/or α-synuclein related pathologies such as Alzheimer's disease in order to reduce neuronal cell death and/or degeneration, or at least retard the onset of the most disabilitating manifestations thereof. Therefore a goal of the present invention is to satisfy this urgent need by identifying efficient pharmaceutically active ingredients that are active against TAU and/or α-synuclein related pathologies such as Alzheimer's disease, less toxic and/or more stable (i.e. chemically stable, metabolically stable) and that can be useful, either alone or in combination with other active ingredients, for the treatment of TAU and/or α-synuclein related pathologies such as Alzheimer's disease in animals and more specifically in humans.

It is also known to the skilled in the art that the physicochemical properties of known drugs as well as their ADME-Tox (administration, distribution, metabolism, excretion) properties may limit or prohibit their use in the treatment of diseases. Therefore, a problem of existing drugs that can be overcome with the compounds of the invention can be selected from poor or inadequate physicochemical or ADME-Tox properties such as toxicity, solubility, LogP, CYP inhibition, hepatic stability, plasmatic stability, among others.

SUMMARY OF THE INVENTION

The present invention is based on the unexpected finding that at least one of the above-mentioned problems can be solved by a novel class of compounds. The present invention provides compounds which are useful for preventing or treating neurodegenerative disorders, especially tauopathies. The present invention demonstrates that these compounds efficiently inhibit the tau-aggregation induced toxicity which is responsible for neurodegeneration. Therefore, these novel compounds constitute a useful class of compounds that can be used in the treatment and/or prevention of neurodegenerative disorders in animals, more specifically in humans.

A first aspect of the present invention therefore provides compounds according to formula (AA1),

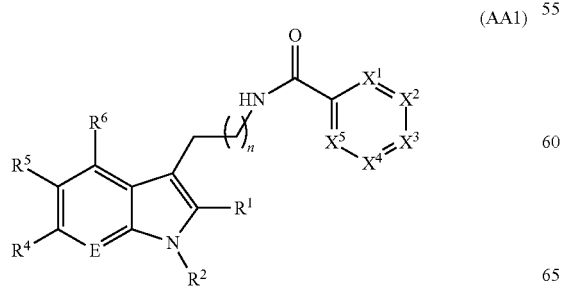

(AA1)

wherein,

E is independently selected from $CR^3$; and N;

each $R^1$, $R^3$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

$R^2$ is selected from hydrogen; alkyl; alkenyl; and alkynyl;

$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

n is selected from 0; 1; 2;
one of $X^1$, $X^2$, $X^3$, $X^4$ and $X^5$ is selected from CW; whereby W is

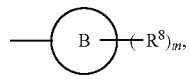

while each of the other of $X^1$, $X^2$, $X^3$, $X^4$ and $X^5$ is independently selected from $CZ^1$; N; $NR^{101}$; and CO; wherein maximally three of $X^1$, $X^2$, $X^3$, $X^4$ and $X^5$ are independently selected from N; $NR^{101}$; and CO; preferably one of $X^1$, $X^2$, $X^3$, $X^4$ and $X^5$ is selected from CW; whereby W is

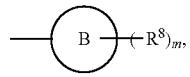

while each of the other of $X^1$, $X^2$, $X^3$, $X^4$ and $X^5$ is independently selected from $CZ^1$; N; and $NR^{101}$; wherein maximally three of $X^1$, $X^2$, $X^3$, $X^4$ and $X^5$ are independently selected from N; and $NR^{101}$;

B represents a cyclic structure selected from cycloalkyl; cycloalkenyl; cycloalkynyl; aryl; and heterocycle;

m is selected from 0; 1; 2; 3; 4 and 5;

$R^8$ is independently selected from hydrogen; halogen; alkyl; alkenyl; alkynyl; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{10}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

and wherein said alkyl, alkenyl and alkynyl optionally includes one or more heteroatoms, said heteroatoms being selected from the atoms O, S and N;

and wherein said alkyl, alkenyl and alkynyl can be unsubstituted or substituted with one or more $Z^2$;

and wherein a carbon atom or heteroatom of said alkyl, alkenyl and alkynyl, can be oxidized to form a C=O, C=S, N=O, N=S, S=O or $S(O)_2$;

each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;

each $Z^1$ is independently selected from hydrogen; alkyl; and $Z^2$;

each $Z^2$ is independently selected from halogen; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{20}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;

and wherein $R^{12}$ and $R^{13}$ can be taken together in order to form a (4-, 5-, 6-, or 7-membered) heterocycle which can be unsubstituted or substituted;

each $R^{20}$ is independently selected from alkyl; alkenyl; and alkynyl;

and wherein said alkyl, alkenyl, alkynyl optionally include one or more heteroatoms in the alkyl, alkenyl or alkynyl moiety, said heteroatom selected from O, S and N;

and wherein a carbon atom or heteroatom of said alkyl, alkenyl, alkynyl can be oxidized to form a C=O, C=S, N=O, N=S, S=O or $S(O)_2$;

each $R^{21}$ is independently selected from hydroxyl; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or $S(O)_2$;

each $R^{22}$ and $R^{23}$ is independently selected from hydrogen; alkyl; alkenyl; and alkynyl;
and wherein said alkyl, alkenyl or alkynyl optionally include one or more heteroatoms in the alkyl, alkenyl or alkynyl moiety, said heteroatom selected from O, S and N;
and wherein a carbon atom or heteroatom of said alkyl, alkenyl or alkynyl can be oxidized to form a C=O, C=S, N=O, N=S, S=O or $S(O)_2$;
and wherein $R^{22}$ and $R^{23}$ can be taken together in order to form a (4-, 5-, 6-, or 7-membered) non-aromatic heterocycle which can be unsubstituted or substituted;

and isomers (in particular stereoisomers, enantiomers or tautomers), solvates, hydrates, salts (in particular pharmaceutically acceptable salts) or prodrugs thereof.

In analogy, the first aspect of the present invention therefore provides compounds according to formula (A1),

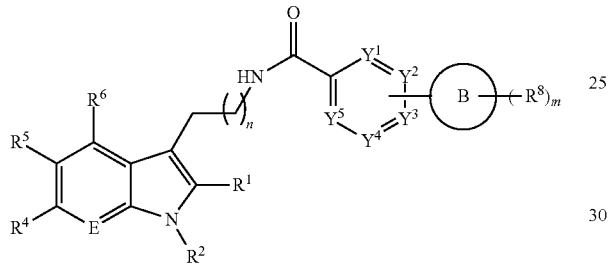

(A1)

wherein,
E is independently selected from $CR^3$; and N;
each $R^1$, $R^3$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
$R^2$ is selected from hydrogen; alkyl; alkenyl; and alkynyl;
$R^5$ is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene, optionally includes one or more heteroatoms in the alkyl(ene), alkenyl(ene) or alkynyl(ene) moiety, said heteroatoms being selected from the atoms O, S and N;
and wherein said alkyl, alkenyl, alkynyl, aryl, heterocycle, arylalkylene, arylalkenylene, arylalkynylene, heterocycle-alkylene, heterocycle-alkenylene or heterocycle-alkynylene can be unsubstituted or substituted with one or more Z;
and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or $S(O)_2$;
n is selected from 0; 1; and 2;
each of $Y^1$, $Y^2$, $Y^3$, $Y^4$ and $Y^5$ is independently selected from $CZ^1$; N; $NR^{101}$; and CO; wherein at least two of $Y^1$, $Y^2$, $Y^3$, $Y^4$ and $Y^5$ are selected from $CZ^1$; preferably each of $Y^1$, $Y^2$, $Y^3$, $Y^4$ and $Y^5$ is independently selected from $CZ^1$; N; and $NR^{101}$; wherein at least two of $Y^1$, $Y^2$, $Y^3$, $Y^4$ and $Y^5$ are selected from $CZ^1$;
B represents a cyclic structure selected from cycloalkyl; cycloalkenyl; cycloalkynyl; aryl; and heterocycle;
m is selected from 0; 1; 2; 3; 4 and 5;
each $R^8$ is independently selected from hydrogen; halogen; alkyl; alkenyl; alkynyl; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{10}S(O)_2R^{20}$; —$NR^{20}C(O)NR^{22}R^{23}$; —$NR^{22}R^{23}$; -cyano; —COOH; —$COOR^{20}$; —$C(O)NR^{22}R^{23}$; and —$C(O)R^{21}$;
and wherein said alkyl, alkenyl and alkynyl optionally includes one or more heteroatoms, said heteroatoms being selected from the atoms O, S and N;
and wherein said alkyl, alkenyl and alkynyl can be unsubstituted or substituted with one or more $Z^2$;
and wherein a carbon atom or heteroatom of said alkyl, alkenyl and alkynyl, can be oxidized to form a C=O, C=S, N=O, N=S, S=O or $S(O)_2$;
each Z is independently selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; and —$C(O)R^{11}$;
each $Z^1$ is independently selected from hydrogen; alkyl; and $Z^2$;
each $Z^2$ is independently selected from halogen; —OH; —$OR^{20}$; —SH; —$SR^{20}$; —$S(O)R^{21}$; —$S(O)_2R^{21}$; —$SO_2NR^{22}R^{23}$; trifluoromethyl; trifluoromethoxy; nitro; —$NHC(O)R^{20}$; —$NHS(O)_2R^{20}$; —$NHC(O)NR^{22}R^{23}$; —$NR^{20}C(O)R^{20}$; —$NR^{20}S(O)_2R^{20}$;

—NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each R$^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{101}$ is independently selected from hydrogen and R$^{10}$;

each R$^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

each R$^{12}$ and R$^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein said alkyl, alkenyl, alkynyl, aryl, heterocycle, arylalkylene, arylalkenylene, arylalkynylene, heterocycle-alkylene, heterocycle-alkenylene or heterocycle-alkynylene optionally include one or more heteroatoms in the alkyl(ene), alkenyl(ene) or alkynyl(ene) moiety, said heteroatom selected from O, S and N;

and wherein a carbon atom or heteroatom of said alkyl, alkenyl, alkynyl, aryl, heterocycle, arylalkylene, arylalkenylene, arylalkynylene, heterocycle-alkylene, heterocycle-alkenylene or heterocycle-alkynylene, can be oxidized to form a C=O, C=S, N=O, N=S, S=O or S(O)$_2$;

and wherein R$^{12}$ and R$^{13}$ can be taken together in order to form a (4-, 5-, 6-, or 7-membered) heterocycle which can be unsubstituted or substituted;

each R$^{20}$ is independently selected from alkyl; alkenyl; and alkynyl;

and wherein said alkyl, alkenyl, alkynyl optionally include one or more heteroatoms in the alkyl, alkenyl or alkynyl moiety, said heteroatom selected from O, S and N;

and wherein a carbon atom or heteroatom of said alkyl, alkenyl, alkynyl can be oxidized to form a C=O, C=S, N=O, N=S, S=O or S(O)$_2$;

each R$^{21}$ is independently selected from hydroxyl; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

each R$^{22}$ and R$^{23}$ is independently selected from hydrogen; alkyl; alkenyl; and alkynyl;

and wherein said alkyl, alkenyl or alkynyl optionally include one or more heteroatoms in the alkyl, alkenyl or alkynyl moiety, said heteroatom selected from O, S and N;

and wherein a carbon atom or heteroatom of said alkyl, alkenyl or alkynyl can be oxidized to form a C=O, C=S, N=O, N=S, S=O or S(O)$_2$;

and wherein R$^{22}$ and R$^{23}$ can be taken together in order to form a (4-, 5-, 6-, or 7-membered) non-aromatic heterocycle which can be unsubstituted or substituted;

and isomers (in particular stereoisomers, enantiomers or tautomers), solvates, hydrates, salts (in particular pharmaceutically acceptable salts) or prodrugs thereof.

According to an embodiment, the present invention provides compounds of Formula (A1) or (AA1), wherein one of X$^1$, X$^2$, X$^3$, X$^4$ and X$^5$ is selected from CW; whereby W is $$-\!\!\left(\!\!B\!\!\right)\!\!-\!\!(R^8)_m,$$

while each of the other of X$^1$, X$^2$, X$^3$, X$^4$ and X$^5$ is independently selected from CZ$^1$; N; and NR$^{101}$; wherein maximally three of X$^1$, X$^2$, X$^3$, X$^4$ and X$^5$ are independently selected from N; and NR$^{101}$;

E is independently selected from CR$^3$; and N;

each R$^1$, R$^3$, R$^4$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

R$^2$ is selected from hydrogen; alkyl; alkenyl; and alkynyl;

R$^5$ is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

n is selected from 0; 1; and 2;

each of Y$^1$, Y$^2$, Y$^3$, Y$^4$ and Y$^5$ is independently selected from CZ$^1$; N; NR$^{101}$; and CO; wherein at least two of Y$^1$, Y$^2$, Y$^3$, Y$^4$ and Y$^5$ are selected from CZ$^1$;

B represents a cyclic structure selected from cycloalkyl; cycloalkenyl; cycloalkynyl; aryl; and heterocycle;

m is selected from 0; 1; 2; 3; 4 and 5;

each $R^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{10}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; and —C(O)R$^{11}$;

each $Z^1$ is independently selected from hydrogen; alkyl; and $Z^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein $R^{12}$ and $R^{13}$ can be taken together in order to form a (4-, 5-, 6-, or 7-membered) heterocycle which can be unsubstituted or substituted;

each $R^{20}$ is independently selected from alkyl; alkenyl; and alkynyl;

each $R^{21}$ is independently selected from hydroxyl; alkyl; alkenyl; and alkynyl;

each $R^{22}$ and $R^{23}$ is independently selected from hydrogen; alkyl; alkenyl; and alkynyl;

and wherein $R^{22}$ and $R^{23}$ can be taken together in order to form a (4-, 5-, 6-, or 7-membered) non-aromatic heterocycle which can be unsubstituted or substituted.

According to an embodiment, the present invention provides compounds of Formula (A1) or (AA1), wherein one of $X^1$, $X^2$, $X^3$, $X^4$ and $X^5$ is selected from CW; whereby W is

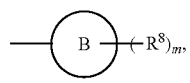

while each of the other of $X^1$, $X^2$, $X^3$, $X^4$ and $X^5$ is independently selected from CZ$^1$; N; and NR$^{101}$; wherein maximally three of $X^1$, $X^2$, $X^3$, $X^4$ and $X^5$ are independently selected from N; and NR$^{101}$;

E is independently selected from CR$^3$; and N;

each $R^1$, $R^3$, $R^4$ and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

$R^2$ is selected from hydrogen; alkyl; alkenyl; and alkynyl;

$R^5$ is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

n is selected from 0; 1; and 2;

each of $Y^1$, $Y^2$, $Y^3$, $Y^4$ and $Y^5$ is independently selected from CZ$^1$; N; NR$^{101}$; and CO; wherein at least two of $Y^1$, $Y^2$, $Y^3$, $Y^4$ and $Y^5$ are selected from CZ$^1$;

B represents a cyclic structure selected from cycloalkyl; cycloalkenyl; cycloalkynyl; aryl; and heterocycle;

m is selected from 0; 1; 2; 3; 4 and 5;

each $R^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{10}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; and —C(O)R$^{11}$;

each $Z^1$ is independently selected from hydrogen; alkyl; and $Z^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

and wherein $R^{12}$ and $R^{13}$ can be taken together in order to form a (4-, 5-, 6-, or 7-membered) heterocycle which can be unsubstituted or substituted;

each $R^{20}$ is independently selected from alkyl; alkenyl; and alkynyl;

each $R^{21}$ is independently selected from hydroxyl; alkyl; alkenyl; and alkynyl;

each $R^{22}$ and $R^{23}$ is independently selected from hydrogen; alkyl; alkenyl; and alkynyl;

and wherein $R^{22}$ and $R^{23}$ can be taken together in order to form a (4-, 5-, 6-, or 7-membered) non-aromatic heterocycle which can be unsubstituted or substituted.

According to an embodiment, the present invention provides compounds of Formula (A1) or (AA1), wherein one of $X^1$, $X^2$, $X^3$, $X^4$ and $X^5$ is selected from CW; whereby W is

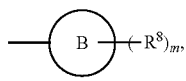

while each of the other of $X^1$, $X^2$, $X^3$, $X^4$ and $X^5$ is independently selected from $CZ^1$; N; and $NR^{101}$; wherein maximally three of $X^1$, $X^2$, $X^3$, $X^4$ and $X^5$ are independently selected from N; and $NR^{101}$; Preferably one of $X^1$, $X^2$, $X^3$, $X^4$ and $X^5$ is selected from CW; whereby W is

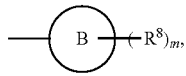

while each of the other of $X^1$, $X^2$, $X^3$, $X^4$ and $X^5$ is independently selected from $CZ^1$; and N; wherein maximally three of $X^1$, $X^2$, $X^3$, $X^4$ and $X^5$ are independently selected from N; and $NR^{101}$;

E is selected from $CR^3$; and N; preferably E is $CR^3$, each $R^1$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably each $R^1$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{1-6}$alkenylene; heterocycle-$C_{2-6}$alkenylene; and heterocycle-$C_{2-6}$alkynylene; preferably each $R^1$, $R^4$ and $R^6$ is independently selected from hydrogen; halogen; —OH; —$OC_{1-4}$alkyl; trifluoromethyl; trifluoromethoxy; -cyano; $C_{1-4}$alkyl; $C_6$aryl; $C_6$aryl$C_{1-6}$alkylene; heterocycle-$C_{1-6}$alkylene; preferably each $R^1$, $R^4$ and $R^6$ is independently selected from hydrogen; halogen; —OH; methoxy; trifluoromethyl; trifluoromethoxy; -cyano; $C_{1-4}$alkyl; $C_6$aryl; preferably each $R^1$, $R^4$ and $R^6$ is independently selected from hydrogen; halogen; —OH; trifluoromethyl; $C_{1-2}$alkyl; preferably each $R^1$, $R^4$ and $R^6$ is independently selected from hydrogen; fluoro; or chloro; preferably each $R^1$, $R^4$ and $R^6$ is independently hydrogen;

$R^3$ is selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably $R^3$ is selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably $R^3$ is selected from hydrogen; halogen; —OH; —$OR^{10}$; —SH; trifluoromethyl; trifluoromethoxy; nitro; —$NR^{12}R^{13}$; -cyano; —COOH; —$COOR^{10}$; $C_{1-6}$alkyl; $C_{6-10}$aryl; heterocycle; $C_{6-10}$aryl$C_{1-6}$alkylene; heterocycle-$C_{1-6}$alkylene; preferably $R^3$ is selected from hydrogen; halogen; —OH; —$OC_{1-4}$alkyl; trifluoromethyl; trifluoromethoxy; -cyano; $C_{1-4}$alkyl; $C_6$aryl; $C_6$aryl$C_{1-6}$alkylene; preferably $R^3$ is selected from hydrogen; halogen; —OH; methoxy; trifluoromethyl; trifluoromethoxy; -cyano; $C_{1-4}$alkyl; $C_6$aryl; preferably $R^3$ is selected from hydrogen; halogen; —OH; trifluoromethyl; $C_{1-2}$alkyl; preferably $R^3$ is selected from hydrogen;

$R^2$ is selected from hydrogen; alkyl; alkenyl; and alkynyl; preferably $R^2$ is selected from hydrogen; $C_{1-6}$alkyl; $C_{2-6}$alkenyl; and $C_{2-6}$alkynyl; preferably $R^2$ is selected from hydrogen; or $C_{1-6}$alkyl; preferably $R^2$ is hydrogen;

$R^5$ is selected from halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene; preferably $R^5$ is selected from halogen; —OH; —$OR^{10}$; —SH; —$SR^{10}$; —$S(O)R^{11}$;

—S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; C$_{1-6}$alkyl; C$_{2-6}$alkenyl; C$_{2-6}$alkynyl; C$_{6-10}$aryl; heterocycle; C$_{6-10}$arylC$_{1-6}$alkylene; C$_{6-10}$arylC$_{2-6}$alkenylene; C$_{6-10}$arylC$_{2-6}$alkynylene; heterocycle-C$_{1-6}$alkylene; heterocycle-C$_{2-6}$alkenylene; and heterocycle-C$_{2-6}$alkynylene; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)C$_{1-6}$alkyl; C$_{1-6}$alkyl; C$_{6-10}$aryl; heterocycle; C$_{6-10}$arylC$_{1-6}$alkylene; preferably R$^5$ is selected from halogen; -cyano; —OH; —OR$^{10}$; —SH; —SR$^{10}$; trifluoromethyl; trifluoromethoxy; —C(O)C$_{1-4}$alkyl; —NR$^{12}$R$^{13}$; C$_{1-6}$alkyl; phenyl; morpholinyl; preferably R$^5$ is selected from chloro, fluoro; -cyano; —OH; —OR$^{10}$; —SH; —SR$^{10}$; trifluoromethyl; trifluoromethoxy; C$_{1-6}$alkyl; phenyl; morpholinyl; preferably R$^5$ is selected from chloro, fluoro; -cyano; —CO$_{1-4}$alkyl; trifluoromethyl; trifluoromethoxy; C$_{1-6}$alkyl; preferably R$^5$ is selected from chloro, fluoro, or methyl;

n is selected from 1; 0; and 2; preferably n is 1 or 0; preferably n is 1;

each of Y$^1$, Y$^2$, Y$^3$, Y$^4$ and Y$^5$ is independently selected from CZ$^1$; N; NR$^{101}$; and CO; wherein at least two of Y$^1$, Y$^2$, Y$^3$, Y$^4$ and Y$^5$ are selected from CZ$^1$; preferably each of Y$^1$, Y$^2$, Y$^3$, Y$^4$ and Y$^5$ is independently selected from CZ$^1$; or N; wherein at least two of Y$^1$, Y$^2$, Y$^3$, Y$^4$ and Y$^5$ are selected from CZ$^1$; preferably each of Y$^1$, Y$^2$, Y$^3$, Y$^4$ and Y$^5$ is independently selected from CZ$^1$; or N; wherein at least three of Y$^1$, Y$^2$, Y$^3$, Y$^4$ and Y$^5$ are selected from CZ$^1$; preferably with Z$^1$ being selected from hydrogen, alkyl or Z$^2$, and Z$^2$ is halogen;

B represents a cyclic structure selected from aryl; cycloalkyl; cycloalkenyl; cycloalkynyl; and heterocycle; preferably B is selected from aryl; cycloalkyl; and heterocycle; preferably B is selected from aryl; or heterocycle; preferably B is selected from C$_{6-10}$aryl; or heterocycle; B is selected from C$_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, pyrazinyl, oxazolyl, imidazolyl, pyrrolidinyl; preferably B is selected from phenyl, furanyl, or thienyl;

m is selected from 0; 1; 2; 3; 4 and 5; preferably m is 0, 1, 2 or 3; preferably m is 0, 1 or 2, preferably m is 0 or 1;

each R$^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each R$^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each R$^8$ is independently selected from hydrogen; halogen; alkyl; —OH; —OR$^{20}$; —SH; trifluoromethyl; trifluoromethoxy; nitro; -cyano; preferably each R$^8$ is independently selected from hydrogen; halogen; alkyl; —OR$^{20}$; trifluoromethyl; trifluoromethoxy; -cyano; wherein R$^{20}$ is alkyl; preferably each R$^8$ is independently selected from hydrogen; halogen; C$_{1-6}$alkyl; —OR$^{20}$; trifluoromethyl; trifluoromethoxy; -cyano; wherein R$^{20}$ is C$_{1-6}$alkyl; preferably each R$^8$ is independently selected from hydrogen; halogen; C$_{1-4}$alkyl; —OR$^{20}$; trifluoromethyl; -cyano; wherein R$^{20}$ is C$_{1-2}$alkyl; preferably each R$^8$ is independently selected from hydrogen; fluoro; chloro; C$_{1-2}$alkyl; —OCH$_3$; trifluoromethyl; -cyano;

each Z$^1$ is independently selected from hydrogen; alkyl; and Z$^2$; preferably each Z$^1$ is independently selected from hydrogen; C$_{1-6}$alkyl; and Z$^2$;

each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$; preferably each Z$^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NR$^{22}$R$^{23}$; -cyano; —COOH; —COOR$^{20}$; and —C(O)R$^{21}$; preferably each Z$^2$ is independently selected from halogen; —OH; —OR$^{20}$; —SH; trifluoromethyl; trifluoromethoxy; —NR$^{22}$R$^{23}$; -cyano; —COOH; —COOR$^{20}$; and —C(O)R$^{21}$; preferably each Z$^2$ is independently selected from halogen; —OH; —OC$_{1-6}$alkyl; trifluoromethyl; trifluoromethoxy; -cyano; preferably each Z$^2$ is independently selected from fluoro; chloro; —OH; —OC$_{1-3}$alkyl; trifluoromethyl; trifluoromethoxy; -cyano;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene; preferably each $R^{10}$ is independently selected from alkyl; aryl; heterocycle; arylalkylene; heterocycle-alkylene; preferably each $R^{10}$ is independently selected from $C_{1-6}$alkyl; $C_{6-10}$aryl; heterocycle; $C_{6-10}$aryl$C_{1-6}$alkylene; preferably each $R^{10}$ is independently $C_{1-6}$alkyl;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene; preferably each $R^{11}$ is independently selected from hydroxyl, alkyl; aryl; heterocycle; arylalkylene; heterocycle-alkylene; preferably each $R^{11}$ is independently selected from hydroxyl; $C_{1-6}$alkyl; $C_{6-10}$aryl; heterocycle; $C_{6-10}$aryl$C_{1-6}$alkylene; preferably each $R^{11}$ is independently from hydroxyl or $C_{1-6}$alkyl;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene; and wherein $R^{12}$ and $R^{13}$ can be taken together in order to form a (4-, 5-, 6-, or 7-membered) heterocycle which can be unsubstituted or substituted; preferably each $R^{12}$ and $R^{13}$ is independently selected from hydrogen; alkyl; aryl; heterocycle; arylalkylene; heterocycle-alkylene; and wherein $R^{12}$ and $R^{13}$ can be taken together in order to form a 4-, 5-, or 6-, membered heterocycle; preferably each $R^{12}$ and $R^{13}$ is independently selected from hydrogen; alkyl; aryl; heterocycle; arylalkylene; preferably each $R^{12}$ and $R^{13}$ is independently selected from hydrogen; $C_{1-6}$alkyl; $C_{6-10}$aryl; heterocycle;

each $R^{20}$ is independently selected from alkyl; alkenyl; and alkynyl; preferably each $R^{20}$ is independently selected from alkyl; preferably each $R^{20}$ is independently selected from $C_{1-6}$alkyl; preferably each $R^{20}$ is independently selected from $C_{1-4}$alkyl;

each $R^{21}$ is independently selected from hydroxyl; alkyl; alkenyl; and alkynyl; preferably each $R^{21}$ is independently selected from alkyl; preferably each $R^{21}$ is independently selected from $C_{1-6}$alkyl; preferably each $R^{21}$ is independently selected from $C_{1-4}$alkyl;

each $R^{22}$ and $R^{23}$ is independently selected from hydrogen; alkyl; alkenyl; and alkynyl; and wherein $R^{22}$ and $R^{23}$ can be taken together in order to form a (4-, 5-, 6-, or 7-membered) non-aromatic heterocycle which can be unsubstituted or substituted; preferably each $R^{22}$ and $R^{23}$ is independently selected from hydrogen; or alkyl; and wherein $R^{22}$ and $R^{23}$ can be taken together in order to form a 4-, 5-, or 6-, membered non-aromatic heterocycle; preferably each $R^{22}$ and $R^{23}$ is independently selected from hydrogen; or alkyl; preferably each $R^{22}$ and $R^{23}$ is independently selected from hydrogen; or $C_{1-6}$alkyl.

In another particular embodiment, $R^5$ is selected from halogen, methoxy, methyl, trifluoromethoxy, acetyl, phenyl, cyano and morpholinyl. In another particular embodiment, $R^5$ is selected from halogen.

In another particular embodiment, $R^5$ is selected from halogen, methoxy, methyl, trifluoromethoxy, trifluoromethyl, hydroxyl, acetyl, and cyano. In another particular embodiment, $R^5$ is selected from fluoro and chloro.

In a particular embodiment, E is $CR^3$.

In a particular embodiment, each $R^1$, $R^3$, $R^4$, and $R^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; and alkynyl. More in particular, each $R^1$, $R^3$, $R^4$, and $R^6$ is independently selected from hydrogen; halogen; —OH; —OR$^{10}$; —SH; —SR$^{10}$; trifluoromethyl; trifluoromethoxy; nitro; alkyl; alkenyl; and alkynyl. Yet more in particular embodiment, each of $R^1$, $R^3$, $R^4$ and $R^6$ is independently selected from hydrogen, halogen, —OH, methoxy, and methyl. In yet another particular embodiment, each of $R^1$, $R^3$, $R^4$ and $R^6$ is independently selected from hydrogen and halogen, more in particular each of $R^1$, $R^3$, $R^4$ and $R^6$ is hydrogen.

In another particular embodiment, $R^1$ is hydrogen or alkyl, more in particular is hydrogen. In another particular embodiment, $R^2$ is hydrogen or alkyl, yet more in particular is hydrogen. In another particular embodiment, $R^3$ is hydrogen. In another particular embodiment, $R^4$ is hydrogen or halogen. In another particular embodiment, $R^4$ is hydrogen. In another particular embodiment, $R^6$ is hydrogen. In another particular embodiment, $R^3$, $R^4$ and $R^6$ are hydrogen.

In another particular embodiment, $R^2$ is independently selected from hydrogen and methyl, yet more in particular is hydrogen.

In a particular embodiment, n is 1.

In a particular embodiment of the present invention and of all formulas herein, each of $Y^1$, $Y^2$, $Y^3$, $Y^4$ and $Y^5$ is independently selected from $CZ^1$; N; and NR$^{101}$. In another particular embodiment, each of $Y^1$, $Y^2$, $Y^3$, $Y^4$ and $Y^5$ is independently selected from $CZ^1$; N; and NR$^{101}$ and form a ring selected from phenyl, pyridyl, pyridazyl, pyrazinyl and pyrimidyl. In yet another particular embodiment, each of $Y^1$, $Y^2$, $Y^3$, $Y^4$ and $Y^5$ is $CZ^1$ and form a phenyl ring.

In a particular embodiment of the present invention and of all formulas herein, each of $Y^1$, $Y^2$, $Y^3$ is $CZ^1$ and each of $Y^4$ and $Y^5$ is N.

In a particular embodiment of the present invention and of all formulas herein, each of $Y^1$, $Y^2$, $Y^3$ and $Y^5$ is $CZ^1$ and each $Y^4$ is N.

In a particular embodiment of the present invention and of all formulas herein, each of $Y^1$, $Y^2$, $Y^4$ and $Y^5$ is $CZ^1$ and each $Y^3$ is N.

In a particular embodiment of the present invention and of all formulas herein, each $Z^1$ is hydrogen.

In a particular embodiment, B is selected from $C_{3-8}$cycloalkyl; $C_{5-8}$cycloalkenyl; $C_{6-10}$aryl; or heterocycle; more particularly B is selected from $C_{3-8}$cycloalkyl; $C_{6-10}$aryl; or pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; yet more particularly B is selected from $C_{3-6}$cycloalkyl; $C_{6-10}$aryl; or pyridyl, dihydroypyridyl, piperidyl, thiazolyl, tetrahydrothiophenyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; still more particularly B is selected from $C_{3-6}$cycloalkyl; phenyl, naphthyl, pyridyl, piperidyl, thiazolyl, furanyl, thienyl, pyrrolyl, pyrazolyl, imidazolyl, tetrazolyl, benzofuranyl, indolyl, indolenyl, quinolinyl, isoquinolinyl, benzimidazolyl, piperidinyl, 4-piperidonyl, pyrrolidinyl, 2-pyrrolidonyl, pyrrolinyl, triazinyl, pyranyl, isobenzofuranyl, 2H-pyrrolyl, isothiazolyl, isoxazolyl, pyrazinyl, pyridazinyl, indolizinyl, isoindolyl, 3H-indolyl, 1H-indazoly, purinyl, pyrimidinyl, furazanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl. In another particular embodiment, B is independently selected from aryl and heterocycle. Yet more in particular, B is selected from aryl and heteroaryl. Still more in particular, B is selected from phenyl, thienyl, furanyl or pyridyl. Yet more in particular, B is phenyl.

In another particular embodiment, $R^8$ is not selected from —NHC(O)$R^{10}$. In another particular embodiment, $R^8$ is selected from hydrogen; halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein said alkyl, alkenyl and alkynyl optionally includes one or more heteroatoms, said heteroatoms being selected from the atoms O, S and N; and wherein said alkyl, alkenyl and alkynyl can be unsubstituted or substituted with Z; and wherein a carbon atom or heteroatom of said alkyl, alkenyl and alkynyl, can be oxidized to form a C=S, N=O, N=S, S=O or S(O)$_2$.

In another particular embodiment, $R^8$ is selected from hydrogen; halogen; alkyl; alkenyl; alkynyl; —OH; —OR$^{10}$; —SH; —SR$^{10}$; trifluoromethyl; trifluoromethoxy; —NR$^{12}$R$^{13}$; -cyano. In another particular embodiment, $R^8$ is selected from hydrogen; halogen; linear alkyl; linear alkenyl; linear alkynyl; —OH; —OR$^{10}$; —SH; —SR$^{10}$; trifluoromethyl; trifluoromethoxy; —NR$^{12}$R$^{13}$; -cyano. In another particular embodiment, $R^8$ does not comprise a cyclic ring structure (for example selected from cyclic alkyl, cyclic alkenyl, cyclic alkynyl, aryl or heterocycle). In another particular embodiment, $R^8$ is independently selected from halogen, methyl, methoxy, cyano, and trifluoromethyl. In a particular embodiment, $R^8$ is halogen, yet more in particular is fluor. In a particular embodiment, each $R^8$ is independently selected from halogen; $C_{1-6}$alkyl; —OH; $C_{1-6}$alkoxy; $C_{1-6}$alkoxycarbonyl; trifluoromethyl; trifluoromethoxy; and cyano.

In another particular embodiment, m is selected from 0, 1 and 2.

In yet another particular embodiment, the compounds of the invention comprise maximally three monocyclic or cyclic fused ring systems selected from aryl or heterocycle. In yet another particular embodiment, the compounds of the invention comprise maximally three ring systems, whereby said three ring systems consist of:

the indole or azaindole ring;

the six-membered ring comprising $Y^1$, $Y^2$, $Y^3$, $Y^4$ and $Y^5$; and

B.

In a particular embodiment of the present invention, the compounds have a structure according to the formulas (A2), or (A3):

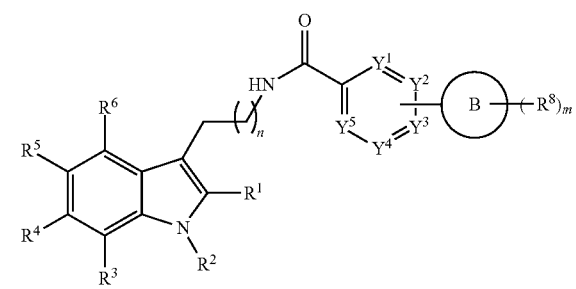

(A2)

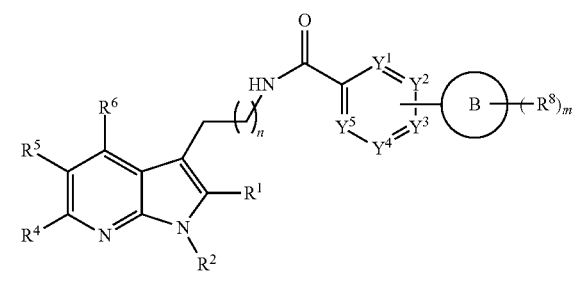

(A3)

wherein $R^1$, $R^2$, $R^3$, $R^4$, $R^5$, $R^6$, $R^8$, $Y^1$, $Y^2$, $Y^3$, $Y^4$, $Y^5$, B, m and n have the same meaning as that defined herein (for example in formula (A1) and the embodiments thereof).

In a more particular embodiment the present invention therefore provides compounds according to formula (B1), (B2) or (B3), (B1)
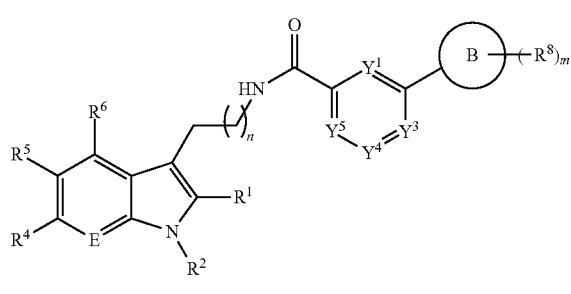

(C2)
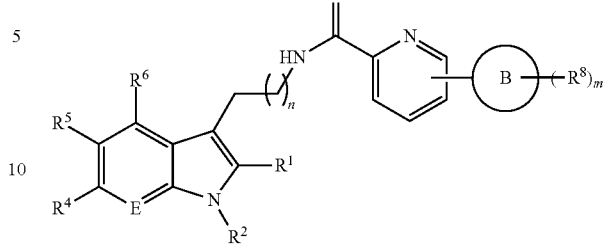

(B2)
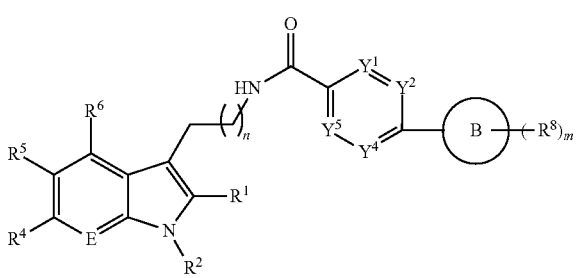

(C3)
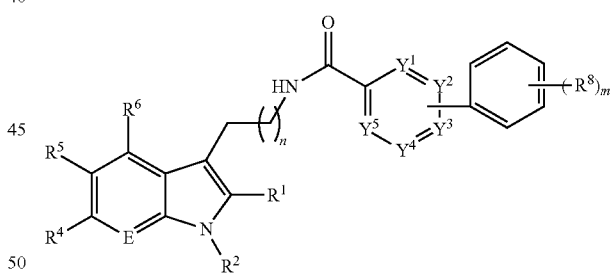

wherein E, $R^1$, $R^2$, $R^3$, $R^4$, $R^5$, $R^6$, $R^8$, B, m and n have the same meaning as that defined herein (for example in formula A1 and the embodiments thereof).

In yet another preferred embodiment, the compounds have a structure according to formula (F1), (F2), (F3), (F4) or (F5), (B3)
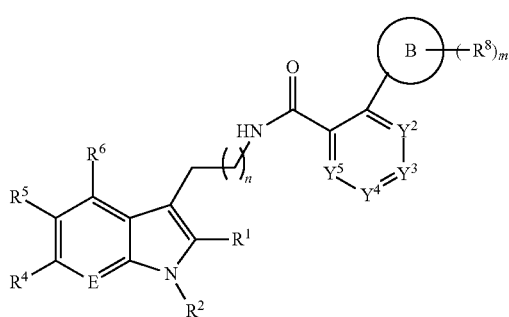

wherein E, $R^1$, $R^2$, $R^3$, $R^4$, $R^5$, $R^6$, $R^8$, $Y^1$, $Y^2$, $Y^3$, $Y^4$, $Y^5$, B, m and n have the same meaning as that defined herein (for example in formula A1 and the embodiments thereof).

In another preferred embodiment, the compounds have a structure according to formula (C1), (C2) or (C3);

(F1)
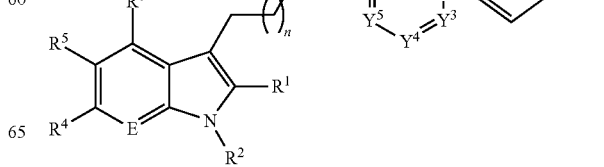

(C1)
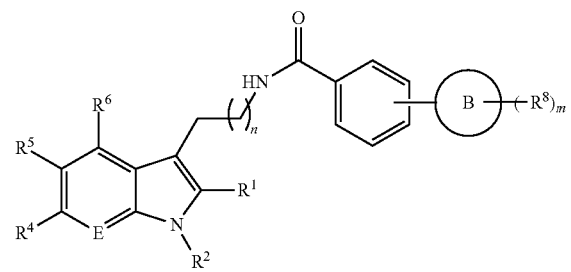

(F2)

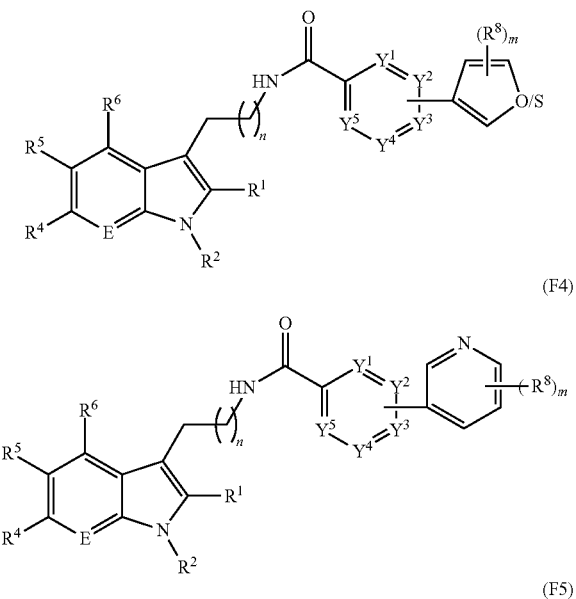

(F3)

(F4)

(F5)

wherein E, $R^1$, $R^2$, $R^3$, $R^4$, $R^5$, $R^6$, $R^8$, $Y^1$, $Y^2$, $Y^3$, $Y^4$, $Y^5$, m and n have the same meaning as that defined herein (for example in formula A1 and the embodiments thereof).

In a particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, wherein n is 1.

In another particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, whereby $R^2$ is H. In another particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, whereby $R^3$ is H.

In another particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, wherein B is aryl or heteroaryl (yet more in particular is phenyl, thienyl, furanyl or pyridyl) and $R^8$ is selected from hydrogen, halogen, —OH, cyano, $C_{1-6}$alkoxy, trifluoromethyl; trifluoromethoxy. In another particular embodiment of the present invention, the compounds have a structure according to the formulas herein, whereby $R^8$ is selected from hydrogen and halogen.

In a particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, wherein B is aryl and $R^8$ is selected from hydrogen, halogen, —OH, cyano, $C_{1-6}$alkoxy, trifluoromethyl; trifluoromethoxy.

In a particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, wherein B is aryl and $R^8$ is selected from hydrogen, halogen, cyano, $C_{1-6}$alkoxy, trifluoromethyl; trifluoromethoxy.

In another particular embodiment of the present invention, the compounds have a structure according to the formulas (AA1), (A1), (A2), (A3), (B1), (B2), (B3), (C1), (C2), (C3), (F1), (F2), (F3), (F4) or (F5) or any subgroup thereof, whereby the cycle B is phenyl.

In another particular embodiment of the present invention, the compounds have a structure according to the formulas herein, whereby $R^1$, $R^3$, $R^4$ and $R^6$ are hydrogen.

In another particular embodiment of the present invention, the compounds have a structure according to the formulas herein, wherein $R^1$, $R^2$, $R^3$, $R^4$ and $R^6$ are hydrogen.

A particular embodiment of the invention relates to compounds with a structure according to formula (G1), (G2), (G3), (G4), (G5), (G6), (G7), or (G8):

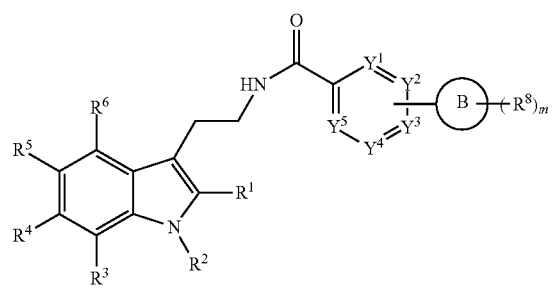

(G1)

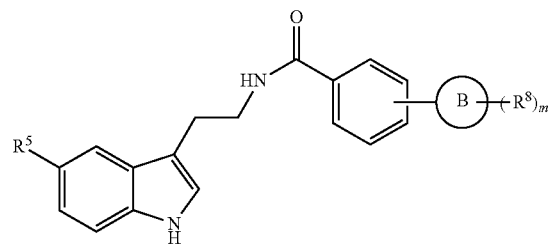

(G2)

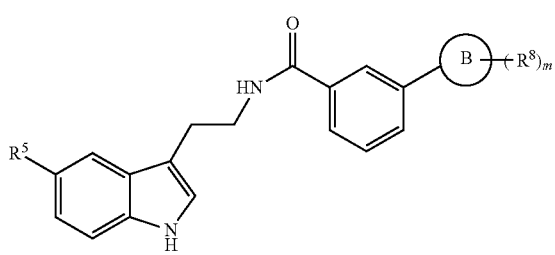

(G3)

(G4)
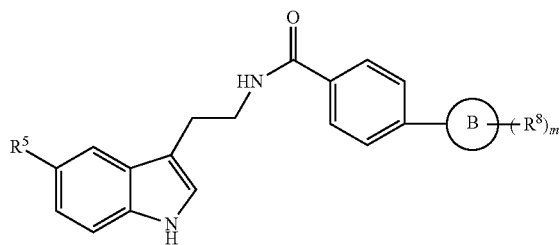
(G5)
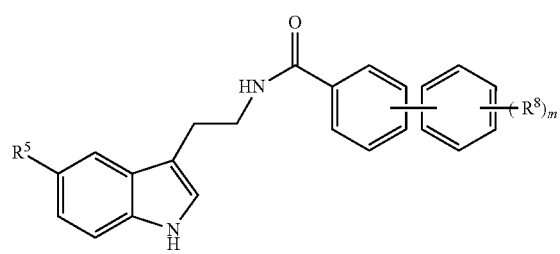
(G6)
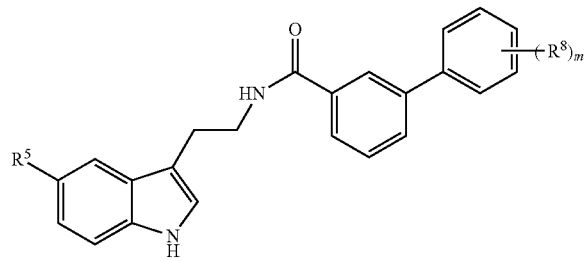
(G7)
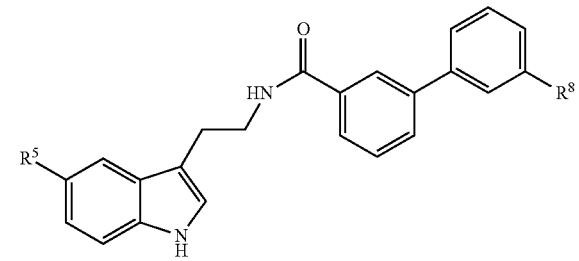
(G8)
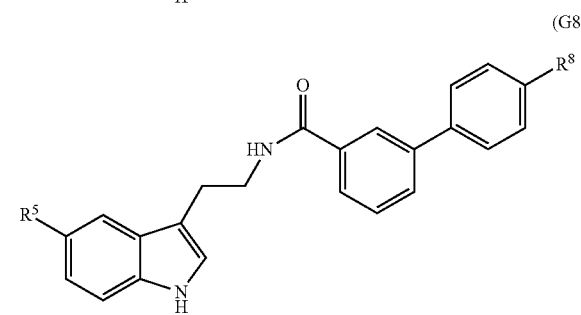
whereby all the remaining variables are as in formula (A1) or other formula or all embodiments described herein.
Another particular embodiment of the invention relates to compounds with a structure according to formula (H1), (H2), (H3) or (H4)
(H1)
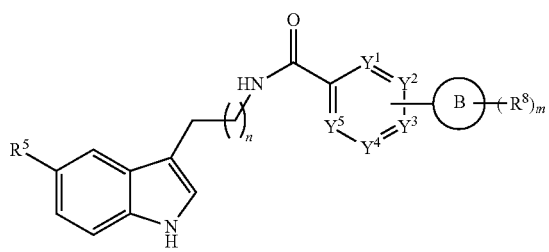
(H2)
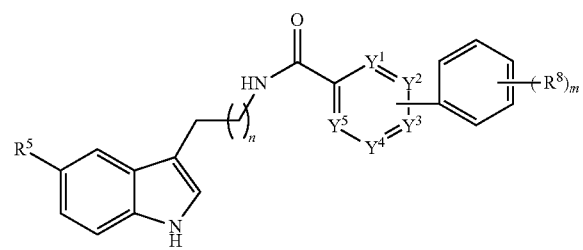
(H3)
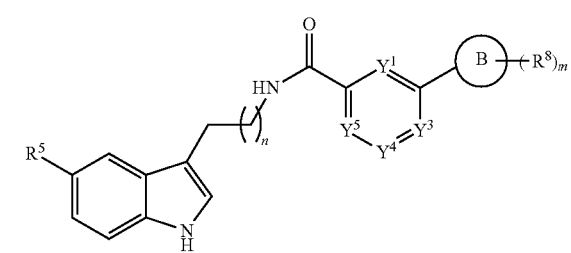
(H4)
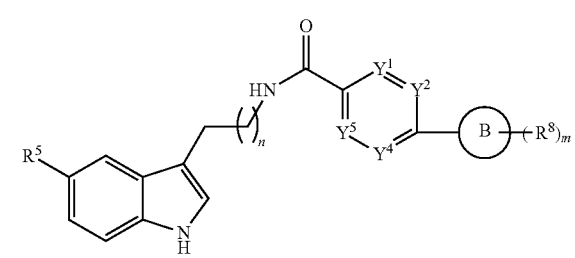
whereby all the remaining variables are as in formula (A1) or other formula or all embodiments described herein.

Another particular embodiment of the invention relates to compounds with a structure according to formula (I1), (I2), (I3), or (I4)

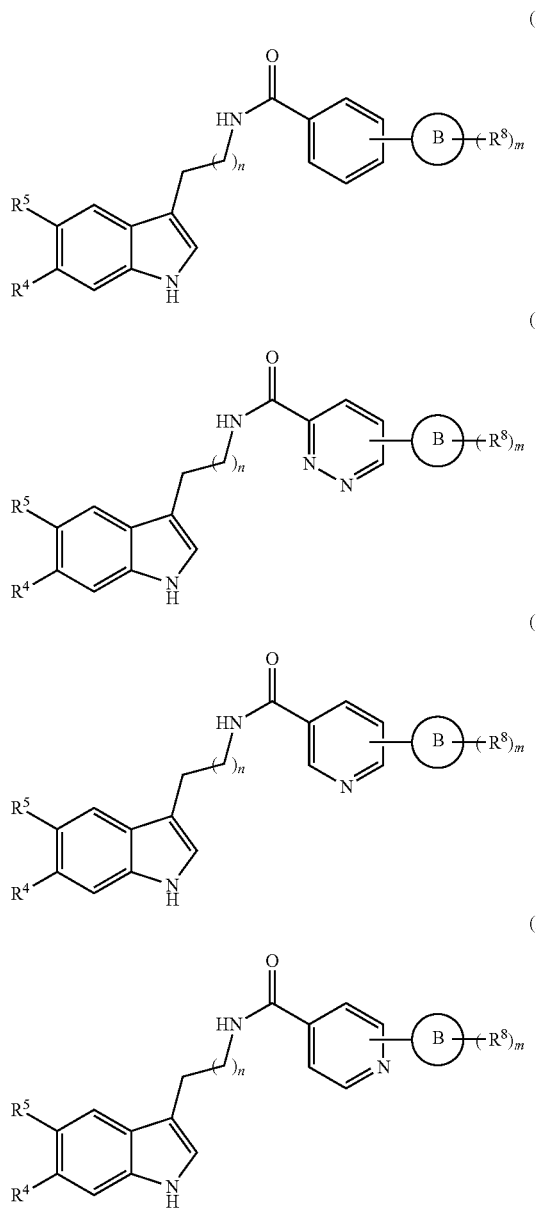

with the proviso that in formula (I1) when B is ortho-phenyl, then m is 1 or 2; and isomers (in particular stereoisomers, enantiomers or tautomers), solvates, hydrates, salts (in particular pharmaceutically acceptable salts) or prodrugs thereof.

The term "ortho-phenyl" present in the proviso within the definition of "B" and for formula (I1), indicates that a phenyl ring is located in position ortho versus the phenyl ring depicted in formula (I1).

Another particular embodiment of the invention relates to compounds with a structure according to formula (J1), (J2), (J3), or (J4)

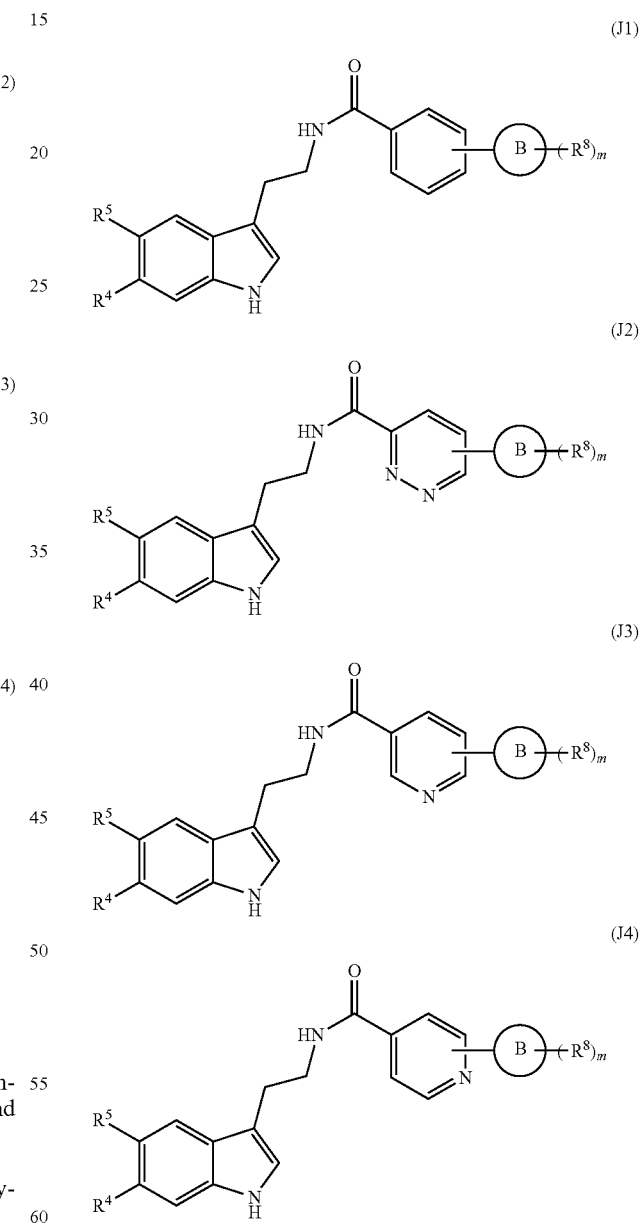

wherein
R$^4$ is selected from hydrogen and halogen;
R$^5$ is selected from halogen; —OH; —OR$^{10}$; trifluoromethyl; trifluoromethoxy; cyano; —C(O)R$^{11}$; and C$_{1-6}$alkyl;
n is selected from 0; 1; and 2;
B represents a cyclic structure selected from C$_{3-8}$cycloalkyl; C$_{6-10}$aryl; and heterocycle;
m is selected from 0; 1; and 2;
each R$^8$ is independently selected from halogen; C$_{1-6}$alkyl; —OH; C$_{1-6}$alkoxy; —COOR$^{20}$; trifluoromethyl; trifluoromethoxy; and cyano;
each R$^{10}$ is C$_{1-6}$alkyl;
each R$^{11}$ is C$_{1-6}$alkyl;
each R$^{20}$ is C$_{1-6}$alkyl;

wherein
R$^4$ is selected from hydrogen and halogen;
R$^5$ is selected from halogen; —OH; —OR$^{10}$; trifluoromethyl; trifluoromethoxy; cyano; —C(O)R$^{11}$; and C$_{1-6}$alkyl;

B represents a cyclic structure selected from $C_{3-8}$cycloalkyl; $C_{6-10}$aryl; and heterocycle;

m is selected from 0; 1; and 2;

each $R^8$ is independently selected from halogen; $C_{1-6}$alkyl; —OH; $C_{1-6}$alkoxy; —COOR$^{20}$; trifluoromethyl; trifluoromethoxy; and cyano;

each $R^{10}$ is $C_{1-6}$alkyl;

each $R^{11}$ is $C_{1-6}$alkyl;

each $R^{20}$ is $C_{1-6}$alkyl;

with the proviso that in formula (J1) when B is ortho-phenyl, then m is 1 or 2;

and isomers (in particular stereoisomers, enantiomers or tautomers), solvates, hydrates, salts (in particular pharmaceutically acceptable salts) or prodrugs thereof.

The term "ortho-phenyl" present in the proviso within the definition of "B" and for formula (J1), indicates that a phenyl ring is located in position ortho versus the phenyl ring depicted in formula (J1).

Another particular embodiment of the invention relates to compounds with a structure according to formula (K1), (K2), (K3), or (K4)

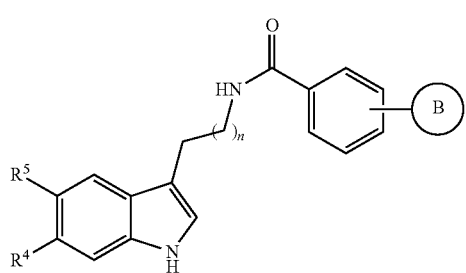
(K1)

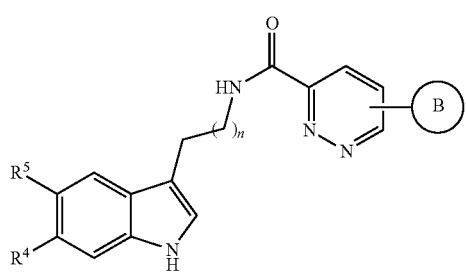
(K2)

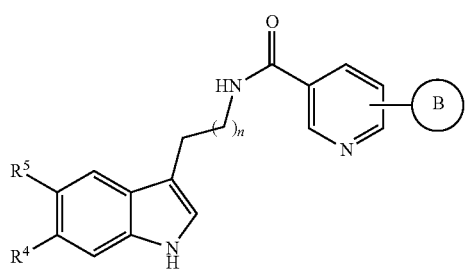
(K3)

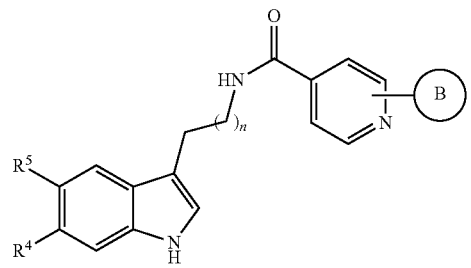
(K4)

wherein $R^4$ is selected from hydrogen and halogen;

$R^5$ is selected from halogen; —OH; —OR$^{10}$; trifluoromethyl; trifluoromethoxy; cyano; —C(O)R$^{11}$; and $C_{1-6}$alkyl;

n is selected from 0; 1; and 2;

B is selected from $C_{3-8}$cycloalkyl, meta-$C_{6-10}$aryl, para-$C_{6-10}$aryl, and heterocycle; each independently optionally substituted with one or two $R^8$ substituents; or B is an ortho-$C_{6-10}$aryl substituted with one or two $R^8$ substituents;

each $R^8$ is independently selected from halogen; $C_{1-6}$alkyl; —OH; $C_{1-6}$alkoxy; —COOR$^{20}$; trifluoromethyl; trifluoromethoxy; and cyano;

each $R^{10}$ is $C_{1-6}$alkyl;

each $R^{11}$ is $C_{1-6}$alkyl;

each $R^{20}$ is $C_{1-6}$alkyl;

and isomers (in particular stereoisomers, enantiomers or tautomers), solvates, hydrates, salts (in particular pharmaceutically acceptable salts) or prodrugs thereof.

Within the definition of "B", the term meta-$C_{6-10}$aryl indicates that an $C_{6-10}$aryl group is located in position meta versus any one of the phenyl, piridazinyl, and pyridinyl rings depicted in formulae (K1), (K2), (K3) and (K4), respectively.

Within the definition of "B", the term para-$C_{6-10}$aryl indicates that an $C_{6-10}$aryl group is located in position para versus any one of the phenyl, piridazinyl, and pyridinyl rings depicted in formulae (K1), (K2), (K3) and (K4), respectively.

Within the definition of "B", the term ortho-$C_{6-10}$aryl indicates that an $C_{6-10}$aryl group is located in position ortho versus any one of the phenyl, piridazinyl, and pyridinyl rings depicted in formulae (K1), (K2), (K3) and (K4), respectively.

Another particular embodiment of the invention relates to compounds with a structure according to formula (L1), (L2), (L3), or (L4)

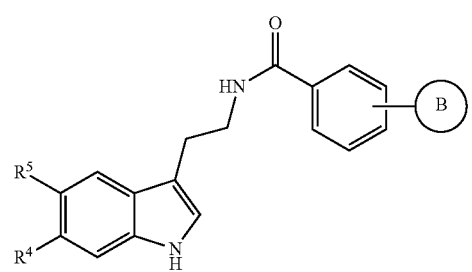
(L1)

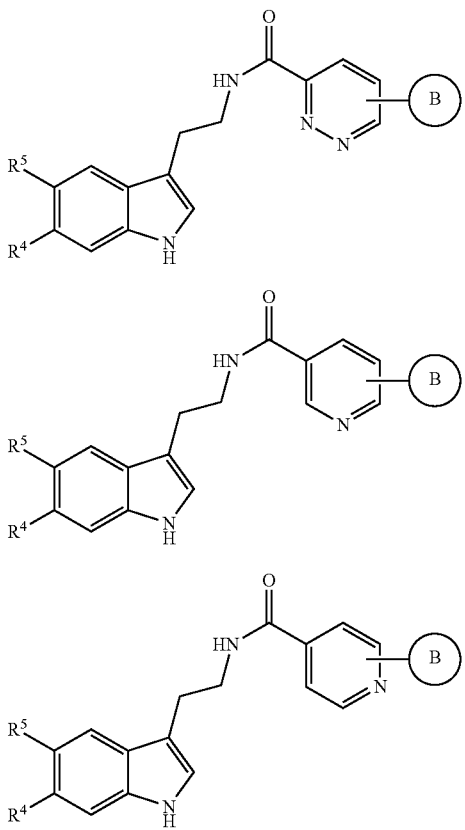

wherein
- R⁴ is selected from hydrogen and halogen;
- R⁵ is selected from halogen; —OH; —OR¹⁰; trifluoromethyl; trifluoromethoxy; cyano; —C(O)R¹¹; and $C_{1-6}$alkyl;
- B is selected from $C_{3-8}$cycloalkyl, meta-$C_{6-10}$aryl, para-$C_{6-10}$aryl, and heterocycle; each independently optionally substituted with one or two R⁸ substituents; or B is an ortho-$C_{6-10}$aryl substituted with one or two R⁸ substituents;
- each R⁸ is independently selected from halogen; $C_{1-6}$alkyl; —OH; $C_{1-6}$alkoxy; —COOR²⁰; trifluoromethyl; trifluoromethoxy; and cyano;
- each R¹⁰ is $C_{1-6}$alkyl;
- each R¹¹ is $C_{1-6}$alkyl;
- each R²⁰ is $C_{1-6}$alkyl;

and isomers (in particular stereoisomers, enantiomers or tautomers), solvates, hydrates, salts (in particular pharmaceutically acceptable salts) or prodrugs thereof.

Within the definition of "B", the term meta-$C_{6-10}$aryl indicates that an $C_{6-10}$aryl group is located in position meta versus any one of the phenyl, piridazinyl, and pyridinyl rings depicted in formulae (L1), (L2), (L3) and (L4), respectively.

Within the definition of "B", the term para-$C_{6-10}$aryl indicates that an $C_{6-10}$aryl group is located in position para versus any one of the phenyl, piridazinyl, and pyridinyl rings depicted in formulae (L1), (L2), (L3) and (L4), respectively.

Within the definition of "B", the term ortho-$C_{6-10}$aryl indicates that an $C_{6-10}$aryl group is located in position ortho versus any one of the phenyl, piridazinyl, and pyridinyl rings depicted in formulae (L1), (L2), (L3) and (L4), respectively.

In a particular embodiment, the compounds of the present invention are selected from the list of:
- N-(2-(5-methoxy-1H-indol-3-yl)ethyl)biphenyl-4-carboxamide;
- N-(2-(5-chloro-1H-indol-3-yl)ethyl)biphenyl-4-carboxamide;
- N-(2-(5-fluoro-1H-indol-3-yl)ethyl)biphenyl-4-carboxamide;
- N-(2-(5-methyl-1H-indol-3-yl)ethyl)biphenyl-4-carboxamide;
- ethyl 5-amino-1-(4-(2-(5-methyl-1H-indol-3-yl)ethylcarbamoyl)phenyl)-1H-pyrazole-4-carboxylate;
- N-(2-(5-chloro-1H-indol-3-yl)ethyl)-2-morpholinoisonicotinamide;
- N-(2-(5-fluoro-1H-indol-3-yl)ethyl)-2-morpholinoisonicotinamide;
- N-(2-(5-chloro-1H-indol-3-yl)ethyl)biphenyl-2-carboxamide;
- N-(2-(5-chloro-1H-indol-3-yl)ethyl)-4-(thiophen-2-yl)benzamide;
- N-(2-(5-chloro-1H-indol-3-yl)ethyl)biphenyl-3-carboxamide;
- N-(2-(5-chloro-1H-indol-3-yl)ethyl)-2',6'-dimethylbiphenyl-4-carboxamide;
- N-(2-(5-chloro-1H-indol-3-yl)ethyl)-4'-hydroxybiphenyl-2-carboxamide;
- N-(2-(5-chloro-1H-indol-3-yl)ethyl)-4'-hydroxybiphenyl-3-carboxamide;
- N-(2-(5-chloro-1H-indol-3-yl)ethyl)-4'-hydroxybiphenyl-4-carboxamide;
- N-(2-(5-chloro-1H-indol-3-yl)ethyl)-2'-methylbiphenyl-2-carboxamide;
- N-(2-(5-chloro-1H-indol-3-yl)ethyl)-2'-methylbiphenyl-3-carboxamide;
- N-(2-(5-chloro-1H-indol-3-yl)ethyl)-2'-methylbiphenyl-4-carboxamide;
- N-(2-(5-chloro-1H-indol-3-yl)ethyl)-3'-methylbiphenyl-2-carboxamide;
- N-(2-(5-chloro-1H-indol-3-yl)ethyl)-3'-methylbiphenyl-3-carboxamide;
- N-(2-(5-chloro-1H-indol-3-yl)ethyl)-3'-methylbiphenyl-4-carboxamide;
- N-(2-(5-chloro-1H-indol-3-yl)ethyl)-4'-methylbiphenyl-2-carboxamide;
- N-(2-(5-chloro-1H-indol-3-yl)ethyl)-4'-methylbiphenyl-3-carboxamide;
- N-(2-(5-chloro-1H-indol-3-yl)ethyl)-4'-methylbiphenyl-4-carboxamide;
- N-(2-(5-chloro-1H-indol-3-yl)ethyl)-6-morpholinonicotinamide;
- N-(2-(5-chloro-1H-indol-3-yl)ethyl)-2-(1H-pyrazol-1-yl)benzamide;
- N-(2-(5-chloro-1H-indol-3-yl)ethyl)-2'-methoxpiphenyl-2-carboxamide;
- N-(2-(5-chloro-1H-indol-3-yl)ethyl)-2'-methoxpiphenyl-3-carboxamide;
- N-(2-(5-chloro-1H-indol-3-yl)ethyl)-2'-methoxpiphenyl-4-carboxamide;
- N-(2-(5-chloro-1H-indol-3-yl)ethyl)-3'-methoxpiphenyl-2-carboxamide;
- N-(2-(5-chloro-1H-indol-3-yl)ethyl)-3'-methoxpiphenyl-3-carboxamide;
- N-(2-(5-chloro-1H-indol-3-yl)ethyl)-3'-methoxpiphenyl-4-carboxamide;
- N-(2-(5-chloro-1H-indol-3-yl)ethyl)-4'-methoxpiphenyl-2-carboxamide;

N-(2-(5-chloro-1H-indol-3-yl)ethyl)-4'-methoxpiphenyl-3-carboxamide;
N-(2-(5-chloro-1H-indol-3-yl)ethyl)-4'-methoxpiphenyl-4-carboxamide;
N-(2-(5-chloro-1H-indol-3-yl)ethyl)-2'-fluorobiphenyl-2-carboxamide;
N-(2-(5-chloro-1H-indol-3-yl)ethyl)-2'-fluorobiphenyl-3-carboxamide;
N-(2-(5-chloro-1H-indol-3-yl)ethyl)-2'-fluorobiphenyl-4-carboxamide;
N-(2-(5-chloro-1H-indol-3-yl)ethyl)-3'-fluorobiphenyl-2-carboxamide;
N-(2-(5-chloro-1H-indol-3-yl)ethyl)-3'-fluorobiphenyl-4-carboxamide;
N-(2-(5-chloro-1H-indol-3-yl)ethyl)-4'-fluorobiphenyl-2-carboxamide;
N-(2-(5-chloro-1H-indol-3-yl)ethyl)-4'-fluorobiphenyl-3-carboxamide;
N-(2-(5-chloro-1H-indol-3-yl)ethyl)-4'-fluorobiphenyl-4-carboxamide;
N-(2-(5-chloro-1H-indol-3-yl)ethyl)-2'-cyanobiphenyl-3-carboxamide;
N-(2-(5-chloro-1H-indol-3-yl)ethyl)-2'-cyanobiphenyl-4-carboxamide;
N-(2-(5-chloro-1H-indol-3-yl)ethyl)-3-(pyridin-4-yl)benzamide;
N-(2-(5-chloro-1H-indol-3-yl)ethyl)-4-(pyridin-4-yl)benzamide;
N-(2-(5-chloro-1H-indol-3-yl)ethyl)-3'-fluorobiphenyl-3-carboxamide;
N-(2-(5-chloro-1H-indol-3-yl)ethyl)-3'-cyanobiphenyl-2-carboxamide;
N-(2-(5-chloro-1H-indol-3-yl)ethyl)-3'-cyanobiphenyl-3-carboxamide;
N-(2-(5-chloro-1H-indol-3-yl)ethyl)-3'-cyanobiphenyl-4-carboxamide;
N-(2-(5-chloro-1H-indol-3-yl)ethyl)-4'-cyanobiphenyl-2-carboxamide;
N-(2-(5-chloro-1H-indol-3-yl)ethyl)-4'-cyanobiphenyl-3-carboxamide;
N-(2-(5-chloro-1H-indol-3-yl)ethyl)-4'-cyanobiphenyl-4-carboxamide;
2'-chloro-N-(2-(5-chloro-1H-indol-3-yl)ethyl)biphenyl-2-carboxamide;
2'-chloro-N-(2-(5-chloro-1H-indol-3-yl)ethyl)biphenyl-3-carboxamide;
2'-chloro-N-(2-(5-chloro-1H-indol-3-yl)ethyl)biphenyl-4-carboxamide;
3'-chloro-N-(2-(5-chloro-1H-indol-3-yl)ethyl)biphenyl-2-carboxamide;
3'-chloro-N-(2-(5-chloro-1H-indol-3-yl)ethyl)biphenyl-3-carboxamide;
3'-chloro-N-(2-(5-chloro-1H-indol-3-yl)ethyl)biphenyl-4-carboxamide;
4'-chloro-N-(2-(5-chloro-1H-indol-3-yl)ethyl)biphenyl-3-carboxamide;
4'-chloro-N-(2-(5-chloro-1H-indol-3-yl)ethyl)biphenyl-4-carboxamide;
N-(2-(5-chloro-1H-indol-3-yl)ethyl)-2'-(trifluoromethyl)biphenyl-4-carboxamide;
4'-chloro-N-(2-(5-chloro-1H-indol-3-yl)ethyl)biphenyl-2-carboxamide;
N-(2-(5-chloro-1H-indol-3-yl)ethyl)-3'-(trifluoromethyl)biphenyl-2-carboxamide;
N-(2-(5-chloro-1H-indol-3-yl)ethyl)-2'-(trifluoromethyl)biphenyl-3-carboxamide;
N-(2-(5-chloro-1H-indol-3-yl)ethyl)-3'-(trifluoromethyl)biphenyl-4-carboxamide;
N-(2-(5-chloro-1H-indol-3-yl)ethyl)-4'-(trifluoromethyl)biphenyl-2-carboxamide;
N-(2-(5-chloro-1H-indol-3-yl)ethyl)-4'-(trifluoromethyl)biphenyl-3-carboxamide;
N-(2-(5-chloro-1H-indol-3-yl)ethyl)-3'-(trifluoromethyl)biphenyl-3-carboxamide;
N-(2-(5-chloro-1H-indol-3-yl)ethyl)-2',6'-dimethylbiphenyl-3-carboxamide;
N-(2-(5-chloro-1H-indol-3-yl)ethyl)-3',4'-dimethylbiphenyl-2-carboxamide;
N-(2-(5-chloro-1H-indol-3-yl)ethyl)-3',4'-dimethylbiphenyl-3-carboxamide;
N-(2-(5-chloro-1H-indol-3-yl)ethyl)-3',4'-dimethylbiphenyl-4-carboxamide;
N-(2-(5-chloro-1H-indol-3-yl)ethyl)-4'-(trifluoromethyl)biphenyl-4-carboxamide;
N-(2-(5-chloro-1H-indol-3-yl)ethyl)-6-phenylpyridazine-3-carboxamide;
2-(1H-pyrazol-1-yl)-N-(2-(5-(trifluoromethyl)-1H-indol-3-yl)ethyl)benzamide;
3-(pyridin-3-yl)-N-(2-(5-(trifluoromethyl)-1H-indol-3-yl)ethyl)benzamide;
4-(furan-2-yl)-N-(2-(5-(trifluoromethyl)-1H-indol-3-yl)ethyl)benzamide;
N-(2-(5-cyano-1H-indol-3-yl)ethyl)-3'-fluorobiphenyl-2-carboxamide;
N-(2-(5-cyano-1H-indol-3-yl)ethyl)-3-(1H-imidazol-5-yl)benzamide;
N-(2-(5-cyano-1H-indol-3-yl)ethyl)-4-(thiophen-3-yl)benzamide;
N-(2-(5,6-dichloro-1H-indol-3-yl)ethyl)-2-(1H-pyrazol-1-yl)benzamide;
N-(2-(5,6-dichloro-1H-indol-3-yl)ethyl)-2'-methylbiphenyl-3-carboxamide;
N-(2-(5,6-dichloro-1H-indol-3-yl)ethyl)-4-(pyridin-4-yl)benzamide;
3'-chloro-N-(2-(6-chloro-5-methyl-1H-indol-3-yl)ethyl)biphenyl-2-carboxamide;
N-(2-(6-chloro-5-methyl-1H-indol-3-yl)ethyl)-2'-cyanobiphenyl-3-carboxamide;
N-(2-(6-chloro-5-methyl-1H-indol-3-yl)ethyl)-4-(pyridin-2-yl)benzamide;
N-(2-(5-acetyl-1H-indol-3-yl)ethyl)-2-(oxazol-5-yl)benzamide;
N-(2-(5-acetyl-1H-indol-3-yl)ethyl)-4'-hydroxybiphenyl-3-carboxamide;
N-(2-(5-acetyl-1H-indol-3-yl)ethyl)-2'-chlorobiphenyl-4-carboxamide;
N-(2-(5-chloro-1H-pyrrolo[2,3-b]pyridin-3-yl)ethyl)-2-(oxazol-2-yl)benzamide;
N-(2-(5-chloro-1H-pyrrolo[2,3-b]pyridin-3-yl)ethyl)-3'-hydroxybiphenyl-3-carboxamide;
N-(2-(5-chloro-1H-pyrrolo[2,3-b]pyridin-3-yl)ethyl)-4-(thiophen-2-yl)benzamide;
N-(2-(5-chloro-1H-indol-3-yl)ethyl)-2-(thiophen-3-yl)benzamide;
N-(2-(5-chloro-1H-indol-3-yl)ethyl)-3-(pyridin-2-yl)benzamide;
N-(2-(5-chloro-1H-indol-3-yl)ethyl)-4-(oxazol-2-yl)benzamide;
N-(2-(5-chloro-1H-indol-3-yl)ethyl)-6-(pyridin-3-yl)pyridazine-3-carboxamide;
N-(2-(6-chloro-5-methyl-1H-indol-3-yl)ethyl)-6-(1-methyl-1H-pyrazol-4-yl)pyridazine-3-carboxamide;

N-((5-chloro-1H-indol-3-yl)methyl)-3'-fluorobiphenyl-3-carboxamide;

N-((5-chloro-1H-indol-3-yl)methyl)-4-(oxazol-5-yl)benzamide;

N-((5-chloro-1H-indol-3-yl)methyl)-6-(pyridin-4-yl)pyridazine-3-carboxamide;

N-(3-(5-chloro-1H-indol-3-yl)propyl)-2-(1H-pyrazol-1-yl)benzamide;

N-(3-(5-chloro-1H-indol-3-yl)propyl)-3'-fluorobiphenyl-3-carboxamide; and

N-(3-(5-chloro-1H-indol-3-yl)propyl)-4-(oxazol-2-yl)benzamide.

Another aspect of the present invention provides a pharmaceutical composition comprising one or more pharmaceutically acceptable excipients and a therapeutically effective amount of a compound according to the invention.

Another aspect of the present invention provides the compounds according to formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), (J4), (K1), (K2), (K3), (K4), (L1), (L2), (L3), or (L4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, for use as a medicine or a medicament.

In a particular embodiment, the invention provides the compounds for use a medicine for the prevention or treatment of neurodegenerative disorders, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The present invention also provides for the use of the compounds according to formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), (J4), (K1), (K2), (K3), (K4), (L1), (L2), (L3), or (L4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof, for the manufacture of a medicament for the prevention or treatment of a disorder in an animal, more in particular a mammal or a human.

In a particular embodiment, the invention provides for the use of the compounds as described herein for the manufacture of a medicament for the prevention or treatment of a neurodegenerative disorder in an animal, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the invention relates to a method for the prevention or treatment of a disorder in animals, more particularly mammals or humans, by the administration of an effective amount of one or more such compounds according to formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), (J4), (K1), (K2), (K3), (K4), (L1), (L2), (L3), or (L4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof to a patient in need thereof. In a particular embodiment, said disorder is a neurodegenerative disorder, wherein more particularly, the neurodegenerative disorder is selected from Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

Another aspect of the present invention provides a pharmaceutical composition comprising one or more pharmaceutically acceptable carriers or excipients and a therapeutically effective amount of a compound according to formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), (J4), (K1), (K2), (K3), (K4), (L1), (L2), (L3), or (L4) or any subgroup thereof, or all other formulas herein or according to all embodiments described herein, and isomers (in particular stereo-isomers or tautomers), solvates, hydrates, salts (in particular pharmaceutically acceptable salts) or prodrugs thereof.

In a particular embodiment, the present invention relates to pharmaceutical compositions comprising the compounds of the invention according to formulae, embodiments and claims herein in admixture with at least a pharmaceutically acceptable carrier, the active compounds preferably being in a concentration range of about 0.1 to 100% by weight.

The invention further relates to the use of a composition comprising (a) one or more compounds of the invention (of formulae, embodiments and claims herein), and (b) one or more drugs known for the (symptomatic) prevention or treatment of neurodegenerative disorders.

Yet another aspect of the invention provides a method for the preparation of the compounds of the invention which comprises the following steps (with the knowledge that where indole is described, the same counts for the corresponding heterocycles as described herein i.e. azaindole):

reacting a substituted or unsubstituted (1H-indol-3-yl) methanamine, 2-(1H-indol-3-yl)ethanamine or 3-(1H-indol-3-yl)propan-1-amine with a correctly substituted six membered ring derivative bearing an acid halide function in a polar aprotic solvent in the presence of a strong base at a temperature between −10° C. to 100° C.;

reacting a substituted or unsubstituted (1H-indol-3-yl) methanamine, 2-(1H-indol-3-yl)ethanamine or 3-(1H-indol-3-yl)propan-1-amine with a correctly substituted six membered ring derivative bearing one carboxylic acid function in a polar aprotic solvent in the presence of a peptide bond formation coupling agent at a temperature between 0° C. to 50° C.;

optionally reacting the compound obtained in the previous step, wherein the six membered ring bears a leaving group (LG), with suitable nucleophiles (e.g. amines, alcohols) and in the presence of a strong base or with derivatives such as boronic acids, stannanes or organozinc derivatives in the presence of a palladium or cupper catalyst.

Also the intermediates used in the preparation methods described herein are aspects of the present invention.

Particular embodiments of the inventions are also described in the claims and relate to especially useful subtypes of the compounds of the invention. In particular embodiments, the terms alkyl, alkenyl or alkynyl can be restricted to refer to their cyclic or linear subgroups (such as the linear alkyl or cycloalkyl for alkyl).

More generally, the invention relates to the compounds of formula and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

DETAILED DESCRIPTION OF THE INVENTION

Figure 1:
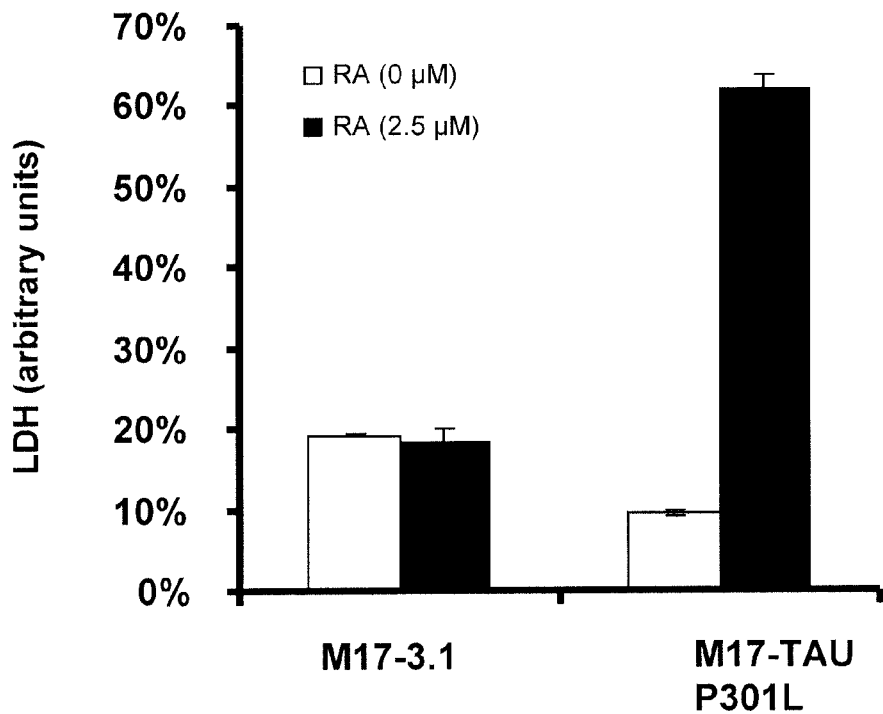
FIG. 1 shows the sensitivity of a TAU(301) expressing neuroblastoma cell line to retinoic acid-instigated differentiation.

As used in the foregoing and hereinafter, the following definitions apply unless otherwise noted.

The terminology "which optionally includes one or more heteroatoms, said heteroatoms being selected from the atoms consisting of O, S, and N" as used herein, refers to a group where one or more carbon atoms are replaced by an oxygen, nitrogen or sulphur atom and thus includes, depending on the group to which is referred, heteroalkyl, heteroalkenyl, heteroalkynyl, heteroalkylene, heteroalkenylene, heteroalkynylene, cycloheteroalkyl, cycloheteroalkenyl, cycloheteroalkynyl, heteroaryl, arylheteroalkyl(ene), heteroarylalkyl(ene), heteroarylheteroalkyl(ene), arylheteroalkenyl(ene), heteroarylalkenyl(ene), heteroarylheteroalkenyl(ene), heteroarylheteroalkenyl(ene), arylheteroalkynyl(ene), heteroarylalkynyl(ene), heteroarylheteroalkynyl(ene), among others. In other words, this term means that —CH₃ can be replaced by —NH₂; —CH₂— by —NH—, —O— or —S—; a —CH= by —N=; and ≡CH by ≡N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. As an example, the terminology "alkyl which optionally includes one or more heteroatoms, said heteroatoms being selected from the atoms consisting of O, S, and N" therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain. Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples. As an example, the terminology "arylalkylene which optionally includes one or more heteroatoms in the alkylene chain, said heteroatoms being selected from the atoms consisting of O, S, and N" therefore refers to arylheteroalkylene, meaning an arylalkylene which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkylene" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$— among many other examples. The same counts for "heteroalkenylene", "heteroalkynylene", and other terms used herein when referred to "which optionally includes one or more heteroatoms, said heteroatoms being selected from the atoms consisting of O, S, and N".

The terminology regarding a chemical group "wherein optionally two or more hydrogen atoms on a carbon atom or heteroatom of said group can be taken together to form a C=O, C=S, N=O, N=S, S=O or S(O)₂" as used herein, refers to a group where two or more hydrogen atoms on a carbon atom or heteroatom of said group are taken together to form C=O, C=S, N=O, N=S, S=O or S(O)₂. In other words, the expression means that a carbon atom or heteroatom of said group can be oxidized to form a C=O, C=S, N=O, N=S, S=O or S(O)₂. As an example, the terminology refers to "an alkyl wherein optionally two or more hydrogen atoms on a carbon atom or heteroatom of said alkyl can be taken together to form a C=O, C=S, N=O, N=S, S=O or S(O)₂", includes among other examples $CH_3$—C(O)—$CH_2$—, $CH_3$—C(O)—, $CH_3$—C(S)—$CH_2$— and $(CH_3)_2$—$CH_2$—C(O)—$CH_2$—$CH_2$—. As another example, as used herein and unless otherwise stated, the expression "two or more hydrogen atoms on a carbon atom or heteroatom of said heterocycle can be taken together to form a C=O, C=S, N=O, N=S, S=O or S(O)₂" means that a carbon atom or heteroatom of the ring can be oxidized to form a C=O, C=S, N=O, N=S, S=O or S(O)₂.

The combination for a group "which optionally includes one or more heteroatoms, said heteroatoms being selected from the atoms consisting of O, S, and N" and "wherein optionally two or more hydrogen atoms on a carbon atom or heteroatom of said group can be taken together to form a C=O, C=S, N=O, N=S, S=O or S(O)₂" can combine the two aspects described herein above and includes, if the group referred to is alkyl, among other examples $CH_3$—COO—, $CH_3$—COO—$CH_2$—, $CH_3$—NH—CO—, $CH_3$—NH—CO—$OH_2$—, $CH_3$—NH—CS—$CH_2$—, $CH_3$—NH—CS—NH—$CH_2$—, $CH_3$—NH—S(O)₂— and $CH_3$—NH—S(O)₂—NH—$CH_2$—.

The term "leaving group" as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl (i-Bu), 2-butyl(s-Bu) 2-methyl-2-propyl(t-Bu), 1-pentyl(n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons, also termed as $C_{1-6}$alkyl, as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl(s-Bu) 2-methyl-2-propyl(t-Bu), 1-pentyl(n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl. In a particular embodiment, the term cycloalkyl refers to $C_{3-8}$cycloalkyl, which is a generic term for cyclopropyl, cyclobutyl, cyclopentyl, cyclohexyl, cycloheptyl, and cyclooctyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$), cyclopentenyl (—$C_5H_7$), cyclohexenyl (—$C_6H_9$) and 5-hexenyl (—$CH_2CH_2CH_2CH_2$CH=$CH_2$). The double bond may be in the cis or trans configuration. In a particular embodiment, the term alkenyl refers to $C_{2-12}$ hydrocarbons, yet more in particular to $C_{2-6}$ hydrocarbons, also termed as $C_{2-6}$alkenyl, as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=$CH_2$), allyl (—$CH_2$CH=$CH_2$) and 5-hexenyl (—$CH_2CH_2CH_2CH_2$CH=$CH_2$). The double bond may be in the cis or trans configuration.

The term "cycloalkenyl" as used herein refers to $C_4$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—$C_5H_7$) and cyclohexenyl (—$C_6H_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH). In a particular embodiment, the term alkenyl refers to $C_{2-12}$ hydrocarbons, yet more in particular to $C_{2-6}$ hydrocarbons, also termed as $C_{2-6}$alkynyl, as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—$CH_2$C≡CH).

The term "cycloalkynyl" as used herein refers to $C_6$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene (—$CH_2$—) 1,2-ethylene (—$CH_2CH_2$—), 1,2-propylene, 1,3-propylene (—$CH_2CH_2CH_2$—), 1,4-butylene (—$CH_2CH_2CH_2CH_2$—), 1,3-butylene, 1,2-butylene, and the like.

The term "aryl" as used herein means a aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like.

"Arylalkylene" as used herein refers to an alkyl radical in which one of the hydrogen atoms bonded to a carbon atom, typically a terminal or sp3 carbon atom, is replaced with an aryl radical. Typical arylalkylene groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkylene group comprises 6 to 20 carbon atoms, e.g. the alkylene moiety of the arylalkylene group is 1 to 6 carbon atoms and the aryl moiety is 5 to 14 carbon atoms.

"Arylalkenylene" as used herein refers to an alkenylene radical in which one of the hydrogen atoms bonded to a carbon atom, is replaced with an aryl radical. The arylalkenylene group comprises 6 to 20 carbon atoms, e.g. the alkenylene moiety of the arylalkenylene group is 2 to 6 carbon atoms and the aryl moiety is 5 to 14 carbon atoms.

"Arylalkynylene" as used herein refers to an alkynyl radical in which one of the hydrogen atoms bonded to a carbon atom, is replaced with an aryl radical. The arylalkynylene group comprises 6 to 20 carbon atoms, e.g. the alkynylene moiety of the arylalkynylene group is 2 to 6 carbon atoms and the aryl moiety is 5 to 14 carbon atoms.

The term "heterocycle" as used herein means a saturated, unsaturated or aromatic ring system including at least one N, O, S, or P. Heterocycle thus include heteroaryl groups. Heterocycle as used herein includes by way of example and not limitation these heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl and isatinoyl.

"Heterocycle-alkylene" as used herein refers to an alkyl radical in which one of the hydrogen atoms bonded to a carbon atom, typically a terminal or sp3 carbon atom, is replaced with a heterocycle radical. An example of a heterocycle-alkylene group is 2-pyridyl-methylene. The heterocycle-alkylene group comprises 6 to 20 carbon atoms, e.g. the alkylene moiety of the heterocycle-alkyl group is 1 to 6 carbon atoms and the heterocycle moiety is 5 to 14 carbon atoms.

"Heterocycle-alkenylene" as used herein refers to an alkenyl radical in which one of the hydrogen atoms bonded to a carbon atom, is replaced with an heterocycle radical. The heterocycle-alkenylene group comprises 6 to 20 carbon atoms, e.g. the alkenylene moiety of the heterocycle-alkenylene group is 2 to 6 carbon atoms and the heterocycle moiety is 5 to 14 carbon atoms.

"Heterocycle-alkynylene" as used herein refers to an alkynylene radical in which one of the hydrogen atoms bonded to a carbon atom, is replaced with a heterocycle radical. The heterocycle-alkynylene group comprises 6 to 20 carbon atoms, e.g. the alkynylene moiety of the heterocycle-alkynylene group is 2 to 6 carbon atoms and the heterocycle moiety is 5 to 14 carbon atoms.

"Heteroaryl" means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkylene" as used herein refers to an alkyl radical in which one of the hydrogen atoms bonded to a carbon atom, typically a terminal or sp3 carbon atom, is replaced with a heterocycle radical. An example of a heteroaryl-alkylene group is 2-pyridyl-methylene. The heteroaryl-alkylene group comprises 6 to 20 carbon atoms, e.g. the alkylene moiety of the heteroaryl-alkylene group is 1 to 6 carbon atoms and the heteroaryl moiety is 5 to 14 carbon atoms.

"Heteroaryl-alkenylene" as used herein refers to an alkenyl radical in which one of the hydrogen atoms bonded to a carbon atom, is replaced with an heteroaryl radical. The heteroaryl-alkenylene group comprises 6 to 20 carbon atoms, e.g. the alkenylene moiety of the heteroaryl-alkenylene group is 2 to 6 carbon atoms and the heteroaryl moiety is 5 to 14 carbon atoms.

"Heteroaryl-alkynylene" as used herein refers to an alkynyl radical in which one of the hydrogen atoms bonded to a carbon atom, is replaced with a heteroaryl radical. The heteroaryl-alkynylene group comprises 6 to 20 carbon atoms, e.g. the alkynylene moiety of the heteroaryl-alkynylene group is 2 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocycle" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Whenever the term "substituted" is used in the present invention, and unless otherwise stated, it is meant to indicate that one or more hydrogens on the atom, or group indicated in the expression using "substituted" is replaced with one or more group each independently selected from halogen; alkyl; alkenyl; alkynyl; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; wherein R$^{10}$, R$^{11}$, R$^{12}$, R$^{13}$ have the same meaning as that defined herein.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occur stereospecifically. Preferably, if a specific stereoisomer is desired, said compound will be synthesized by stereospecific methods of preparation. These methods will advantageously employ enantiomerically pure starting materials.

The diastereomeric racemates of the compounds of the invention can be obtained separately by conventional methods. Appropriate physical separation methods that may advantageously be employed are, for example, selective crystallization and chromatography, e.g. column chromatography.

For therapeutic use, salts of the compounds of the invention are those wherein the counter-ion is pharmaceutically acceptable, which salts can be referred to as pharmaceutically acceptable acid and base addition salts. However, salts of acids and bases that are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove are meant to comprise the therapeutically active non-toxic acid and base addition salt forms that the compounds are able to form. The pharmaceutically acceptable acid addition salts can conveniently be obtained by treating the base form with such appropriate acid in an anion form. Appropriate anions comprise, for example, acetate, benzenesulfonate, benzoate, bicarbonate, bitartrate, bromide, calcium edetate, camsyiate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide, and the like. Conversely said salt forms can be converted by treatment with an appropriate base into the free base form.

The compounds of the invention containing an acidic proton may also be converted into their non-toxic metal or amine addition salt forms by treatment with appropriate organic and inorganic bases in a cation form. Appropriate basic salts comprise those formed with organic cations such as benzathine, chloroprocaine, choline, diethanolamine, ethylenediamine, meglumine, procaine, and the like; and those formed with metallic cations such as aluminum, calcium, lithium, magnesium, potassium, sodium, zinc, and the like. Conversely said salt forms can be converted by treatment with an appropriate acid into the free form.

As used herein and unless otherwise stated, the term "solvate" includes any combination which may be formed by a derivative of this invention with a suitable inorganic solvent (e.g. hydrates) or organic solvent, such as but not limited to alcohols, ketones, esters, ethers, nitriles and the like.

A first aspect of the present invention therefore provides compounds according to formula (AA1) or (A1),

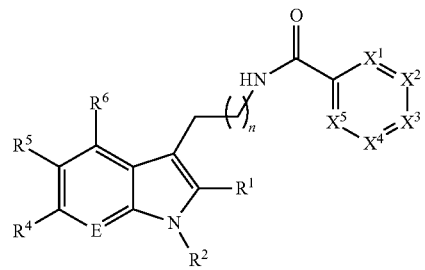

(AA1)

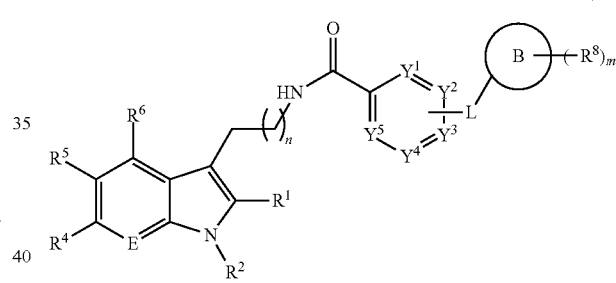

(A1)

wherein E, $R^1$, $R^2$, $R^3$, $R^4$, $R^5$, $R^6$, $R^8$, $Y^1$, $Y^2$, $Y^3$, $Y^4$, $Y^5$, $X^1$, $X^2$, $X^3$, $X^4$, $X^5$, B, m and n have the same meaning as that defined herein (including in the summary of the invention, the formulas and embodiments thereof).

According to an embodiment, the present invention provides compounds of Formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), or (J4) or any subgroup thereof, wherein E is $CR^3$; or N; preferably E is $CR^3$, each $R^1$, $R^4$ and $R^6$ is independently selected from hydrogen; halogen; —OH; —$OR^{10}$; —SH; —$SR^{10}$; —$S(O)R^{11}$; —$S(O)_2R^{11}$; —$SO_2NR^{12}R^{13}$; trifluoromethyl; trifluoromethoxy; nitro; —$NHC(O)R^{10}$; —$NHS(O)_2R^{10}$; —$NHC(O)NR^{12}R^{13}$; —$NR^{10}C(O)R^{10}$; —$NR^{10}S(O)_2R^{10}$; —$NR^{10}C(O)NR^{12}R^{13}$; —$NR^{12}R^{13}$; -cyano; —COOH; —$COOR^{10}$; —$C(O)NR^{12}R^{13}$; —$C(O)R^{11}$; $C_{1-6}$alkyl; $C_{2-6}$alkenyl; $C_{2-6}$alkynyl; $C_{6-10}$aryl; heterocycle; $C_{6-10}$aryl$C_{1-6}$alkylene; $C_{6-10}$aryl$C_{2-6}$alkenylene; $C_{6-10}$aryl$C_{2-6}$alkynylene; heterocycle-$C_{1-6}$alkylene; heterocycle-$C_{2-6}$alkenylene; and heterocycle-$C_{2-6}$alkynylene; preferably each $R^1$, $R^4$ and $R^6$ is independently selected from hydrogen; halogen; —OH; —$OR^{10}$; —SH; trifluoromethyl; trifluoromethoxy; nitro; —$NR^{12}R^{13}$; -cyano;

—COOH; —COOR$^{10}$; C$_{1-6}$alkyl; C$_{6-10}$aryl; heterocycle; C$_{6-10}$arylC$_{1-6}$alkylene; heterocycle-C$_{1-6}$alkylene; preferably each R$^1$, R$^4$ and R$^6$ is independently selected from hydrogen; halogen; —OH; —OC$_{1-4}$alkyl; trifluoromethyl; trifluoromethoxy; -cyano; C$_{1-4}$alkyl; C$_6$aryl; C$_6$arylC$_{1-6}$alkylene; preferably each R$^1$, R$^4$ and R$^6$ is independently selected from hydrogen; halogen; —OH; methoxy; trifluoromethyl; trifluoromethoxy; -cyano; C$_{1-4}$alkyl; C$_6$aryl; preferably each R$^1$, R$^4$ and R$^6$ is independently selected from hydrogen; halogen; —OH; trifluoromethyl; C$_{1-2}$alkyl; preferably each R$^1$, R$^4$ and R$^6$ is independently selected from hydrogen; fluoro; or chloro; preferably each R$^1$, R$^4$ and R$^6$ is independently hydrogen;

R$^3$ is selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; C$_{1-6}$alkyl; C$_{2-6}$alkenyl; C$_{2-6}$alkynyl; C$_{6-10}$aryl; heterocycle; C$_{6-10}$arylC$_{1-6}$alkylene; C$_{6-10}$arylC$_{2-6}$alkenylene; C$_{6-10}$arylC$_{2-6}$alkynylene; heterocycle-C$_{1-6}$alkylene; heterocycle-C$_{2-6}$alkenylene; and heterocycle-C$_{2-6}$alkynylene; preferably R$^3$ is selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; C$_{1-6}$alkyl; C$_{6-10}$aryl; heterocycle; C$_{6-10}$arylC$_{1-6}$alkylene; heterocycle-C$_{1-6}$alkylene; preferably R$^3$ is selected from hydrogen; halogen; —OH; trifluoromethyl; trifluoromethoxy; -cyano; C$_{1-4}$alkyl; C$_6$aryl; C$_6$arylC$_{1-6}$alkylene; preferably R$^3$ is selected from hydrogen; halogen; —OH; methoxy; trifluoromethyl; trifluoromethoxy; -cyano; C$_{1-4}$alkyl; C$_6$aryl; preferably R$^3$ is selected from hydrogen; halogen; —OH; trifluoromethyl; C$_{1-2}$alkyl; preferably R$^3$ is selected from hydrogen; fluoro; or chloro; preferably R$^3$ is hydrogen;

R$^2$ is selected from hydrogen; C$_{1-6}$alkyl; C$_{2-6}$alkenyl; and C$_{2-6}$alkynyl; preferably R$^2$ is selected from hydrogen; or C$_{1-6}$alkyl; preferably R$^2$ is selected from hydrogen; or C$_{1-2}$alkyl; preferably R$^2$ is hydrogen;

R$^5$ is selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; C$_{1-6}$alkyl; C$_{2-6}$alkenyl; C$_{2-6}$alkynyl; C$_{6-10}$aryl; heterocycle; C$_{6-10}$arylC$_{1-6}$alkylene; C$_{6-10}$arylC$_{2-6}$alkenylene; C$_{6-10}$arylC$_{2-6}$alkynylene; heterocycle-C$_{1-6}$alkylene; heterocycle-C$_{2-6}$alkenylene; and heterocycle-C$_{2-6}$alkynylene; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene; preferably R$^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)C$_{1-6}$alkyl; C$_{1-6}$alkyl; C$_{6-10}$aryl; heterocycle; C$_{6-10}$arylC$_{1-6}$alkylene; preferably R$^5$ is selected from halogen; -cyano; —OH; —OR$^{10}$; —SH; —SR$^{10}$; trifluoromethyl; trifluoromethoxy; —C(O)C$_{1-4}$alkyl; —NR$^{12}$R$^{13}$; C$_{1-6}$alkyl; phenyl; morpholinyl; preferably R$^5$ is selected from chloro, fluoro; -cyano; —OH; —OR$^{10}$; —SH; —SR$^{10}$; trifluoromethyl; trifluoromethoxy; C$_{1-6}$alkyl; phenyl; morpholinyl; preferably R$^5$ is selected from chloro, fluoro methyl, or cyano;

n is 1 or 0; preferably n is 1;

each of Y$^1$, Y$^2$, Y$^3$, Y$^4$ and Y$^5$ is independently selected from CZ$^1$; or N; wherein at least two of Y$^1$, Y$^2$, Y$^3$, Y$^4$ and Y$^5$ are selected from CZ$^1$; preferably each of Y$^1$, Y$^2$, Y$^3$, Y$^4$ and Y$^5$ is independently selected from CZ$^1$; or N; wherein at least three of Y$^1$, Y$^2$, Y$^3$, Y$^4$ and Y$^5$ are selected from CZ$^1$; preferably with Z$^1$ being selected from hydrogen, alkyl or Z$^2$, and Z$^2$ is halogen;

B is selected from aryl; cycloalkyl; and heterocycle; preferably B is selected from aryl; or heterocycle; preferably B is selected from C$_{6-10}$aryl; or heterocycle; B is selected from C$_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1, 2 or 3; preferably m is 0, 1 or 2, preferably m is 0 or 1;

each R$^8$ is independently selected from hydrogen; halogen; alkyl; alkenyl; alkynyl; —OH; —OR$^{20}$; —SH; trifluoromethyl; trifluoromethoxy; nitro; -cyano; —COOH; —COOR$^{20}$; —C(O)NR$^{22}$R$^{23}$; and —C(O)R$^{21}$; preferably each R$^8$ is independently selected from hydrogen; halogen; alkyl; —OH; —OR$^{20}$; —SH; trifluoromethyl; trifluoromethoxy; nitro; -cyano; preferably each R$^8$ is independently selected from hydrogen; halogen; alkyl; —OR$^{20}$; trifluoromethyl; trifluoromethoxy; -cyano; wherein R$^{20}$ is alkyl; preferably each R$^8$ is independently selected from hydrogen; halogen; C$_{1-6}$alkyl; —OR$^{20}$; trifluoromethyl; trifluoromethoxy; -cyano; wherein R$^{20}$ is C$_{1-6}$alkyl; preferably each R$^8$ is independently selected from hydrogen; halogen; C$_{1-4}$alkyl; —OR$^{20}$; trifluoromethyl; -cyano;

wherein $R^{20}$ is $C_{1-2}$alkyl; preferably each $R^8$ is independently selected from hydrogen; fluoro; chloro; $C_{1-2}$alkyl; —OCH$_3$; trifluoromethyl; -cyano;

each $Z^1$ is independently selected from hydrogen; $C_{1-6}$alkyl; and $Z^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NR$^{22}$R$^{23}$; -cyano; —COOH; —COOR$^{20}$; and —C(O)R$^{21}$; preferably each $Z^2$ is independently selected from halogen; —OH; —OR$^{20}$; —SH; trifluoromethyl; trifluoromethoxy; —NR$^{22}$R$^{23}$; -cyano; —COOH; —COOR$^{20}$; and —C(O)R$^{21}$; preferably each $Z^2$ is independently selected from halogen; —OH; —OC$_{1-6}$alkyl; trifluoromethyl; trifluoromethoxy; -cyano; preferably each $Z^2$ is independently selected from fluoro; chloro; —OH; —OC$_{1-3}$alkyl; trifluoromethyl; trifluoromethoxy; -cyano;

each $R^{10}$ is independently selected from alkyl; aryl; heterocycle; arylalkylene; heterocycle-alkylene; preferably each $R^{10}$ is independently selected from $C_{1-6}$alkyl; $C_{6-10}$aryl; heterocycle; $C_{6-10}$aryl$C_{1-6}$alkylene; preferably each $R^{10}$ is independently $C_{1-6}$alkyl;

each $R^{11}$ is independently selected from hydroxyl, alkyl; aryl; heterocycle; arylalkylene; heterocycle-alkylene; preferably each $R^{11}$ is independently selected from hydroxyl; $C_{1-6}$alkyl; $C_{6-10}$aryl; heterocycle; $C_{6-10}$aryl$C_{1-6}$alkylene; preferably each $R^{11}$ is independently from hydroxyl or $C_{1-6}$alkyl;

each $R^{12}$ and $R^{13}$ is independently selected from hydrogen; alkyl; aryl; heterocycle; arylalkylene; heterocycle-alkylene; and wherein $R^{12}$ and $R^{13}$ can be taken together in order to form a 4-, 5-, or 6-, membered heterocycle; preferably each $R^{12}$ and $R^{13}$ is independently selected from hydrogen; alkyl; aryl; heterocycle; arylalkylene; preferably each $R^{12}$ and $R^{13}$ is independently selected from hydrogen; $C_{1-6}$alkyl; $C_{6-10}$aryl; heterocycle;

each $R^{20}$ is independently selected from alkyl; preferably each $R^{20}$ is independently selected from $C_{1-6}$alkyl; preferably each $R^{20}$ is independently selected from $C_{1-4}$alkyl;

each $R^{21}$ is independently selected from alkyl; preferably each $R^{21}$ is independently selected from $C_{1-6}$alkyl; preferably each $R^{21}$ is independently selected from $C_{1-4}$alkyl;

each $R^{22}$ and $R^{23}$ is independently selected from hydrogen; or alkyl; and wherein $R^{22}$ and $R^{23}$ can be taken together in order to form a 4-, 5-, or 6-, membered non-aromatic heterocycle; preferably each $R^{22}$ and $R^{23}$ is independently selected from hydrogen; or alkyl; preferably each $R^{22}$ and $R^{23}$ is independently selected from hydrogen; or $C_{1-6}$alkyl.

According to an embodiment, the present invention provides compounds of Formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), or (J4) or any subgroup thereof, wherein E is CR$^3$, each $R^1$, $R^4$ and $R^6$ is independently selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; $C_{1-6}$alkyl; $C_{6-10}$aryl; heterocycle; $C_{6-10}$aryl$C_{1-6}$alkylene; heterocycle-$C_{1-6}$alkylene;

$R^3$ is selected from hydrogen; halogen; —OH; —OR$^{10}$; —SH; trifluoromethyl; trifluoromethoxy; nitro; —NR$^{12}$R$^{13}$; -cyano; —COOH; —COOR$^{10}$; $C_{1-6}$alkyl; $C_{6-10}$aryl; heterocycle; $C_{6-10}$aryl$C_{1-6}$alkylene; heterocycle-$C_{1-6}$alkylene;

$R^2$ is selected from hydrogen; or $C_{1-6}$alkyl;

$R^5$ is selected from halogen; —OH; —OR$^{10}$; —SH; —SR$^{10}$; trifluoromethyl; trifluoromethoxy; nitro; —NR$^{12}$R$^{13}$; -cyano; —COOH; —COOR$^{10}$; —C(O)R$^{11}$; alkyl; aryl; heterocycle; arylalkylene; heterocycle-alkylene;

n is 1;

each of $Y^1$, $Y^2$, $Y^3$, $Y^4$ and $Y^5$ is independently selected from CZ$^1$; or N; wherein at least three of $Y^1$, $Y^2$, $Y^3$, $Y^4$ and $Y^5$ are selected from CZ$^1$;

B is selected from aryl; or heterocycle; preferably B is selected from $C_{6-10}$aryl; or heterocycle; B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, each $R^8$ is independently selected from hydrogen; halogen; alkyl; —OH; —OR$^{20}$; —SH; trifluoromethyl; trifluoromethoxy; nitro; -cyano;

each $Z^1$ is independently selected from hydrogen; $C_{1-6}$alkyl; and $Z^2$;

each $Z^2$ is independently selected from halogen; —OH; —OR$^{20}$; —SH; trifluoromethyl; trifluoromethoxy; —NR$^{22}$R$^{23}$; -cyano; —COOH; —COOR$^{20}$; and —C(O)R$^{21}$;

each $R^{10}$ is independently selected from $C_{1-6}$alkyl; $C_{6-10}$aryl; heterocycle; $C_{6-10}$aryl$C_{1-6}$alkylene;

each $R^{11}$ is independently selected from hydroxyl; $C_{1-6}$alkyl; $C_{6-10}$aryl; heterocycle; $C_{6-10}$aryl$C_{1-6}$alkylene;

each $R^{12}$ and $R^{13}$ is independently selected from hydrogen; alkyl; aryl; heterocycle; arylalkylene;

each $R^{20}$ is independently selected from $C_{1-6}$alkyl;

each $R^{21}$ is independently selected from $C_{1-6}$alkyl;

According to an embodiment, the present invention provides compounds of Formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), or (J4) or any subgroup thereof, wherein E is $CR^3$, each $R^1$, $R^4$ and $R^6$ is independently selected from hydrogen; halogen; —OH; —$OC_{1-4}$alkyl; trifluoromethyl; trifluoromethoxy; -cyano; $C_{1-4}$alkyl; $C_6$aryl; $C_6$aryl$C_{1-6}$alkylene;

$R^3$ is selected from hydrogen; halogen; —OH; —$OC_{1-4}$alkyl; trifluoromethyl; trifluoromethoxy; -cyano; $C_{1-4}$alkyl; $C_6$aryl; $C_6$aryl$C_{1-6}$alkylene;

$R^2$ is selected from hydrogen; or $C_{1-2}$alkyl;

$R^5$ is selected from halogen; —OH; —$OR^{10}$; —SH; —$SR^{10}$; trifluoromethyl; trifluoromethoxy; nitro; —$NR^{12}R^{13}$; -cyano; —COOH; —$COOR^{10}$; —$C(O)C_{1-6}$alkyl; $C_{1-6}$alkyl; $C_{6-10}$aryl; heterocycle; $C_{6-10}$aryl$C_{1-6}$alkylene;

n is 1;

each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$, with $Z^1$ being selected from hydrogen, alkyl or halogen;

B is selected from $C_{6-10}$aryl; heteroaryl or morpholinyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl or isatinoyl; preferably B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, each $R^8$ is independently selected from hydrogen; halogen; alkyl; —$OR^{20}$; trifluoromethyl; trifluoromethoxy; -cyano; wherein $R^{20}$ is alkyl;

each $Z^1$ is independently selected from hydrogen; $C_{1-6}$alkyl; and $Z^2$;

each $Z^2$ is independently selected from halogen; —OH; —$OC_{1-6}$alkyl; trifluoromethyl; trifluoromethoxy; -cyano;

each $R^{10}$ is independently $C_{1-6}$alkyl;

each $R^{12}$ and $R^{13}$ is independently selected from hydrogen; $C_{1-6}$alkyl; $C_{6-10}$aryl; heterocycle each $R^{20}$ is independently selected from $C_{1-4}$alkyl.

According to an embodiment, the present invention provides compounds of Formula (AA1), (A1), (A2), (A3), (B1), (B2), (B3), (C1), (C2), (C3), (F1), (F2), (F3), (F4), (F5), (G1), (G2), (G3), (G4), (G5), (G6), (G7), (G8), (H1), (H2), (H3), (H4), (I1), (I2), (I3), (I4), (J1), (J2), (J3), or (J4) or any subgroup thereof, wherein E is $CR^3$, each $R^1$, $R^4$ and $R^6$ is independently selected from hydrogen; fluoro; or chloro;

$R^3$ is selected from hydrogen; halogen; —OH; methoxy; trifluoromethyl; trifluoromethoxy; -cyano; $C_{1-4}$alkyl; $C_6$aryl;

$R^2$ is hydrogen;

$R^5$ is selected from halogen; -cyano; —OH; —$OR^{10}$; —SH; —$SR^{10}$; trifluoromethyl; trifluoromethoxy; —$C(O)C_{1-4}$alkyl; —$NR^{12}R^{13}$; $C_{1-6}$alkyl; phenyl; morpholinyl;

n is 1 each of $Y^1$, $Y^2$, $Y^3$, $Y^4$ and $Y^5$ is independently selected from $CZ^1$; or N; wherein at least three of $Y^1$, $Y^2$, $Y^3$, $Y^4$ and $Y^5$ are selected from $CZ^1$, with $Z^1$ being selected from hydrogen, or halogen;

B is selected from phenyl, pyridyl, dihydroypyridyl, piperidyl, thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, pyranyl, 2H-pyrrolyl, pyrazinyl, pyridazinyl, indolizinyl, isoindolyl, 3H-indolyl, 1H-indazoly, purinyl, pyrimidinyl; preferably B is selected from phenyl, pyridyl, piperidyl, furanyl, thienyl, pyrazolyl, imidazolyl, pyrrolidinyl; preferably B is selected from phenyl, furanyl, or thienyl;

m is 0, 1 or 2, preferably m is 0 or 1;

each $R^8$ is independently selected from hydrogen; halogen; $C_{1-4}$alkyl; —$OR^{20}$; trifluoromethyl; -cyano; wherein $R^{20}$ is $C_{1-2}$alkyl; preferably each $R^8$ is independently selected from hydrogen; fluoro; chloro; $C_{1-2}$alkyl; —$OCH_3$; trifluoromethyl; -cyano;

each $Z^1$ is independently selected from hydrogen; $C_{1-6}$alkyl; and $Z^2$;

each $Z^2$ is independently selected from fluoro; chloro; —OH; —$OC_{1-3}$alkyl; trifluoromethyl; trifluoromethoxy; -cyano;

each $R^{10}$ is independently $C_{1-6}$alkyl;

each $R^{12}$ and $R^{13}$ is independently selected from hydrogen; or $C_{1-6}$alkyl.

The present invention also encompasses a pharmaceutical composition comprising one or more pharmaceutically acceptable excipients and a therapeutically effective amount of a compound according to the formulae herein such as (AA1), (A1) or any subgroup or embodiment thereof or a stereoisomer, enantiomer or tautomer thereof.

The present invention also encompasses compounds of the formulae herein or any subgroup or embodiment thereof or a stereoisomer, enantiomer, tautomer, solvate, hydrate, salt or prodrug thereof for use as a medicine.

The present invention also encompasses compounds of formulae herein or of any subgroup or embodiment thereof or a stereoisomer, enantiomer, tautomer, solvate, hydrate, salt or prodrug thereof for use as a medicine for the prevention or treatment of neurodegenerative disorders.

In a particular embodiment, the invention provides the compounds described herein for use as a medicine for the prevention or treatment of neurodegenerative disorders, such as disorders collectively known as tauopathies, and disorders characterised by cytotoxic α-synuclein amyloidogenesis. The invention also provides for pharmaceutical compositions of the compounds described herein and methods for the treatment or prevention of neurodegenerative disorders.

The term "tauopathy" as used herein, unless otherwise stated, refers to a disease characterised by dysfunctioning of the TAU protein, for instance manifested by insoluble aggregates or polymers of said protein. Such diseases include, but are not limited to, Alzheimer's disease, Pick's disease, corticobasal degeneration, progressive supranuclear palsy, frontotemporal dementia and parkinsonism (linked to chromosome 17, FTDP-17).

The term "α-synucleopathy" as used herein, unless otherwise stated, refers to a disease characterised by the presence of pathological deposition of insoluble α-synuclein polymers or aggregates intracellularly and/or extracellularly. Such diseases include, but are not limited to, Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

The term "neurodegenerative disorders" as used herein, unless otherwise stated, refers to tauopathy and α-synucleopathy, and thereby includes, but is not limited to Alzheimer's disease, Pick's disease, corticobasal degeneration, progressive supranuclear palsy, frontotemporal dementia, parkinsonism (linked to chromosome 17, FTDP-17), Parkinson's disease, diffuse Lewy body disease, traumatic brain injury, amyotrophic lateral sclerosis, Niemann-Pick disease, Hallervorden-Spatz syndrome, Down syndrome, neuroaxonal dystrophy, and multiple system atrophy.

As used herein, the term "Parkinson's disease" refers to a chronic progressive nervous disease characterised by neurodegeneration, especially degeneration of dopaminergic neurons. Symptoms include stooped posture, resting tremor, weakness of resting muscles, a shuffling gait, speech impediments, movement difficulties and an eventual slowing of mental processes and dementia.

The term "Alzheimer's disease" as used herein, also called Alzheimer disease, Senile Dementia of the Alzheimer Type (SDAT) or simply Alzheimer's refers to a chronic progressive nervous disease characterised by neurodegeneration with as most important (early) symptom being memory loss. As the disease advances, symptoms include confusion, irritability and aggression, mood swings, language breakdown, long-term memory loss, and the general withdrawal of the sufferer as their senses decline.

The term "neuroprotective" agent, as used herein, refers to drugs or chemical agents intended to prevent neurodegeneration, including drugs that slow down or stop the progression of neuronal degeneration.

The present invention relates to a group of novel compounds which have desirable biological properties such as an inhibitory effect on TAU-instigated cytotoxicity. Based on this inhibitory activity, and the fact that these compounds are not toxic to neural cells, these derivatives are useful in the manufacture of a medicament for the prevention and/or treatment of a tauopathy. The novel compounds have a structure according to formulae and embodiments thereof as described herein.

The term "pharmaceutically acceptable carrier" or "pharmaceutically acceptable excipient" as used herein in relation to pharmaceutical compositions and combined preparations means any material or substance with which the active principle may be formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, pellets or powders.

Suitable pharmaceutical carriers for use in the said pharmaceutical compositions and their formulation are well known to those skilled in the art. There is no particular restriction to their selection within the present invention although, due to the usually low or very low water-solubility of the derivatives of this invention, special attention will be paid to the selection of suitable carrier combinations that can assist in properly formulating them in view of the expected time release profile. Suitable pharmaceutical carriers include additives such as wetting agents, dispersing agents, stickers, adhesives, emulsifying or surface-active agents, thickening agents, complexing agents, gelling agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals.

The pharmaceutical compositions of the present invention may be prepared in any known manner, for instance by homogeneously mixing, dissolving, spray-drying, coating and/or grinding the active ingredients, in a one-step or a multi-steps procedure, with the selected carrier material and, where appropriate, the other additives such as surface-active agents. may also be prepared by micronisation, for instance in view to obtain them in the form of microspheres usually having a diameter of about 1 to 10 μm, namely for the manufacture of microcapsules for controlled or sustained release of the biologically active ingredient(s).

Methods of preparing various pharmaceutical compositions with a certain amount of active ingredient are known, or will be apparent in light of this disclosure, to those skilled in this art. For examples of methods of preparing pharmaceutical compositions, see (*Remington; The Science and Practice of Pharmacy*, Lippincott Williams & Wilkins, 21st Ed, 2005).

Therapeutically effective doses of the compounds of the present invention required to prevent or to treat the medical condition are readily ascertained by one of ordinary skill in the art using preclinical and clinical approaches familiar to the medicinal arts. The dose of the compound or a pharmaceutically acceptable salts thereof to be administered depends on the individual case and, as customary, is to be adapted to the conditions of the individual case for an optimum effect. Thus it depends, of course, on the frequency of administration and on the potency and duration of action of the compound employed in each case for therapy or prophylaxis, but also on the nature and severity of the disease and symptoms, and on the sex, age, weight co-medication and individual responsiveness of the subject to be treated and on whether the therapy is acute or prophylactic. The percentage of drug present in the formulation is also a factor. Doses may be adapted in function of weight and for pediatric applications. In the case of oral administration the dosage for adults can vary from about 0.01 mg to about 4000 mg per day, preferably from about 0.1 mg to about 2000 mg per day, more preferably from about 0.5 mg to about 1000 mg per day, of a compound of the invention or of the corresponding amount of a pharmaceutically acceptable salt thereof. The daily dosage may be administered as single dose or in divided doses and, in addition, the upper limit can also be exceeded when this is found to be indicated.

The novel compounds of the invention can be prepared by the following methods which are exemplified further in the examples.

The compounds of the invention can be prepared while using a series of chemical reactions well known to those skilled in the art, altogether making up the process for preparing said compounds and exemplified further. The processes described further are only meant as examples and by no means are meant to limit the scope of the present invention.

The compounds of the present invention can be prepared according to the following general procedures:

Scheme 1:

by procedures known to the skilled in the art or as set forth in the examples below), by procedures known to the skilled in the art or as set forth in the examples below provides compounds of formula III. In a similar manner, condensation of intermediates of formula I with intermediates of formula IV (commercially available or synthesized by procedures known to the skilled in the art or as set forth in the examples below), by procedures known to the skilled in the art or as set forth in the examples below, provides intermediates of formula VI, which can be subsequently converted in compounds of formula II with a suitable precursor of intermediate of formula V by procedures known to the skilled in the art or as set forth in the examples below.

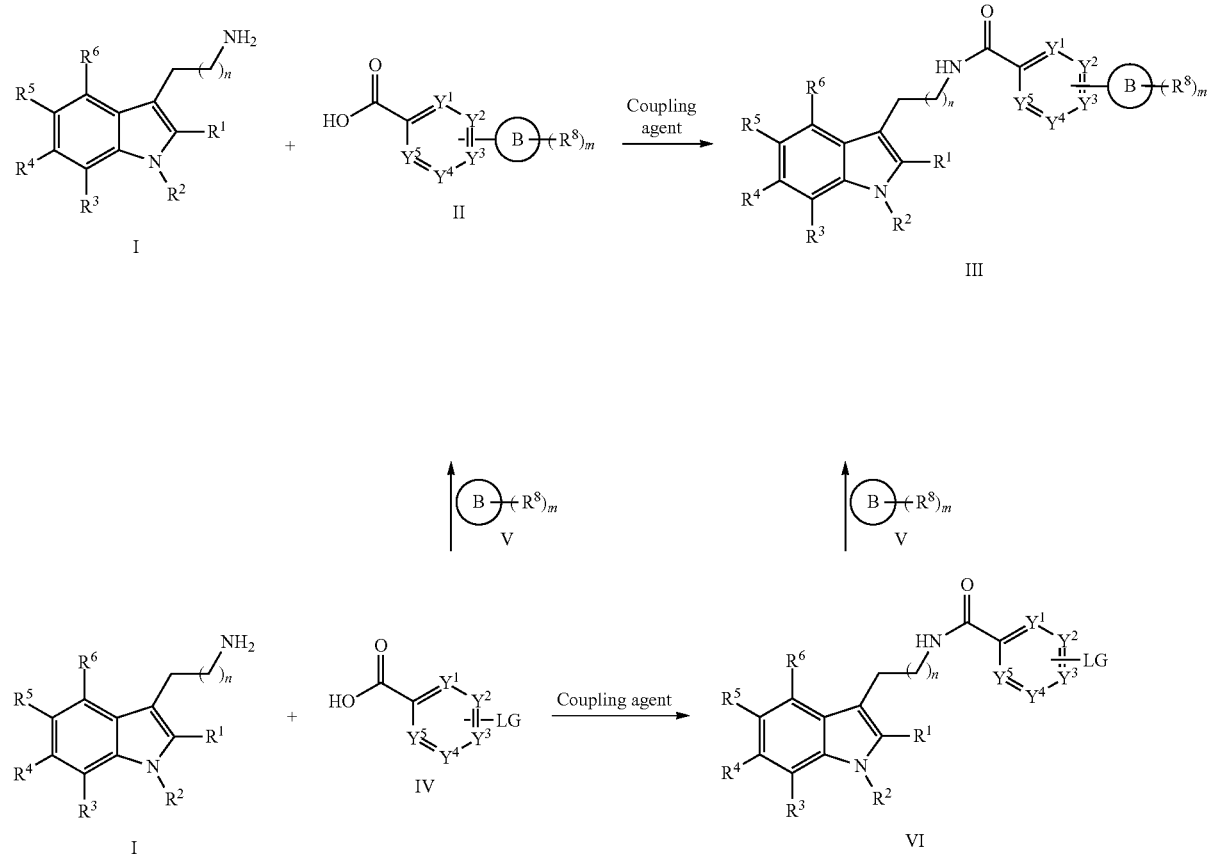

Scheme 1: all $R^1, R^2, R^3, R^4, R^5, R^6, R^8, Y^1, Y^2, Y^3, Y^4, Y^5, B$, n, m and LG are as described for the compounds of the present invention and its embodiments and formulae.

Intermediates of formula I are commercially available or synthesized by procedures known to the skilled in the art or as set forth in the examples below. More detailed information can be found in the following references (e.g., Journal of Fluorine Chemistry, 127(9), 1256-1260, 2006; Medicinal Chemistry, 3(6), 561-571, 2007; WO 2006007542; J. Org. Chem., 71(18), 7028-7034, 2006; Organic Letters, 4(16), 2613-2615, 2002; Tetrahedron Letters, 43(5), 787-790, 2002; Synlett, 8, 1311-1315, 2005; Journal of the American Chemical Society, 130(12), 3853-3865, 2008; Journal of Medicinal Chemistry, 49(21), 6408-6411, 2006; Journal of Medicinal Chemistry, 47(15), 3823-3842, 2004).

Condensation of intermediates of formula I with intermediates of formula II (commercially available or synthesized The strategy outlined in scheme 1 can be applied for the synthesis of any aromatic 6 membered ring systems (e.g., benzene, pyridine, pyrimidine, pyridazine, pyrazine) and is not limited to these examples.

The resulting compounds may be optionally converted into a pharmaceutically acceptable salt or vice versa according to the methods known by the skilled in the art.

Further, the resulting compounds may be converted into each other following art-known functional group transformation reactions. For example, amino groups may be N-alkylated, nitro groups reduced to amino groups, a halo atom may be exchanged for another halo.

Another aspect of the present invention therefore provides intermediates of formula VI

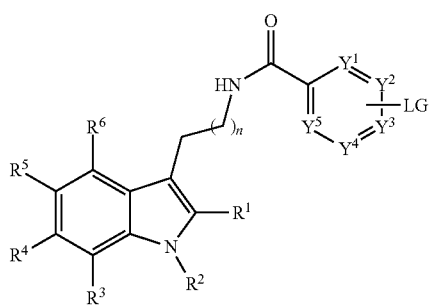

(VI)

wherein $R^1$, $R^2$, $R^3$, $R^4$, $R^5$, $R^6$, $Y^1$, $Y^2$, $Y^3$, $Y^4$, $Y^5$, n, and LG are each as defined herein, and the isomers (in particular stereoisomers, enantiomers or tautomers), solvates, hydrates, or salts thereof.

Another aspect of the present invention relates to a method of preparing new intermediates of formula VI, as depicted above, wherein $R^1$, $R^2$, $R^3$, $R^4$, $R^5$, $R^6$, $Y^1$, $Y^2$, $Y^3$, $Y^4$, $Y^5$, n, and LG are each as defined herein, and the isomers (in particular stereoisomers, enantiomers or tautomers), solvates, hydrates, or salts thereof; by condensation of intermediates of formula I with intermediates of formula IV (commercially available or synthesized by procedures known to the skilled in the art or as set forth in the examples below), by procedures known to the skilled in the art or as set forth in the examples below.

EXAMPLES

The following examples are provided for the purpose of illustrating the present invention and by no means should be interpreted to limit the scope of the present invention.

Part A represents the preparation of the compounds (intermediates and final compounds) whereas Part B represents the pharmacological examples.

All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a X-Bridge Prep C18, 100×19 mm, 5 μm column equipped with a X-Bridge C18, 5 μm, 19×10 mm Guard column.

Elutions were carried out with the methods described in the following tables, and detection wavelengths were fixed at 210 and 254 nm.

Solvent A: Ammonium Acetate puriss p.a. for HPLC 10 mM in milliQ water, adjusted at pH10 with ammonium hydroxide puriss p.a. for HPLC.

Solvent B: acetonitrile HPLC grade.

HPLC Method 1

| Time (min) | Flow Rate ml/min | Solvent A % | Solvent B % |
|---|---|---|---|
| 0 | 20 | 60 | 40 |
| 2.00 | 20 | 60 | 40 |
| 7.00 | 20 | 20 | 80 |
| 7.10 | 20 | 10 | 90 |
| 10.00 | 20 | 10 | 90 |
| 10.50 | 20 | 60 | 40 |
| 16.00 | 20 | 60 | 40 |

HPLC Method 2

| Time (min) | Flow Rate ml/min | Solvent A % | Solvent B % |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Exemplary compounds of the present invention are shown in table 1.

TABLE 1

| CODE | STRUCTURE |
|---|---|
| Cpd001 | (structure of 5-methoxy indole ethylamine linked to biphenyl carboxamide) |
| Cpd002 | (structure of 5-chloro indole ethylamine linked to biphenyl carboxamide) |

TABLE 1-continued

| CODE | STRUCTURE |
|------|-----------|
| Cpd003 | 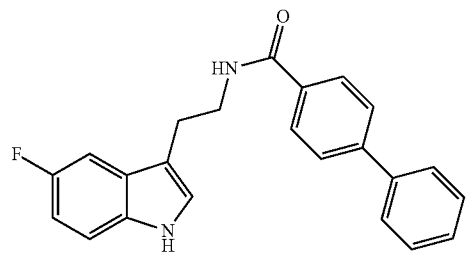 [SMILES: O=C(NCCc1c[nH]c2ccc(F)cc12)c1ccc(-c2ccccc2)cc1] |
| Cpd004 | 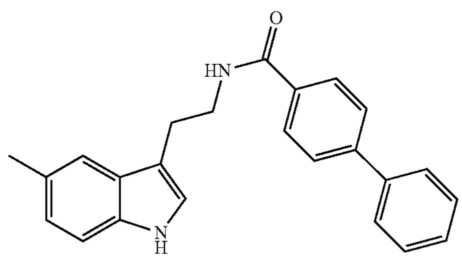 [SMILES: Cc1ccc2[nH]cc(CCNC(=O)c3ccc(-c4ccccc4)cc3)c2c1] |
| Cpd005 | 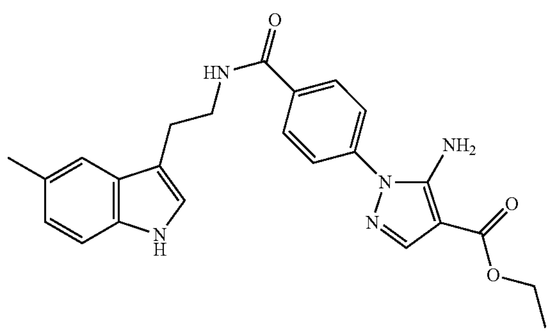 [SMILES: CCOC(=O)c1cnn(-c2ccc(C(=O)NCCc3c[nH]c4ccc(C)cc34)cc2)c1N] |
| Cpd006 | 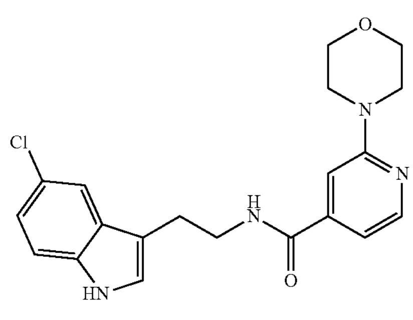 [SMILES: O=C(NCCc1c[nH]c2ccc(Cl)cc12)c1ccnc(N2CCOCC2)c1] |
| Cpd007 | 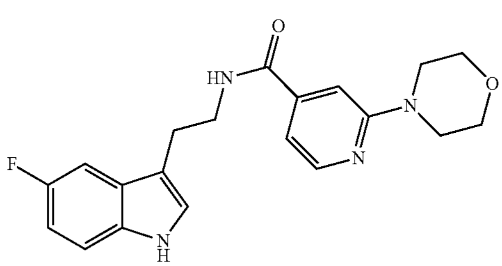 [SMILES: O=C(NCCc1c[nH]c2ccc(F)cc12)c1ccnc(N2CCOCC2)c1] |

TABLE 1-continued

| CODE | STRUCTURE |
|---|---|
| Cpd008 | 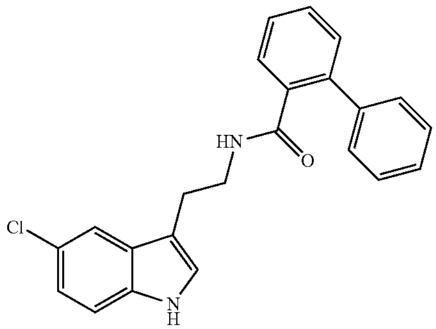 [SMILES: O=C(NCCc1c[nH]c2ccc(Cl)cc12)c1ccccc1-c1ccccc1] |
| Cpd009 | 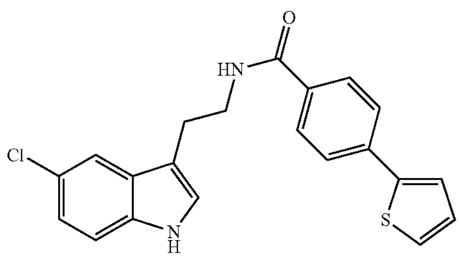 |
| Cpd010 | 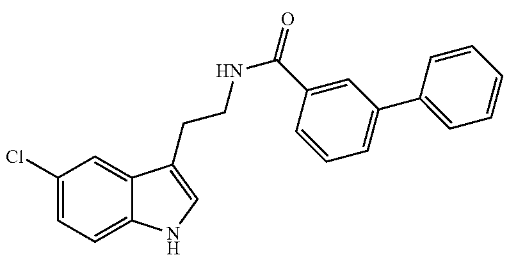 [SMILES: O=C(NCCc1c[nH]c2ccc(Cl)cc12)c1cccc(-c2ccccc2)c1] |
| Cpd011 | 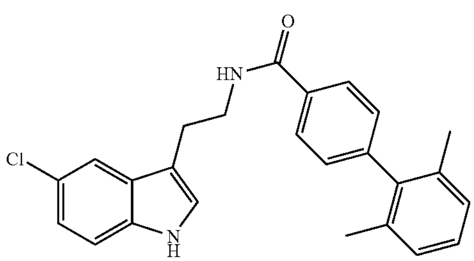 [SMILES: Cc1cccc(C)c1-c1ccc(C(=O)NCCc2c[nH]c3ccc(Cl)cc23)cc1] |
| Cpd012 | 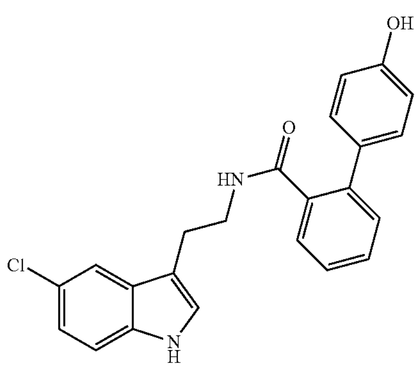 [SMILES: O=C(NCCc1c[nH]c2ccc(Cl)cc12)c1ccccc1-c1ccc(O)cc1] |

TABLE 1-continued

| CODE | STRUCTURE |
|---|---|
| Cpd013 | 5-chloro-tryptamine-NH-C(O)-(3-phenyl)-4'-hydroxybiphenyl |
| Cpd014 | 5-chloro-tryptamine-NH-C(O)-(4-phenyl)-4'-hydroxybiphenyl |
| Cpd015 | 5-chloro-tryptamine-NH-C(O)-(2-phenyl)-2'-methylbiphenyl |
| Cpd016 | 5-chloro-tryptamine-NH-C(O)-(3-phenyl)-2'-methylbiphenyl |
| Cpd017 | 5-chloro-tryptamine-NH-C(O)-(4-phenyl)-2'-methylbiphenyl |

TABLE 1-continued
| CODE | STRUCTURE |
|---|---|
| Cpd018 | 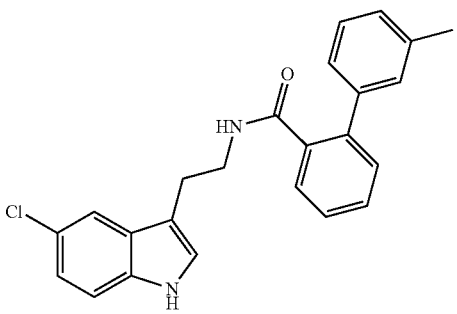 [SMILES: Cc1cccc(-c2ccccc2C(=O)NCCc2c[nH]c3ccc(Cl)cc23)c1] |
| Cpd019 | 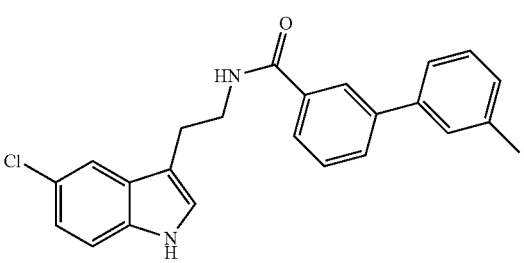 [SMILES: Cc1cccc(-c2cccc(C(=O)NCCc3c[nH]c4ccc(Cl)cc34)c2)c1] |
| Cpd020 | 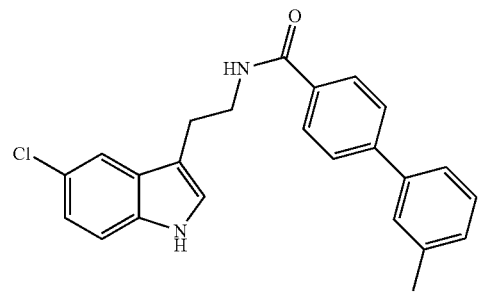 [SMILES: Cc1cccc(-c2ccc(C(=O)NCCc3c[nH]c4ccc(Cl)cc34)cc2)c1] |
| Cpd021 | 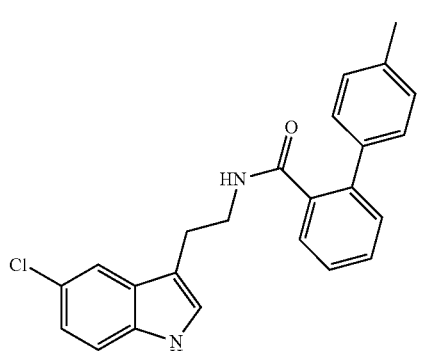 |
| Cpd022 | 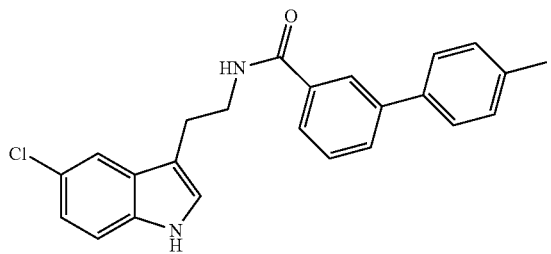 [SMILES: Cc1ccc(-c2cccc(C(=O)NCCc3c[nH]c4ccc(Cl)cc34)c2)cc1] |

TABLE 1-continued
| CODE | STRUCTURE |
| --- | --- |
| Cpd023 | 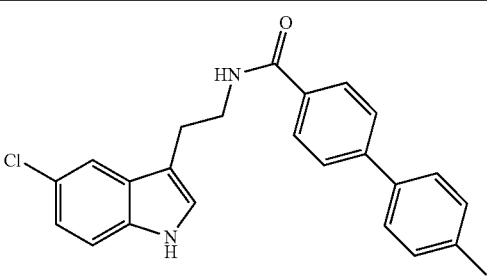 |
| Cpd024 | 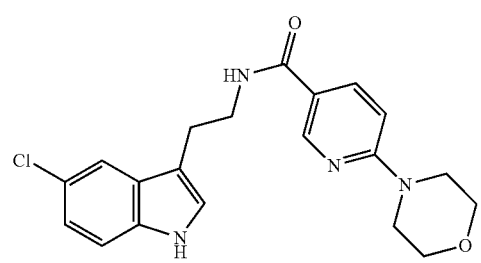 [SMILES: O=C(NCCc1c[nH]c2ccc(Cl)cc12)c1ccc(N2CCOCC2)nc1] |
| Cpd025 | 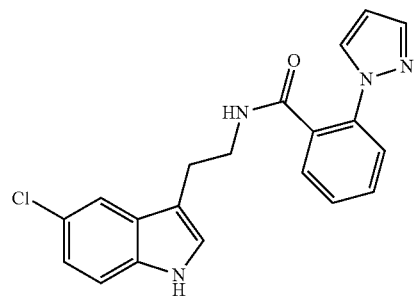 [SMILES: O=C(NCCc1c[nH]c2ccc(Cl)cc12)c1ccccc1-n1cccn1] |
| Cpd026 | 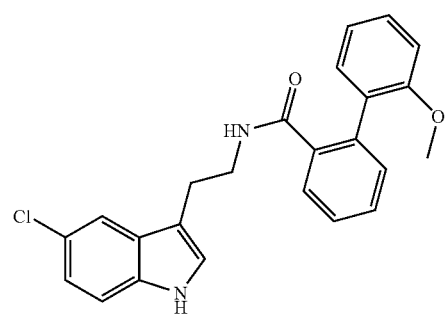 [SMILES: COc1ccccc1-c1ccccc1C(=O)NCCc1c[nH]c2ccc(Cl)cc12] |
| Cpd027 | 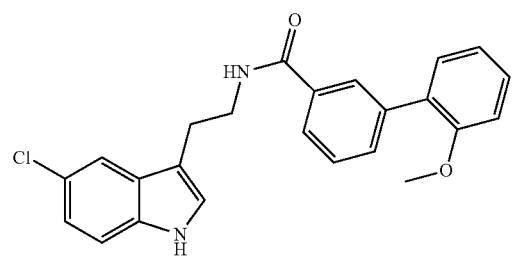 [SMILES: COc1ccccc1-c1cccc(C(=O)NCCc2c[nH]c3ccc(Cl)cc23)c1] |

TABLE 1-continued
| CODE | STRUCTURE |
|------|-----------|
| Cpd028 | 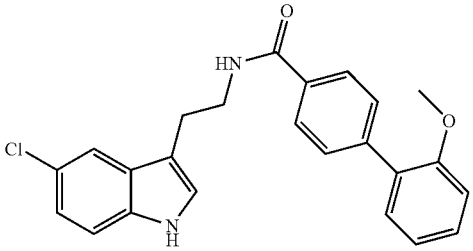 [SMILES: COc1ccccc1-c1ccc(C(=O)NCCc2c[nH]c3ccc(Cl)cc23)cc1] |
| Cpd029 | 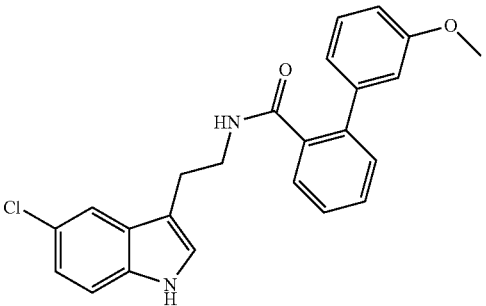 [SMILES: COc1cccc(-c2ccccc2C(=O)NCCc2c[nH]c3ccc(Cl)cc23)c1] |
| Cpd030 | 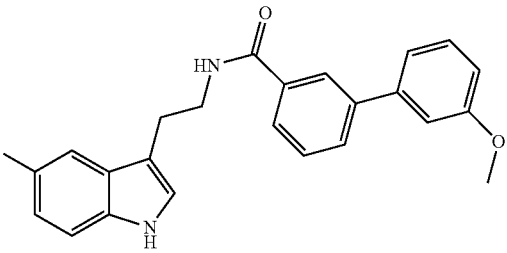 |
| Cpd031 | 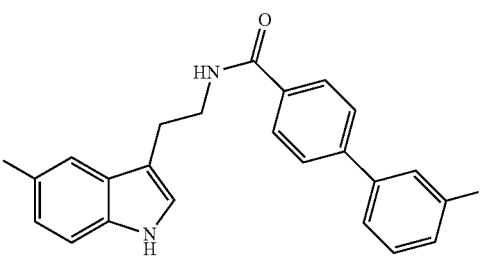 |
| Cpd032 | 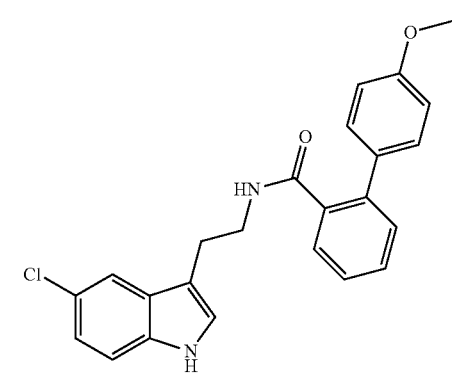 [SMILES: COc1ccc(-c2ccccc2C(=O)NCCc2c[nH]c3ccc(Cl)cc23)cc1] |

TABLE 1-continued
| CODE | STRUCTURE |
|---|---|
| Cpd033 | 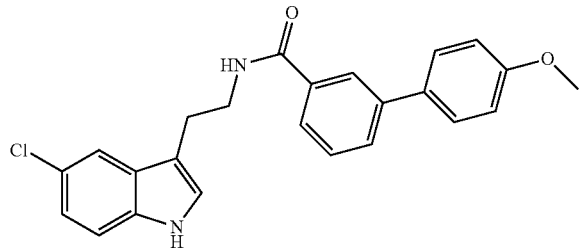 [SMILES: COc1ccc(-c2cccc(C(=O)NCCc3c[nH]c4ccc(Cl)cc34)c2)cc1] |
| Cpd034 | 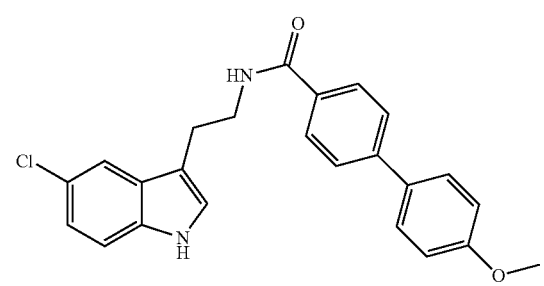 [SMILES: COc1ccc(-c2ccc(C(=O)NCCc3c[nH]c4ccc(Cl)cc34)cc2)cc1] |
| Cpd035 | 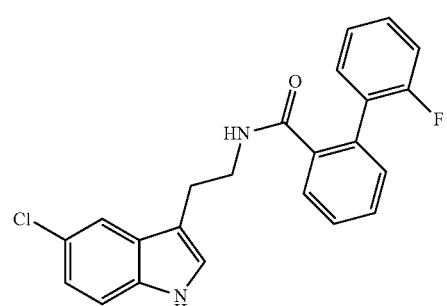 |
| Cpd036 | 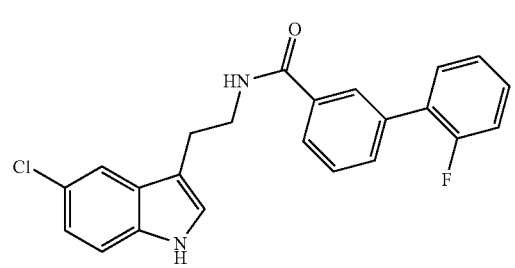 [SMILES: O=C(NCCc1c[nH]c2ccc(Cl)cc12)c1cccc(-c2ccccc2F)c1] |
| Cpd037 | 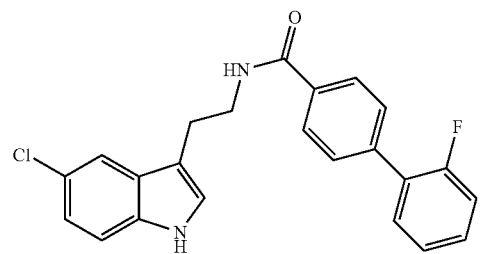 [SMILES: O=C(NCCc1c[nH]c2ccc(Cl)cc12)c1ccc(-c2ccccc2F)cc1] |

TABLE 1-continued

| CODE | STRUCTURE |
|---|---|
| Cpd038 | 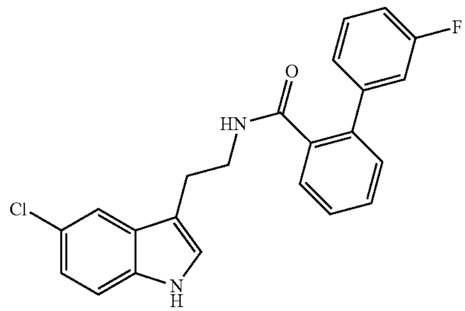 [SMILES: O=C(NCCc1c[nH]c2ccc(Cl)cc12)c1ccccc1-c1cccc(F)c1] |
| Cpd039 | 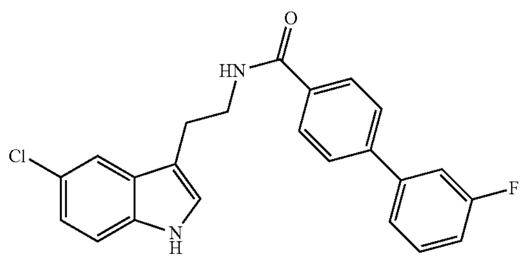 [SMILES: O=C(NCCc1c[nH]c2ccc(Cl)cc12)c1ccc(-c2cccc(F)c2)cc1] |
| Cpd040 | 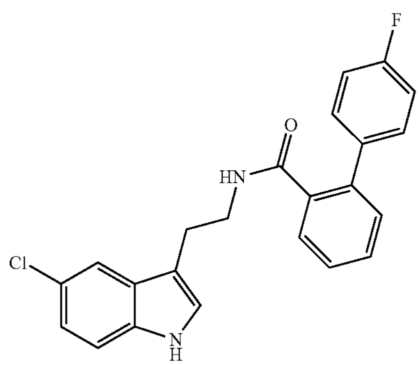 [SMILES: O=C(NCCc1c[nH]c2ccc(Cl)cc12)c1ccccc1-c1ccc(F)cc1] |
| Cpd041 | 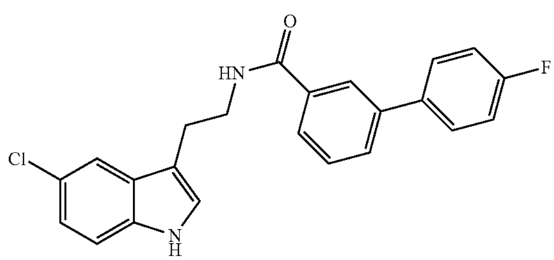 [SMILES: O=C(NCCc1c[nH]c2ccc(Cl)cc12)c1cccc(-c2ccc(F)cc2)c1] |
| Cpd042 | 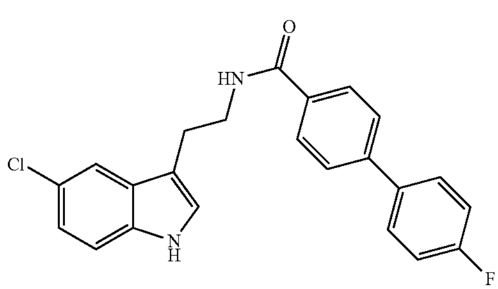 [SMILES: O=C(NCCc1c[nH]c2ccc(Cl)cc12)c1ccc(-c2ccc(F)cc2)cc1] |

TABLE 1-continued
| CODE | STRUCTURE |
|---|---|
| Cpd043 | 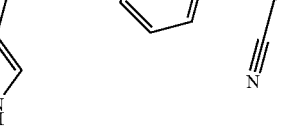 |
| Cpd044 | 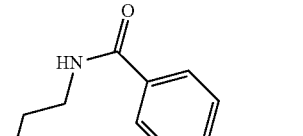 |
| Cpd045 | 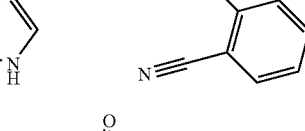 |
| Cpd046 | 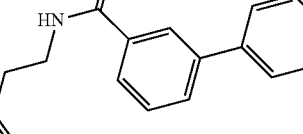 |
| Cpd047 | 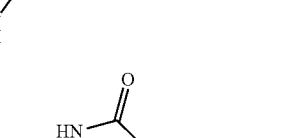 |
| Cpd048 | 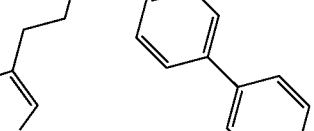 |

TABLE 1-continued

| CODE | STRUCTURE |
|---|---|
| Cpd049 | 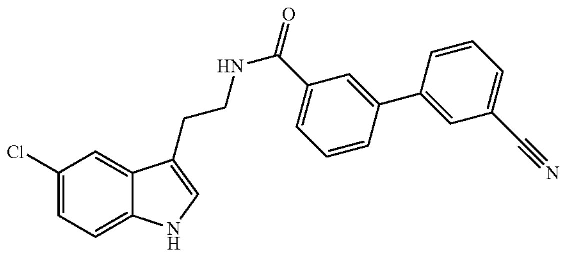 [SMILES: N#Cc1cccc(-c2cccc(C(=O)NCCc3c[nH]c4ccc(Cl)cc34)c2)c1] |
| Cpd050 | 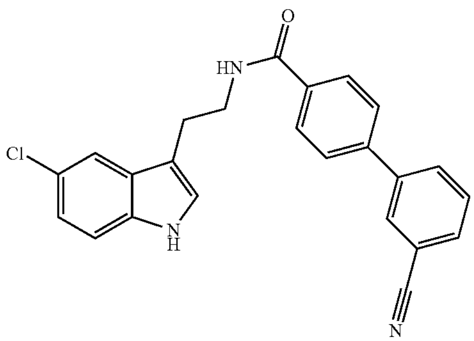 [SMILES: N#Cc1cccc(-c2ccc(C(=O)NCCc3c[nH]c4ccc(Cl)cc34)cc2)c1] |
| Cpd051 | 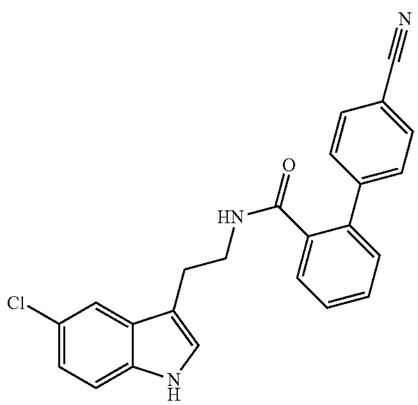 [SMILES: N#Cc1ccc(-c2ccccc2C(=O)NCCc2c[nH]c3ccc(Cl)cc23)cc1] |
| Cpd052 | 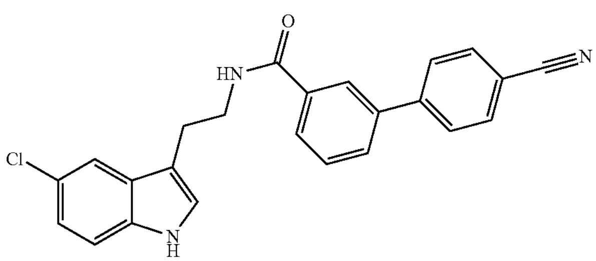 [SMILES: N#Cc1ccc(-c2cccc(C(=O)NCCc3c[nH]c4ccc(Cl)cc34)c2)cc1] |
| Cpd053 | 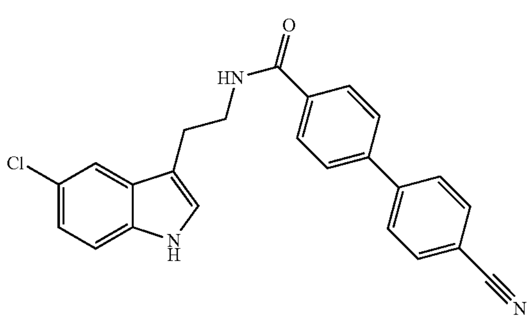 [SMILES: N#Cc1ccc(-c2ccc(C(=O)NCCc3c[nH]c4ccc(Cl)cc34)cc2)cc1] |

TABLE 1-continued

| CODE | STRUCTURE |
|---|---|
| Cpd054 | 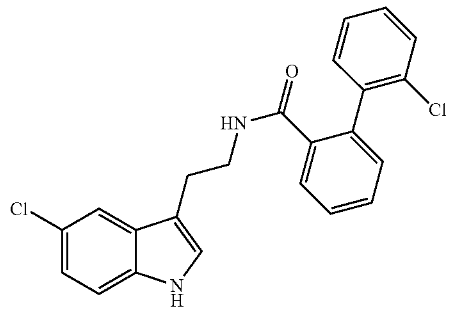 [SMILES: O=C(NCCc1c[nH]c2ccc(Cl)cc12)c1ccccc1-c1ccccc1Cl] |
| Cpd055 | 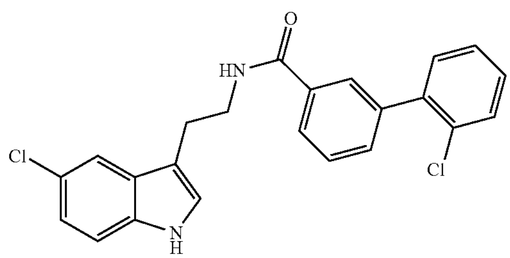 |
| Cpd056 | 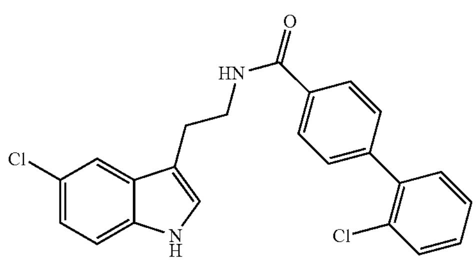 |
| Cpd057 | 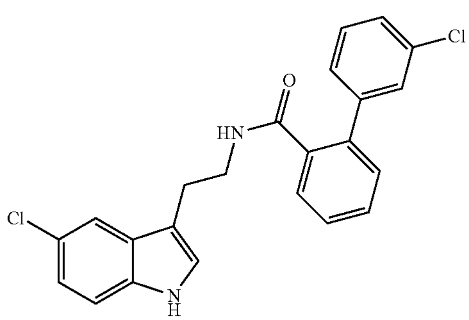 [SMILES: O=C(NCCc1c[nH]c2ccc(Cl)cc12)c1ccccc1-c1cccc(Cl)c1] |
| Cpd058 | 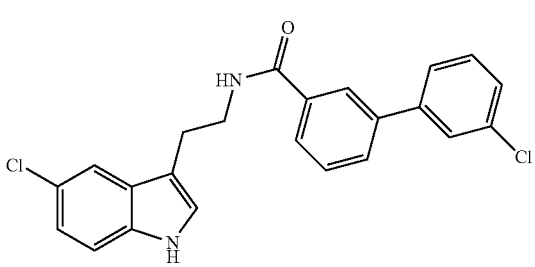 [SMILES: O=C(NCCc1c[nH]c2ccc(Cl)cc12)c1cccc(-c2cccc(Cl)c2)c1] |

TABLE 1-continued

| CODE | STRUCTURE |
| --- | --- |
| Cpd059 | 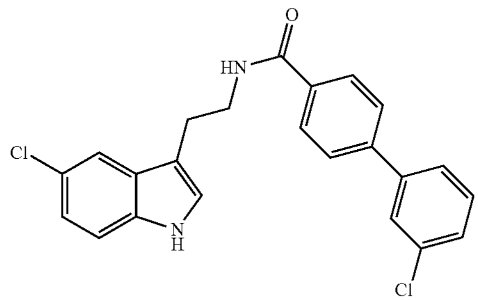 [SMILES: O=C(NCCc1c[nH]c2ccc(Cl)cc12)c1ccc(-c2cccc(Cl)c2)cc1] |
| Cpd060 | 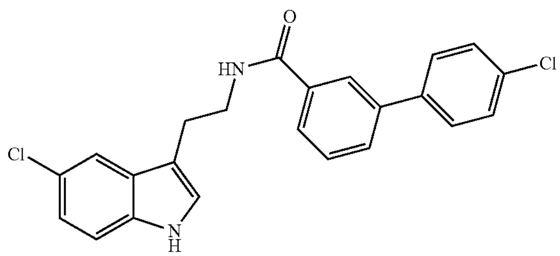 [SMILES: O=C(NCCc1c[nH]c2ccc(Cl)cc12)c1cccc(-c2ccc(Cl)cc2)c1] |
| Cpd061 | 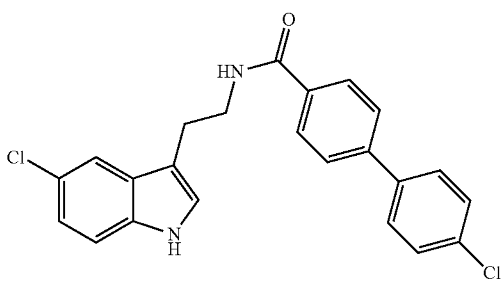 [SMILES: O=C(NCCc1c[nH]c2ccc(Cl)cc12)c1ccc(-c2ccc(Cl)cc2)cc1] |
| Cpd062 | 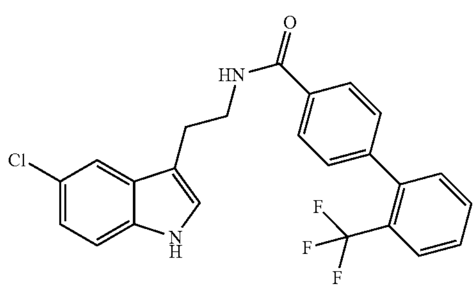 [SMILES: O=C(NCCc1c[nH]c2ccc(Cl)cc12)c1ccc(-c2ccccc2C(F)(F)F)cc1] |
| Cpd063 | 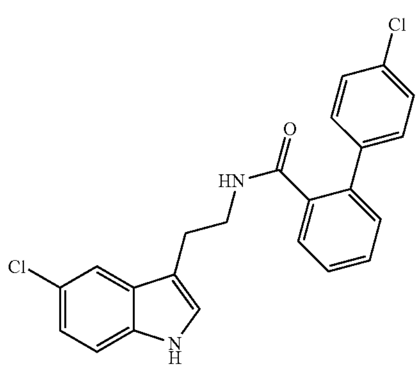 [SMILES: O=C(NCCc1c[nH]c2ccc(Cl)cc12)c1ccccc1-c1ccc(Cl)cc1] |

TABLE 1-continued

| CODE | STRUCTURE |
|---|---|
| Cpd064 | 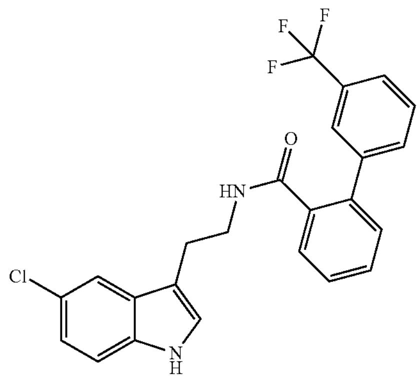 [SMILES: O=C(NCCc1c[nH]c2ccc(Cl)cc12)c1ccccc1-c1cccc(C(F)(F)F)c1] |
| Cpd065 | 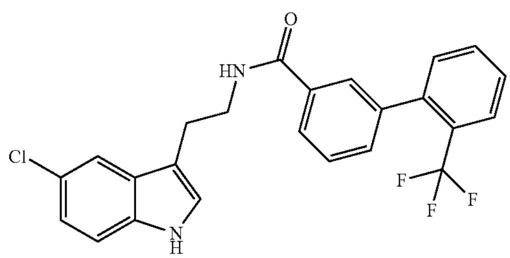 [SMILES: O=C(NCCc1c[nH]c2ccc(Cl)cc12)c1cccc(-c2ccccc2C(F)(F)F)c1] |
| Cpd066 | 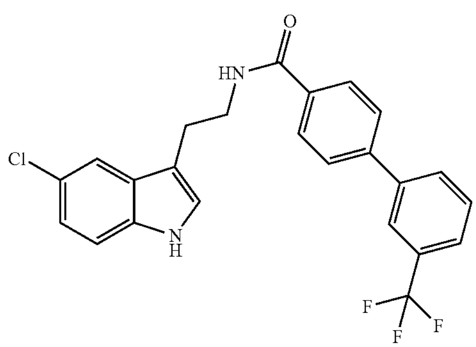 [SMILES: O=C(NCCc1c[nH]c2ccc(Cl)cc12)c1ccc(-c2cccc(C(F)(F)F)c2)cc1] |
| Cpd067 | 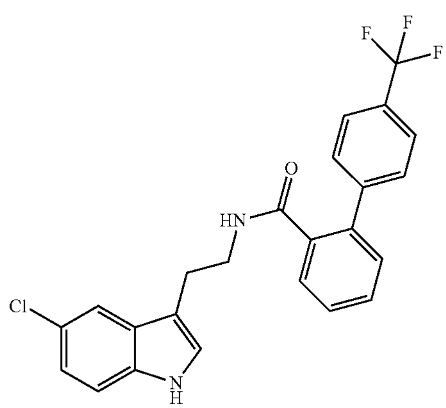 [SMILES: O=C(NCCc1c[nH]c2ccc(Cl)cc12)c1ccccc1-c1ccc(C(F)(F)F)cc1] |

TABLE 1-continued
| CODE | STRUCTURE |
|---|---|
| Cpd068 | 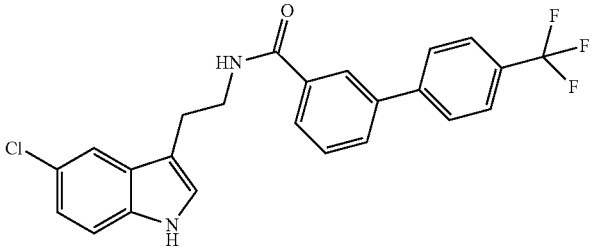 [SMILES: O=C(NCCc1c[nH]c2ccc(Cl)cc12)c1cccc(-c2ccc(C(F)(F)F)cc2)c1] |
| Cpd069 | 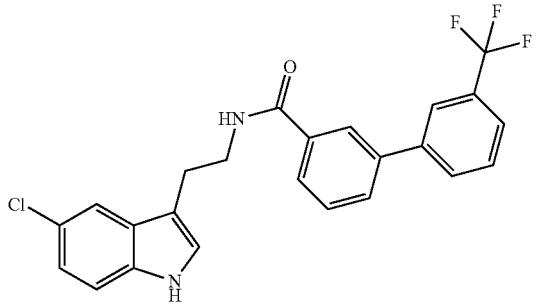 [SMILES: O=C(NCCc1c[nH]c2ccc(Cl)cc12)c1cccc(-c2cccc(C(F)(F)F)c2)c1] |
| Cpd070 | 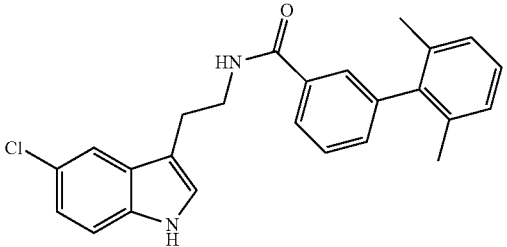 [SMILES: Cc1cccc(C)c1-c1cccc(C(=O)NCCc2c[nH]c3ccc(Cl)cc23)c1] |
| Cpd071 | 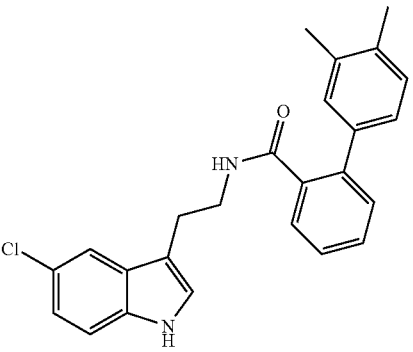 [SMILES: Cc1ccc(-c2ccccc2C(=O)NCCc2c[nH]c3ccc(Cl)cc23)cc1C] |
| Cpd072 | 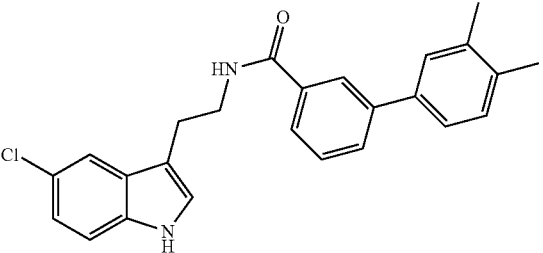 [SMILES: Cc1ccc(-c2cccc(C(=O)NCCc3c[nH]c4ccc(Cl)cc34)c2)cc1C] |

TABLE 1-continued
| CODE | STRUCTURE |
|---|---|
| Cpd073 | 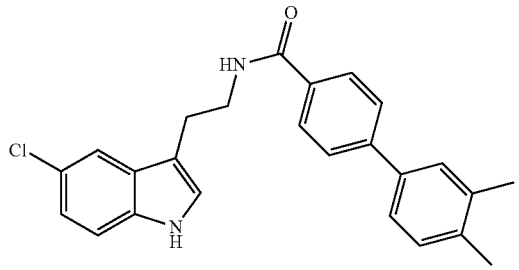 [SMILES: Cc1ccc(-c2ccc(C(=O)NCCc3c[nH]c4ccc(Cl)cc34)cc2)cc1C] |
| Cpd074 | 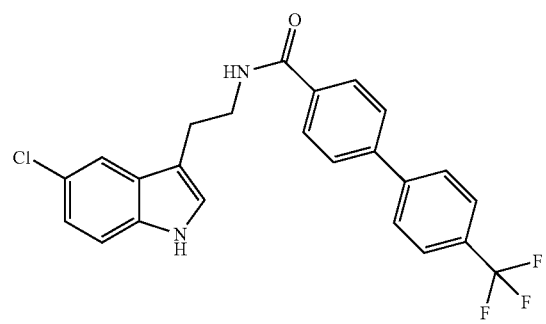 [SMILES: O=C(NCCc1c[nH]c2ccc(Cl)cc12)c1ccc(-c2ccc(C(F)(F)F)cc2)cc1] |
| Cpd075 | 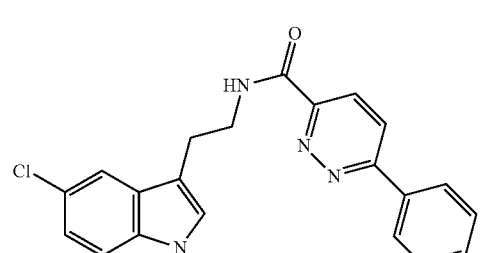 |
| Cpd076 | 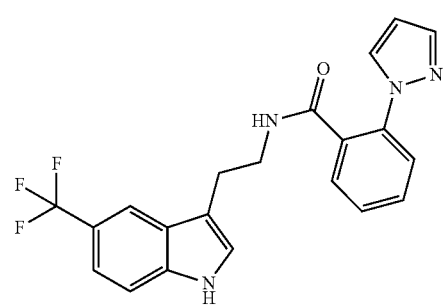 [SMILES: O=C(NCCc1c[nH]c2ccc(C(F)(F)F)cc12)c1ccccc1-n1cccn1] |
| Cpd077 | 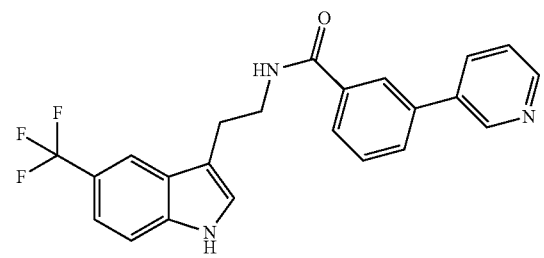 [SMILES: O=C(NCCc1c[nH]c2ccc(C(F)(F)F)cc12)c1cccc(-c2cccnc2)c1] |

TABLE 1-continued
| CODE | STRUCTURE |
|------|-----------|
| Cpd078 | 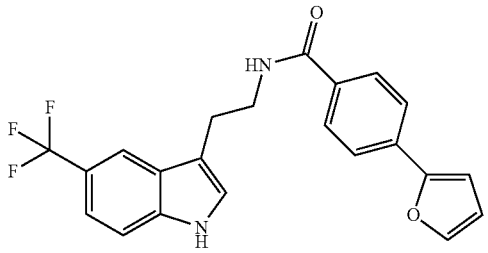 [SMILES: O=C(NCCc1c[nH]c2ccc(C(F)(F)F)cc12)c1ccc(-c2ccco2)cc1] |
| Cpd079 | 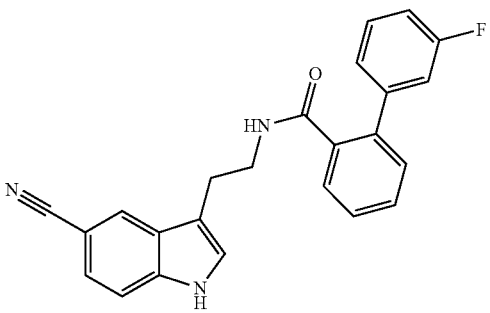 [SMILES: N#Cc1ccc2[nH]cc(CCNC(=O)c3ccccc3-c3cccc(F)c3)c2c1] |
| Cpd080 | 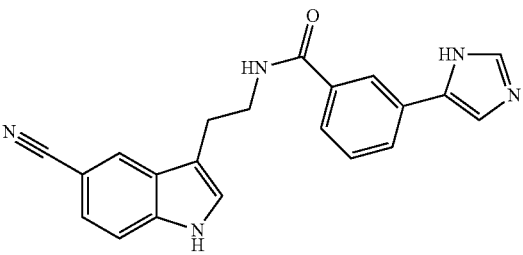 [SMILES: N#Cc1ccc2[nH]cc(CCNC(=O)c3cccc(-c4cnc[nH]4)c3)c2c1] |
| Cpd081 | 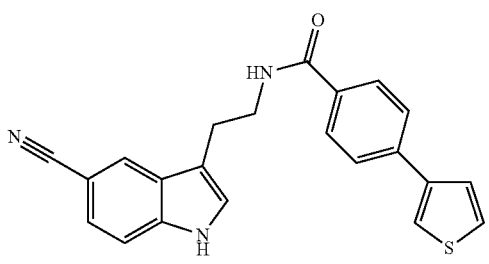 [SMILES: N#Cc1ccc2[nH]cc(CCNC(=O)c3ccc(-c4ccsc4)cc3)c2c1] |
| Cpd082 | 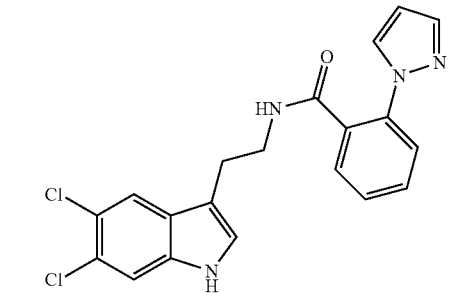 [SMILES: O=C(NCCc1c[nH]c2cc(Cl)c(Cl)cc12)c1ccccc1-n1cccn1] |

TABLE 1-continued

| CODE | STRUCTURE |
|---|---|
| Cpd083 | 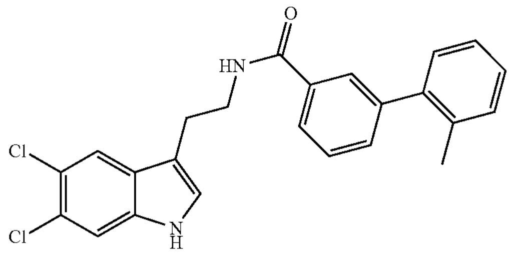 [SMILES: Cc1ccccc1-c1cccc(C(=O)NCCc2c[nH]c3cc(Cl)c(Cl)cc23)c1] |
| Cpd084 | 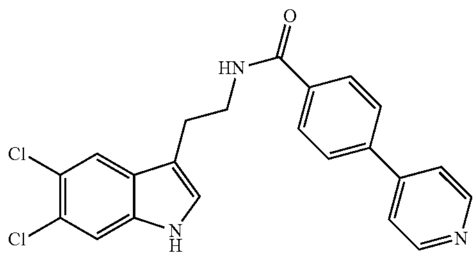 [SMILES: O=C(NCCc1c[nH]c2cc(Cl)c(Cl)cc12)c1ccc(-c2ccncc2)cc1] |
| Cpd085 | 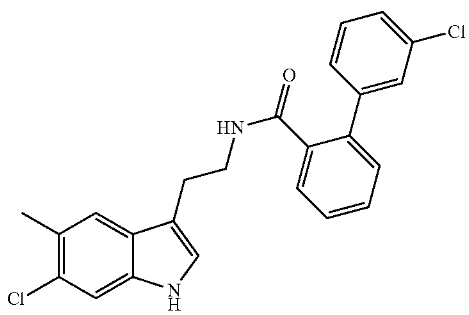 [SMILES: Cc1cc2c(CCNC(=O)c3ccccc3-c3cccc(Cl)c3)c[nH]c2cc1Cl] |
| Cpd086 | 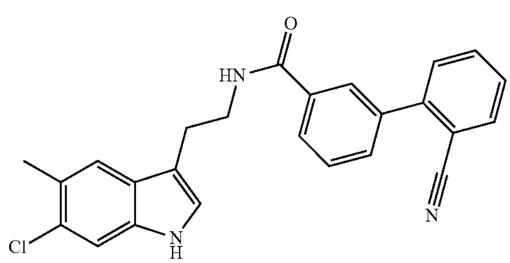 [SMILES: Cc1cc2c(CCNC(=O)c3cccc(-c4ccccc4C#N)c3)c[nH]c2cc1Cl] |
| Cpd087 | 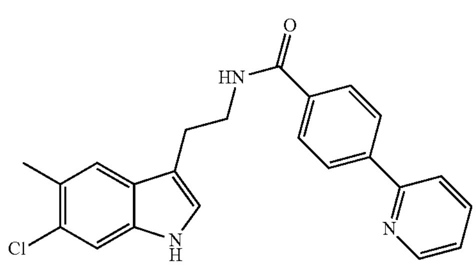 [SMILES: Cc1cc2c(CCNC(=O)c3ccc(-c4ccccn4)cc3)c[nH]c2cc1Cl] |

TABLE 1-continued
| CODE | STRUCTURE |
|---|---|
| Cpd088 | 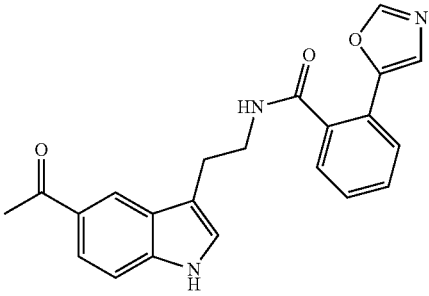 [SMILES: CC(=O)c1ccc2[nH]cc(CCNC(=O)c3ccccc3-c3cnco3)c2c1] |
| Cpd089 | 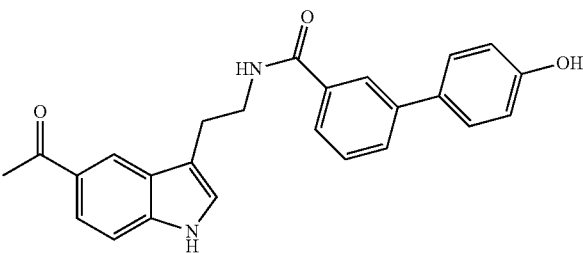 [SMILES: CC(=O)c1ccc2[nH]cc(CCNC(=O)c3cccc(-c4ccc(O)cc4)c3)c2c1] |
| Cpd090 | 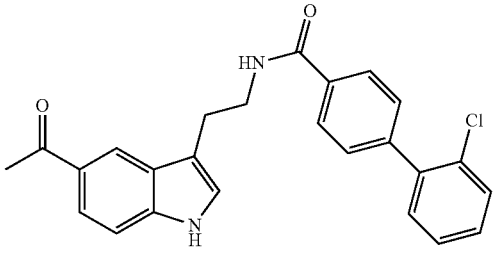 [SMILES: CC(=O)c1ccc2[nH]cc(CCNC(=O)c3ccc(-c4ccccc4Cl)cc3)c2c1] |
| Cpd091 | 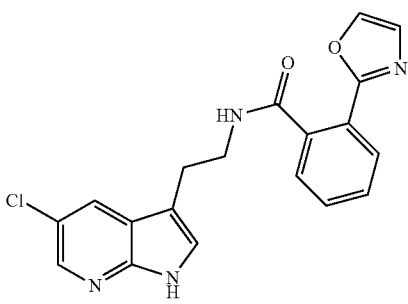 [SMILES: O=C(NCCc1c[nH]c2ncc(Cl)cc12)c1ccccc1-c1ncco1] |
| Cpd092 | 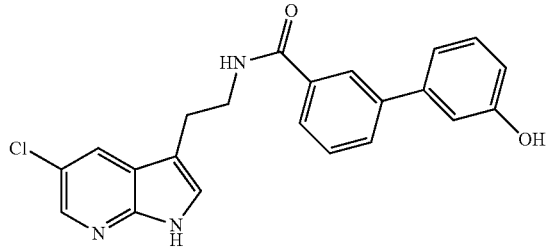 [SMILES: O=C(NCCc1c[nH]c2ncc(Cl)cc12)c1cccc(-c2cccc(O)c2)c1] |

TABLE 1-continued

| CODE | STRUCTURE |
| --- | --- |
| Cpd093 | 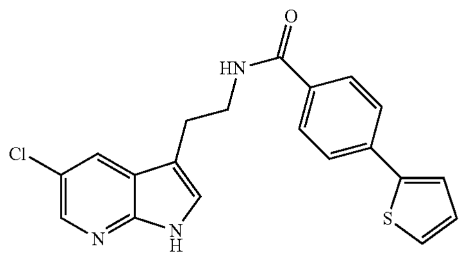 [SMILES: O=C(NCCc1c[nH]c2ncc(Cl)cc12)c1ccc(-c2cccs2)cc1] |
| Cpd094 | 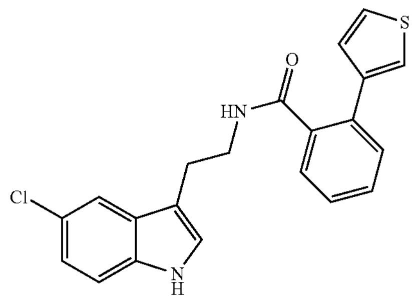 [SMILES: O=C(NCCc1c[nH]c2ccc(Cl)cc12)c1ccccc1-c1ccsc1] |
| Cpd095 | 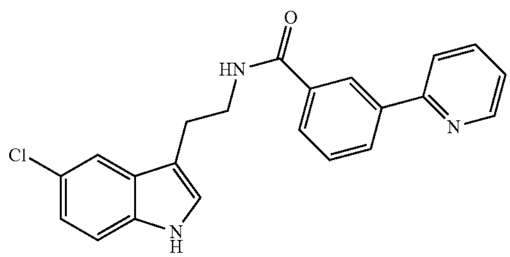 [SMILES: O=C(NCCc1c[nH]c2ccc(Cl)cc12)c1cccc(-c2ccccn2)c1] |
| Cpd096 | 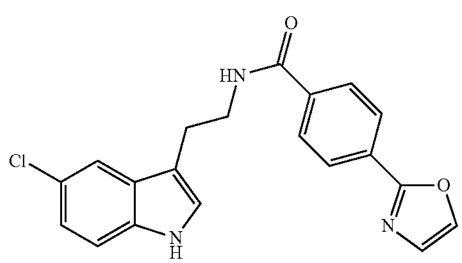 [SMILES: O=C(NCCc1c[nH]c2ccc(Cl)cc12)c1ccc(-c2ncco2)cc1] |
| Cpd097 | 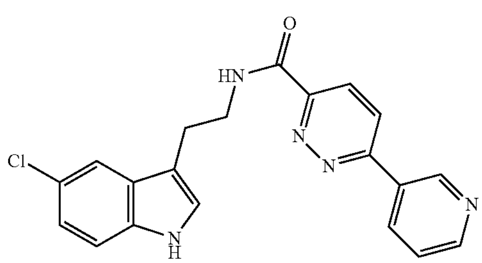 [SMILES: O=C(NCCc1c[nH]c2ccc(Cl)cc12)c1ccc(-c2cccnc2)nn1] |
| Cpd098 | 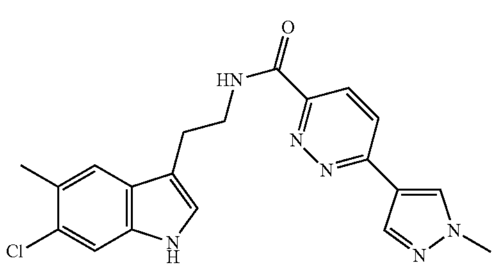 |

TABLE 1-continued
| CODE | STRUCTURE |
|---|---|
| Cpd099 | 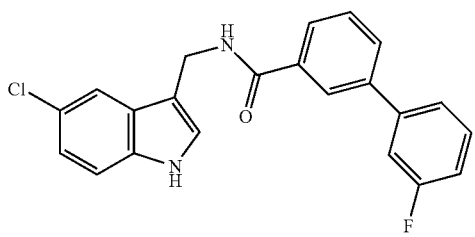 [SMILES: O=C(NCc1c[nH]c2ccc(Cl)cc12)c1cccc(-c2cccc(F)c2)c1] |
| Cpd100 | 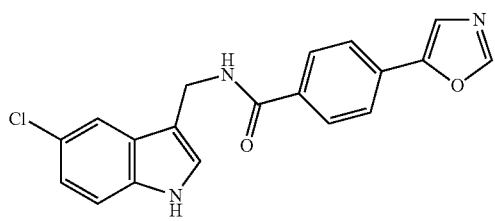 [SMILES: O=C(NCc1c[nH]c2ccc(Cl)cc12)c1ccc(-c2cnco2)cc1] |
| Cpd101 | 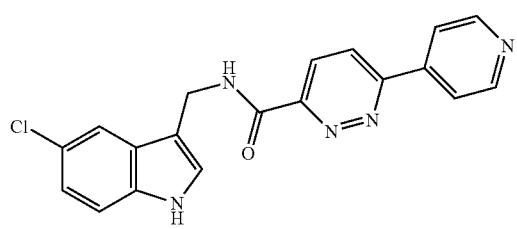 [SMILES: O=C(NCc1c[nH]c2ccc(Cl)cc12)c1ccc(-c2ccncc2)nn1] |
| Cpd102 | 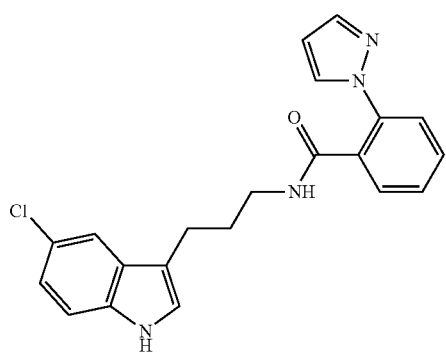 [SMILES: O=C(NCCCc1c[nH]c2ccc(Cl)cc12)c1ccccc1-n1cccn1] |
| Cpd103 | 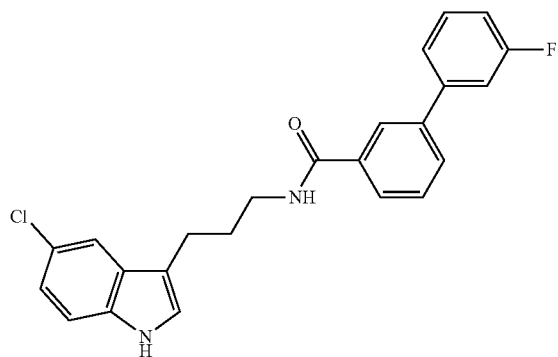 [SMILES: O=C(NCCCc1c[nH]c2ccc(Cl)cc12)c1cccc(-c2cccc(F)c2)c1] |

TABLE 1-continued

| CODE | STRUCTURE |
|---|---|
| Cpd104 | 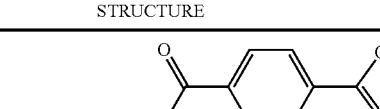 |

Part A

Method A

A mixture of 2-(1H-indol-3-yl)alkylamine (1 equivalent), a carboxylic acid (1.1 equivalents), HATU (1.3 equivalents) and N,N-diisopropylethylamine (2.5 equivalents) in DMF (15 mL/mmol) was stirred at room temperature for 18 hours and concentrated under reduced pressure. The residue was dissolved in ethyl acetate and the organic layer was washed with water, dried with magnesium sulphate and evaporated to dryness. The crude material was purified by flash chromatography on silica gel to yield the desired compound.

Method B

A mixture of intermediates 1, 2 or 3 (1 equivalent), a boronic acid (1.05 equivalents), sodium carbonate (2 equivalents) and tetrakis(triphenylphosphine)palladium (0.05 equivalents) in water (5 mL/mmol) and dimethoxyethane (15 mL/mmol) was irradiated in a microwave oven at 130° C. for 15 minutes. The resulting mixture was partitioned between water and ethyl acetate and the phases were separated. The organic layer was washed with water and concentrated under reduced pressure. The crude material was purified by flash chromatography on silica gel to yield the desired compound.

Method C

Triethylamine (1.2 equivalents) was added to a mixture of a 2-(1H-indol-3-yl)alkylamine (1 equivalent) and an acid chloride (1.05 equivalents) in dichloromethane (15 mL/mmol) at 0° C. The reaction mixture was allowed to warm at room temperature and stirred until consumption of the amine (0.5 to 24 hours). The reaction mixture was concentrated under reduced pressure and the crude material was purified by flash chromatography on silica gel to yield the desired compound.

Method D

Synthesis of Substituted 2-(1H-indol-3-yl)ethanamine

Step I: Substituted 2-iodo-aniline

Iodine (1 eq) was added to a stirred mixture of silver sulphate (1 eq) and an aniline (1 eql) in ethanol (6.21 mL/mmol). The reaction mixture was then stirred at room temperature for 18 hours and filtered over celite. The solution was concentrated under reduced pressure and the residue was partitioned between ethyl acetate and a saturated aqueous solution of sodium thiosulphate. The organic layer was washed with brine, dried with magnesium sulphate and concentrated under reduced pressure. The crude residue was purified by flash chromatography on silica gel to yield a substituted 2-iodo-aniline Step II Substituted 2-(2-(triethylsilyl))-1H-indol-3-yl)ethanol A 2-iodo-aniline (1 equivalent), 4-(triethylsilyl)but-3-yn-1-ol (1.1 equivalents), Bis(diphenylphosphino)ferrocene] palladium(II) chloride (0.05 equivalents), lithium chloride (1 equivalent) and sodium carbonate (2 equivalents) were suspended in DMF (2.87 mL/mmol) and the mixture was stirred at 100° C. for 15 hours. The solution was concentrated under reduced pressure and diluted in ethyl acetate. The organic layer was successively washed with brine, sodium thiosulphate, dried over magnesium sulphate and concentrated under reduced pressure. The crude residue was purified by flash chromatography on silica gel to yield the title compound.

Step III Substituted 3-(2-bromoethyl)-2-(triethylsilyl)-1H-indole

A mixture of 2-(2-(triethylsilyl))-1H-indol-3-yl)ethanol (1 equivalent) in THF (2.8 mL/mmol) was added to a solution of triphenyl phosphine (1.5 equivalents) and perbromomethane (1.5 equivalents) in THF (3.76 mL/mmol) pre-stirred for (0.5-1) hour. The resulting mixture was stirred at room temperature for 18 hours. The reaction mixture was then filtered and concentrated under reduced pressure and the crude residue was purified by flash chromatography on silica gel to yield the title compound.

Step IV Substituted 3-(2-azidoethyl)-2-(triethylsilyl)-1H-indole

A mixture of 3-(2-bromoethyl)-2-(triethylsilyl)-1H-indole (1 equivalent) and sodium azide (3 equivalents) in DMF (9 mL/mmol) was stirred at 70° C. for 4 hours and concentrated under reduced pressure. The residue was diluted in ethyl acetate, washed with brine, dried over magnesium sulphate and concentrated under reduced pressure to give the title compound.

Step V Substituted 2-(1H-indol-3-yl)ethanamine

A mixture of 3-(2-azidoethyl)-2-(triethylsilyl)-1H-indole (1 equivalent) and triphenyl phosphine (1.5 equivalents) in methanol (4.6 mL/mmol) was stirred at 70° C. for 2 hours.

The reaction mixture was concentrated under reduced pressure and the crude material was dissolved in a solution of tetrabutylamonium fluoride (3 equivalents, 1M) in THF and stirred at room temperature for 18-36 hours and concentrated under reduced pressure. The title compound was used without any further purification.

Examples of the Preparation of Intermediates

Intermediate 1-Preparation of N-(2-(5-chloro-1H-indol-3-yl)ethyl)-2-iodobenzamide N-(2-(5-chloro-1H-indol-3-yl)ethyl)-2-iodobenzamide was prepared according to method C with triethylamine (1.19 mL; 8.48 mmol), 2-(5-chloro-1H-indol-3-yl)ethanamine hydrochloride (0.800 g; 3.90 mmol) and 2-iodobenzoyl chloride (0.968 g; 3.56 mmol) in dichloromethane (75 mL). The mixture was stirred for 20 minutes at room temperature and was evaporated to dryness. The crude material was purified by flash chromatography on silica gel (eluent 1 to 10% ethyl acetate in dichloromethane) to furnish 1.32 g (92%) of N-(2-(5-chloro-1H-indol-3-yl)ethyl)-2-iodobenzamide as a white solid.

ESI/APCI(+): 425 (M+H), 447 (M+Na); ESI/APCI(−): 423 (M−H).

Intermediate 2-Preparation of N-(2-(5-chloro-1H-indol-3-yl)ethyl)-3-iodobenzamide N-(2-(5-chloro-1H-indol-3-yl)ethyl)-3-iodobenzamide was prepared according to method C with triethylamine (2.23 mL; 15.90 mmol), 2-(5-chloro-1H-indol-3-yl)ethanamine hydrochloride (1.5 g; 6.36 mmol) and 3-iodobenzoyl chloride (1.82 g; 6.68 mmol) in dichloromethane (75 mL). The mixture was stirred for 20 minutes at room temperature and was evaporated under reduced pressure. The crude material was purified by flash chromatography on silica gel (eluent 2 to 20% ethyl acetate in dichloromethane) to provide 2.56 g (95%) of N-(2-(5-chloro-1H-indol-3-yl)ethyl)-3-iodobenzamide as a white solid.

ESI/APCI(+): 425 (M+H), 447 (M+Na); ESI/APCI(−): 423 (M−H).

Intermediate 3—Preparation of N-(2-(5-chloro-1H-indol-3-yl)ethyl)-4-iodobenzamide N-(2-(5-chloro-1H-indol-3-yl)ethyl)-4-iodobenzamide was prepared according to method C with triethylamine (2.23 mL; 15.90 mmol), 2-(5-chloro-1H-indol-3-yl)ethanamine hydrochloride (1.5 g; 6.36 mmol) and 4-iodobenzoyl chloride (1.82 g; 6.68 mmol) in dichloromethane (75 mL). The mixture was stirred for 20 minutes at room temperature and was evaporated under reduced pressure. The crude material was purified by flash chromatography on silica gel (eluent 2 to 20% ethyl acetate in dichloromethane) to provide 1.22 g (45%) of N-(2-(5-chloro-1H-indol-3-yl)ethyl)-4-iodobenzamide as a white solid.

ESI/APCI(+): 425 (M+H), 447 (M+Na); ESI/APCI(−): 423 (M−H).

Intermediate 4—Preparation of (5-Chloro-1H-indol-3-yl)methanamine

A solution of 5-chloro-1H-indole-3-carbaldehyde (0.690 g; 3.76 mmol), hydroxylamine hydrochloride (0.366 g; 5.27 mmol) and sodium acetate (0.463 g; 5.65 mmol) in ethanol (10 mL) was stirred at reflux for 3.5 hours. The reaction mixture was concentrated under reduced pressure and the residue was partitioned between ethyl acetate and brine and extracted with ethyl acetate. The solvent was evaporated and the residue (crude oxime) was dissolved in glacial acetic acid (30 mL). Zinc dust (1.48 g; 22.59 mmol) was added to the solution, and the mixture was stirred at room temperature for 14 hours. The resulting suspension was filtered on a Celite pad and the cake was washed with ethyl acetate. The filtrate was concentrated under reduced pressure and the residue was partitioned between an aqueous solution of sodium carbonate and ethyl acetate. The organic layer was dried over magnesium sulphate, filtered, and concentrated to give 0.680 (88%) of (5-Chloro-1H-indol-3-yl)methanamine as a brown solid.

ESI/APCI(+): 164 (M+H—NH$_3$); ESI/APCI(−): 179 (M−H).

Intermediate 5—Preparation of 6-chloro-N-(2-(5-chloro-1H-indol-3-yl)ethyl)pyridazine-3-carboxamide Thionyl chloride (0.092 mL; 0.150 mmol) was added to a suspension of 6-chloropyridazine-3-carboxylic acid (0.100 g; 0.630 mmol) in chloroform (1 mL); the resulting mixture was refluxed for 18 hours and concentrated under reduced pressure. The residue was dissolved in dichloromethane (3 mL) and 2-(5-chloro-1H-indol-3-yl)ethanamine hydrochloride (0.160 g; 0.693 mmol) and N-ethyl-N-isopropylpropan-2-amine (0.271 mL; 1.58 mmol) were added. The resulting green solution was stirred at room temperature for 2 hours, diluted with dichloromethane and successively washed with sodium hydrogen sulphate (1M), sodium carbonate (1M) and brine, dried over magnesium sulphate and the crude material was purified by flash chromatography on silica gel (eluent 10 to 60% ethyl acetate in dichloromethane) to yield 0.048 g (23%) of 6-chloro-N-(2-(5-chloro-1H-indol-3-yl)ethyl)pyridazine-3-carboxamide.

ESI/APCI(+): 335 (M+H), 357 (M+Na); ESI/APCI(+): 333 (M−H).

Intermediate 6—Preparation of 3-(5-Chloro-1H-indol-3-yl)propan-1-ol

A mixture of (4-chlorophenyl)hydrazine hydrochloride (5.26 g; 28.50 mmol) and 3,4-dihydro-2H-pyran (2.63 mL; 28.50 mmol) in a mixture of water (9 mL) and dioxane (36 mL) was stirred at 100° C. for 48 hours. After cooling to room temperature the mixture was diluted with ethyl acetate. The aqueous layer was separated and extracted with ethyl acetate. The combined organic layers were dried over magnesium sulphate, and concentrated under reduced pressure. The residue was purified by flash chromatography on silica gel (eluent: 0 to 6% methanol in dichloromethane) to afford 3.85 g (64%) of 3-(5-Chloro-1H-indol-3-yl)propan-1-ol as an oily residue.

ESI/APCI(+): 210 (M+H); ESI/APCI(−): 208 (M−H).

Intermediate 7—Preparation of 3-(3-Bromopropyl)-5-chloro-1H-indole

Carbon tetrabromine (2.37 g; 7.15 mmol) was added to the solution of triphenylphosphine (1.90 g; 7.15 mmol) in tetrahydrofuran (20 mL) and the mixture was stirred at room temperature for 15 min. A solution of 3-(5-Chloro-1H-indol-3-yl)propan-1-ol (1 g; 4.77 mmol) in tetrahydrofuran (12 mL) was then added to the green suspension and the resulting reaction mixture was stirred for 18 hours at room temperature. The solution was concentrated under reduced pressure, and the residue was purified by flash chromatography on silica gel (eluent: 2 to 40% ethyl acetate in heptane) to afford 0.791 g, (61%) of 3-(3-Bromopropyl)-5-chloro-1H-indole as a dark oily residue.

$^1$H NMR (DMSO-d$_6$) δ 11.04 (s, 1H); 7.56 (d, 1H); 7.35 (d, 1H); 7.24 (d, 1H); 7.06 (dd, 1H, 3.54 (t, 2H); 2.80 (t, 2H); 2.13 (quint, 2H).

Intermediate 8—Preparation of 3-(3-Azidopropyl)-5-chloro-1H-indole

A mixture of 3-(3-Bromopropyl)-5-chloro-1H-indole (0.730 g; 2.68 mmol) and sodium azide (0.522 g; 8.03 mmol) was stirred in DMF (5 mL) for 18 hours and was then concentrated under reduced pressure. The residue was partitioned between water and dichloromethane. After separation, the organic layer was dried over magnesium sulphate and the volatiles were evaporated under reduced pressure to yield quantitatively 3-(3-Azidopropyl)-5-chloro-1H-indole as an oily residue which was used without purification.

Intermediate 9—Preparation of 3-(5-Chloro-1H-indol-3-yl)propan-1-amine

To a solution of 3-(3-Azidopropyl)-5-chloro-1H-indole (0.299 g; 1.27 mmol) in THF (9 mL) were added triphenylphosphine (0.354 g; 1.34 mmol) and water (0.6 mL). The reaction mixture was stirred at room temperature for 22 hours and was then concentrated under reduced pressure. The residue was dissolved in dichloromethane (10 mL) and 10 mL of 6N hydrochloric acid were added. After separation, the aqueous layer was further extracted with dichloromethane (2×10 mL) and the pH was adjusted to 14 with an aqueous solution of sodium hydroxide 6N. This basic solution was extracted dichloromethane (3×20 mL) and the combined organic layer was dried over magnesium sulphate, and evaporated to afford 0.089 g (34%) of 3-(5-Chloro-1H-indol-3-yl)propan-1-amine as a white solid.

ESI/APCI(+): 209 (M+H); ESI/APCI(−): 207 (M−H).

Intermediate 10—Preparation of 2-iodo-4-(trifluoromethyl)aniline 2-iodo-4-(trifluoromethyl)aniline was prepared according to method D Step I with iodine (1.58 g; 6.21 mmol), silver sulphate (1.94 g; 6.21 mmol) and 4-(trifluoromethyl)aniline (0.8 mL; 6.21 mmol) in ethanol (40 mL). The crude residue was purified by flash chromatography on silica gel (eluent 2 to 40% ethyl acetate in heptane) to afford 1.08 g (61%) of 2-iodo-4-(trifluoromethyl)aniline as a red oil.

$^1$H NMR (DMSO-d$_6$) δ 7.80 (s, 1H), 7.38 (d, 1H), 6.82 (d, 2H), 5.93 (s, 2H).

Intermediate 11—Preparation of 2-(2-(triethylsilyl)-5-(trifluoromethyl)-1H-indol-3-yl)ethanol 2-(2-(triethylsilyl)-5-(trifluoromethyl)-1H-indol-3-yl)ethanol was prepared according to method D Step II with 2-iodo-4-(trifluoromethyl)aniline (1.0 g; 3.48 mmol), 4-(triethylsilyl)but-3-yn-1-ol (0.807 mL; 3.83 mmol), Bis(diphenylphosphino)ferrocene]palladium(II) chloride (0.142 g; 0.174 mmol), lithium chloride (0.147 g; 3.48 mmol) and sodium carbonate (0.738 g; 6.97 mmol) in DMF (10 mL). The crude mixture was purified by flash chromatography on silica gel (eluent 2 to 40% ethyl acetate in heptane) to afford 0.733 g (61%) of 2-(2-(triethylsilyl)-5-(trifluoromethyl)-1H-indol-3-yl)ethanol as a yellow oil.

ESI/APCI(+):344 (M+H); ESI/APCI(−): 343 (M−H).

Intermediate 12—Preparation of 3-(2-bromoethyl)-2-(triethylsilyl)-5-(trifluoromethyl)-1H-indole 3-(2-bromoethyl)-2-(triethylsilyl)-5-(trifluoromethyl)-1H-indole was prepared according to method D Step III with 2-(2-(triethylsilyl)-5-(trifluoromethyl)-1H-indol-3-yl)ethanol (0.730 g; 2.13 mmol) in THF (6 mL); triphenyl phosphine (0.836 g; 3.19 mmol) and perbromomethane (1.06 g; 3.19 mmol) in THF (12 mL) pre-stirred for 1 hour. The crude residue was purified by flash chromatography on silica gel (eluent 5 to 40% ethyl acetate in heptane) to afford 0.449 g (52%) of 3-(2-bromoethyl)-2-(triethylsilyl)-5-(trifluoromethyl)-1H-indole as a yellow oil.

Intermediate 13—Preparation of 3-(2-azidoethyl)-2-(triethylsilyl)-5-(trifluoromethyl)-1H-indole 3-(2-azidoethyl)-2-(triethylsilyl)-5-(trifluoromethyl)-1H-indole was prepared according to method D Step IV with 3-(2-bromoethyl)-2-(triethylsilyl)-5-(trifluoromethyl)-1H-indole (0.448 g; 1.10 mmol) and sodium azide (0.215 g; 3.31 mmol) in DMF (10 mL); the yield was 0.402 g (99%) of 3-(2-azidoethyl)-2-(triethylsilyl)-5-(trifluoromethyl)-1H-indole as a brown oil.

ESI/APCI(+):391 (M+Na); ESI/APCI(−): 367 (M−H).

Intermediate 14—Preparation of 2-(5-(trifluoromethyl)-1H-indol-3-yl)ethanamine 2-(5-(trifluoromethyl)-1H-indol-3-yl)ethanamine was prepared according to method D Step V with 3-(2-azidoethyl)-2-(triethylsilyl)-5-(trifluoromethyl)-1H-indole (0.400 g; 1.09 mmol) and triphenyl phosphine (0.427 g; 1.63 mmol) in methanol (5 mL) and tetrabutylamonium fluoride (3.26 mL, 1M) in THF (stirred for 36 hours).

Intermediate 15—Preparation of 5-chloro-2-iodo-4-methylaniline

A solution of iodine (9.86 g; 38.84 mmol) and potassium iodide (6.45 g; 38.84 mmol) in water was added dropwise to a suspension of 3-chloro-4-methylaniline (5.00 g; 35.31 g) in a solution of sodium bicarbonate (4.75 g; 56.50 mmol). The resulting mixture was stirred 72 hours at room temperature filtrated and the solid dissolved in dichloromethane, washed with a saturated solution of sodium thiosulphate, dried over magnesium sulphate and concentrated under reduced pressure. The crude residue was purified by flash chromatography on silica gel (eluent 2 to 20% ethyl acetate in heptane) to yield 2.30 g (24%) of 5-chloro-2-iodo-4-methylaniline as a brown solid.

ESI/APCI(+): 268 (M+H).

Intermediate 16—Preparation of 2-(6-chloro-5-methyl-2-(triethylsilyl)-1H-indol-3-yl)ethanol 2-(6-chloro-5-methyl-2-(triethylsilyl)-1H-indol-3-yl)ethanol was prepared according to method D Step II with 5-chloro-2-iodo-4-methylaniline (1.50 g; 5.61 mmol), 4-(triethylsilyl)but-3-yn-1-ol (2.36 mL; 11.22 mmol), Bis(diphenylphosphino)ferrocene]palladium(II) chloride (0.229 g; 0.280 mmol), lithium chloride (0.237 g; 5.61 mmol) and sodium carbonate (1.19 g; 11.22 mmol) in DMF (14 mL). The crude material was purified by flash chromatography on silica gel (eluent 2 to 20% ethyl acetate in heptane) to afford 1.44 g (79%) of 2-(6-chloro-5-methyl-2-(triethylsilyl)-1H-indol-3-yl)ethanol as a brown oil.

ESI/APCI(+): 324 (M+H); ESI/APCI(−): 322 (M−H).

Intermediate 17—Preparation of 3-(2-bromoethyl)-6-chloro-5-methyl-2-(triethylsilyl)-1H-indole 3-(2-bromoethyl)-6-chloro-5-methyl-2-(triethylsilyl)-1H-indole was prepared according to method D Step III with 2-(6-chloro-5-methyl-2-(triethylsilyl)-1H-indol-3-yl)ethanol (1.44 g; 4.45 mmol) in THF (6 mL) and triphenyl phosphine (1.75 g; 6.67 mmol) and perbromomethane (2.21 g; 6.67 mmol) in THF (40 mL) pre-stirred for 30 minutes. The crude mixture was purified by flash chromatography on silica gel (eluent 2 to 20% ethyl acetate in heptane) to afford 0.725 g (42%) of 3-(2-bromoethyl)-6-chloro-5-methyl-2-(triethylsilyl)-1H-indole as a brown oil.

Intermediate 18—Preparation of 3-(2-azidoethyl)-6-chloro-5-methyl-2-(triethylsilyl)-1H-indole 3-(2-azidoethyl)-6-chloro-5-methyl-2-(triethylsilyl)-1H-indole was prepared according to method D Step IV with 3-(2-bromoethyl)-6-chloro-5-methyl-2-(triethylsilyl)-1H-indole (0.725 g; 1.87 mmol) and sodium azide (0.365 g; 5.62 mmol) in DMF (8 mL); the yield was quantitative as a brown oil.

Intermediate 19—Preparation of 2-(6-chloro-5-methyl-1H-indol-3-yl)ethanamine 2-(6-chloro-5-methyl-1H-indol-3-yl)ethanamine was prepared according to method D Step V with 3-(2-azidoethyl)-6-chloro-5-methyl-2-(triethylsilyl)-1H-indole (0.654 g; 1.87 mmol) and triphenylphosphine (0.737 g; 2.81 mmol) in methanol (10 mL) and tetrabutylamonium fluoride (5.62 mL 1M) in THF (stirred for 36 hours).

Intermediate 20—Preparation of 4,5-dichloro-2-iodoaniline

Iodine monochloride (1.39 mL; 27.77 mmol) was added to a solution of 3,4-dichloroaniline (4.50 g; 27.77 mmol) in acetic acid (15 mL) and the resulting mixture was stirred 30 minutes at room temperature. The solution was concentrated to dryness, neutralized with sodium bicarbonate and extracted with dichloromethane. The combined organic layers were washed with a saturated solution of sodium thiosulphate, dried over magnesium sulphate and concentrated under reduced pressure. The crude material was purified by flash chromatography on silica gel (eluent 2 to 20% ethyl acetate in heptane) to afford 3.46 g (43%) of 4,5-dichloro-2-iodoaniline as a brown solid.

$^1$H NMR (DMSO-d6) δ 7.73 (s, 1H); 6.91 (s, 1H), 5.63 (br s, 2H).

Intermediate 21—Preparation of 2-(5,6-dichloro-2-(triethylsilyl)-1H-indol-3-yl)ethanol 2-(5,6-dichloro-2-(triethylsilyl)-1H-indol-3-yl)ethanol was prepared according to method D Step II with 4,5-dichloro-2-iodoaniline (1.50 g; 5.21 mmol), 4-(triethylsilyl)but-3-yn-1-ol (1.65 mL; 7.81 mmol), Bis(diphenylphosphino)ferrocene]palladium(II) chloride (0.212 g; 0.260 mmol), lithium chloride (0.221 g; 5.21 mmol) and sodium carbonate (1.10 g; 10.42 mmol) in DMF (14 mL). The crude material was purified by flash chromatography on silica gel (eluent 2 to 20% ethyl acetate in heptane) to afford 1.44 g (79%) of 2-(5,6-dichloro-2-(triethylsilyl)-1H-indol-3-yl) ethanol as a brown oil.

ESI/APCI(+):344 (M+H); ESI/APCI(−):342 (M−H).

Intermediate 22—Preparation of 3-(2-bromoethyl)-5,6-dichloro-2-(triethylsilyl)-1H-indole 3-(2-bromoethyl)-5,6-dichloro-2-(triethylsilyl)-1H-indole was prepared according to method D Step III with 2-(5,6-dichloro-2-(triethylsilyl)-1H-indol-3-yl)ethanol (1.7 g; 4.94 mmol) in THF (6 mL) and triphenyl phosphine (2.59 g; 9.87 mmol) and perbromomethane (3.27 g; 9.87 mmol) in THF (40 mL) pre-stirred for 30 minutes. The crude mixture was purified by flash chromatography on silica gel (eluent 2 to 20% ethyl acetate in heptane) to yield 0.548 g (27%) of 3-(2-bromoethyl)-5,6-dichloro-2-(triethylsilyl)-1H-indole as a brown oil.

$^1$H NMR (DMSO-d$_6$) δ 10.90 (s, 1H); 7.88 (s, 1H); 7.56 (s, 1H); 3.61 (t, 2H); 3.28 (t, 2H); 0.95 (m, 15H).

Intermediate 23—Preparation of 3-(2-azidoethyl)-5,6-dichloro-2-(triethylsilyl)-1H-indole 3-(2-azidoethyl)-5,6-dichloro-2-(triethylsilyl)-1H-indole was prepared according to method D Step IV with 3-(2-bromoethyl)-5,6-dichloro-2-(triethylsilyl)-1H-indole (0.548 g; 1.35 mmol) and sodium azide (0.262 g; 4.04 mmol) in DMF (8 mL); the yield was quantitative as a brown oil.

ESI/APCI(−): 367 (M−H).

Intermediate 24—Preparation of 2-(5,6-dichloro-1H-indol-3-yl)ethanamine 2-(5,6-dichloro-1H-indol-3-yl)ethanamine was prepared according to method D Step V with 3-(2-azidoethyl)-5,6-dichloro-2-(triethylsilyl)-1H-indole (0.497 g; 1.35 mmol) and triphenylphosphine (0.529 g; 1.35 mmol) in methanol (10 mL) and tetrabutylamonium fluoride (4.04 mL 1M) in THF (stirred for 36 hours).

Intermediate 25—Preparation of 5-chloro-3-iodopyridin-2-amine 5-chloro-3-iodopyridin-2-amine was prepared according to method D Step I with Iodine (7.55 g; 29.73 mmol) was added to a mixture of 5-chloropyridin-2-amine (3.00 g; 22.87 mmol) and silver sulphate (9.36 g; 29.73 mmol) in ethanol (150 mL). The crude residue was purified by flash chromatography on silica gel (eluent 0 to 30% of ethyl acetate in heptane) to give 3.71 g (64%) of 5-chloro-3-iodopyridin-2-amine as a beige solid.

ESI/APCI(+): 255 (M+Na).

$^1$H NMR (CDCl3) □ 7.99 (d, 1H); 7.84 (d, 1H), 4.96 (s, 2H).

Intermediate 26—Preparation of 2-(5-chloro-2-(triethylsilyl)-1H-pyrrolo[2,3-b]pyridin-3-yl)ethanol 2-(5-chloro-2-(triethylsilyl)-1H-pyrrolo[2,3-b]pyridin-3-yl)ethanol was prepared according to method D Step II with 5-chloro-3-iodopyridin-2-amine (2 g; 7.86 mmol), 4-(triethylsilyl)but-3-yn-1-ol (4.35 g; 23.58 mmol); (1,1'-bis(diphenylphosphino)ferrocene)-dichloromethane (0.321 g; 0.393 mmol), lithium chloride (0.333 g; 7.86 mmol) and sodium carbonate (1.67 g; 15.72 mmol) in DMF (15 mL) for approximately 20 hours. The crude material was purified by flash chromatography on silica gel (eluent 2 to 20% ethyl acetate in heptane) to afford 1.44 g (79%) of 2-(5,6-dichloro-2-(triethylsilyl)-1H-indol-3-yl)ethanol as a brown oil. The crude material was purified by flash chromatography on silica gel (eluent 7 to 80% of ethyl acetate in heptane) to give 2.15 g (88%) of 2-(5-chloro-2-(triethylsilyl)-1H-pyrrolo[2,3-b]pyridin-3-yl)ethanol as a white solid.

ESI/APCI (+): 311 (M+H); ESI/APCI (−): 309 (M−H).

Intermediate 27—Preparation of 3-(2-bromoethyl)-5-chloro-2-(triethylsilyl)-1H-pyrrolo[2,3-b]pyridine 3-(2-bromoethyl)-5-chloro-2-(triethylsilyl)-1H-pyrrolo[2,3-b]pyridine was prepared according to method D Step III with 2-(5-chloro-2-(triethylsilyl)-1H-pyrrolo[2,3-b]pyridin-3-yl)ethanol (2.0 g; 6.43 mmol) in THF (30 mL) and triphenyl phosphine (2.56 g; 9.65 mmol) and perbromomethane (3.27 g, 9.65 mmol) in THF (40 mL) pre-stirred for 30 minutes. The crude mixture was purified by flash chromatography on silica gel (eluent 5 to 40% of ethyl acetate in heptanes) to yield 1.08 g (45%) of 3-(2-bromoethyl)-5-chloro-2-(triethylsilyl)-1H-pyrrolo[2,3-b]pyridine as a white solid.

$^1$H NMR (CDCl$_3$) □ 8.72 (s, 1H); 8.24 (d, 1H); 7.87 (d, 1H); 3.50 (t, 2H), 3.31 (t, 2H) 1.01 (m, 9H); 0.93 (m, 6H).

Intermediate 28—Preparation of 3-(2-azidoethyl)-5-chloro-2-(triethylsilyl)-1H-pyrrolo[2,3-b]pyridine A mixture of 3-(2-bromoethyl)-5-chloro-2-(triethylsilyl)-1H-pyrrolo[2,3-b]pyridine (1.05 g; 2.81 mmol) and sodium azide (0.547 g; 8.43 mmol) in DMF (8 mL) was stirred for 18 hours at 80° C. and was concentrated under reduced pressure. The residue was partitioned between water and dichloromethane. After separation, the dichloromethane solution was dried over magnesium sulphate and was evaporated to give 0.943 g (100%) of 3-(2-azidoethyl)-5-chloro-2-(triethylsilyl)-1H-pyrrolo[2,3-b]pyridine as a solid.

ESI/APCI(+): 336 (M+H); ESI/APCI(−): 334 (M−H).

Intermediate 29—Preparation of 2-(5-chloro-2-(triethylsilyl)-1H-pyrrolo[2,3-b]pyridin-3-yl)ethanamine A mixture of 3-(2-azidoethyl)-5-chloro-2-(triethylsilyl)-1H-pyrrolo[2,3-b]pyridine (0.900 g; 2.68 mmol) and triphenylphosphine (1.05 g; 4.02 mmol) in methanol (25 ml) was stirred at 80° C. for 1 hour and was concentrated under reduced pressure. The residue was dissolved in toluene (15 mL). Hydrochloric acid (2 mL) and water 15 mL were added. After two layers' separation, the aqueous solution was extracted 3×15 mL of toluene and was made alkaline by addition of a solution of sodium hydroxide 2N. The formed precipitate was filtered off. The filtrate was extracted with dichloromethane (5×15 mL). Combined dichloromethane extracts were dried over magnesium sulphate and concentrated under reduced pressure to give 0.515 g (62%) of 2-(5-chloro-2-(triethylsilyl)-1H-pyrrolo[2,3-b]pyridin-3-yl)ethanamine as an oily residue.

ESI/APCI(+): 310 (M+H); 293 (M+H—NH$_3$); ESI/APCI (−): 308 (M−H).

Intermediate 30—Preparation of 2-(5-chloro-1H-pyrrolo[2,3-b]pyridin-3-yl)ethanamine hydrochloride 2-(5-chloro-2-(triethylsilyl)-1H-pyrrolo[2,3-b]pyridin-3-yl)ethanamine (0.360 g; 1.16 mmol) was dissolved in a 1M solution of tetrabutylammonium fluoride in THF (4 mL; 4 mmol). The mixture was stirred overnight at room temperature and was concentrated under reduced pressure. The residue was dissolved in dichloromethane. A 2M solution of hydrogen chloride in ether was added and the formed precipitate collected by filtration and dried under reduced pressure to give 0.239 g (89%) of 2-(5-chloro-1H-pyrrolo[2,3-b]pyridin-3-yl)ethanamine hydrochloride as a beige solid.

ESI/APCI(+): 196 (M+H), 179 (M+H—NH3).

Intermediate 31—Preparation of 4-amino-3-iodobenzonitrile 4-amino-3-iodobenzonitrile was prepared according to method D Step I with Iodine (0.645 g; 2.54 mmol), silver sulphate (0.791 g; 2.54 mmol) and 4-aminobenzonitrile (0.300 g; 2.54 mmol) in ethanol (10 mL). The crude residue was purified by flash chromatography on silica gel (eluent 2 to 40% ethyl acetate in heptane) to yield 0.222 g (36%) of 4-amino-3-iodobenzonitrile as a white solid.

$^1$H NMR (DMSO-d$_6$) δ 7.96 (d, 1H), 7.45 (dd, 1H), 6.76 (d, 1H), 6.22 (s, 2H).

Intermediate 32—Preparation of 1-(4-amino-3-iodophenyl)ethanone 1-(4-amino-3-iodophenyl)ethanone was prepared according to method D Step I with Iodine (2.82 g; 11.10 mmol) silver sulphate (3.46 g; 11.10 mmol) and 1-(4-aminophenyl) ethanone (1.50 g; 11.10 mmol) in ethanol (40 mL). The crude residue was purified by flash chromatography on silica gel (eluent 2 to 40% ethyl acetate in heptane) to yield 0.514 g (18%) of 1-(4-amino-3-iodophenyl)ethanone as a pale yellow solid.

Intermediate 33—Preparation of 3,4,5-trifluoro-2-iodoaniline 3,4,5-trifluoro-2-iodoaniline was prepared according to method D Step I with iodine (0.621 g; 2.45 mmol), silver sulphate (0.763 g; 2.45 mmol) and 3,4,5-trifluoroaniline (0.360 g; 2.45 mmol) in ethanol (5 mL). The crude residue was purified by flash chromatography on silica gel (eluent 2 to 40% ethyl acetate in heptane) to yield 0.279 g (42%) of 3,4,5-trifluoro-2-iodoaniline as a white solid.

ESI/APCI(−): 272 (M−H).

Intermediate 34—Preparation of 3-(2-aminoethyl)-1H-indole-5-carbonitrile 3-(2-aminoethyl)-1H-indole-5-carbonitrile can be prepared according to method D step II, III, IV and V starting from 4-amino-3-iodobenzonitrile.

Intermediate 35—Preparation of 1-(3-(2-aminoethyl)-1H-indol-5-yl)ethanone 1-(3-(2-aminoethyl)-1H-indol-5-yl)ethanone can be prepared according to method D step II, III, IV and V starting from 1-(4-amino-3-iodophenyl)ethanone.

Intermediate 36—Preparation of 2-(4,5,6-trifluoro-1H-indol-3-yl)ethanamine 1-(3-(2-aminoethyl)-1H-indol-5-yl)ethanone can be prepared according to method D step II, III, IV and V starting from 3,4,5-trifluoro-2-iodoaniline.

Examples of the Preparation of Compounds of the Invention

Example 1

Preparation of N-(2-(5-chloro-1H-indol-3-yl)ethyl)-6-morpholinonicotinamide

N-(2-(5-chloro-1H-indol-3-yl)ethyl)-6-morpholinonicotinamide was obtained following Method C starting from 2-(5-chloro-1H-indol-3-yl)ethanamine hydrochloride (0.042 g, 0.178 mmol), 6-morpholinonicotinoyl chloride (0.045 g; 0.178 mmol), and triethylamine (0.062 mL; 0.446 mmol) in dichloromethane (5 mL). Flash chromatography on silica gel (eluent 1 to 10% methanol in dichloromethane) furnished 0.039 g (57%) of N-(2-(5-chloro-1H-indol-3-yl)ethyl)-6-morpholinonicotinamide as a solid.
ESI/APCI(+): 385 (M+H); ESI/APCI(−): 383 (M−H).
$^1$H NMR (DMSO-$d_6$) δ 11.03 (s, 1H), 8.61 (s, 1H), 8.41 (s, 1H), 7.97 (d, 1H), 7.60 (s, 1H), 7.35 (d, 1H), 7.25 (s, 1H), 7.05 (d, 1H), 6.85 (d, 1H), 3.69 (s, 4H), 3.50 (m, 6H), 2.90 (m, 2H).

Example 2

Preparation of N-(2-(5-Fluoro-1H-indol-3-yl)ethyl) biphenyl-4-carboxamide

N-(2-(5-Fluoro-1H-indol-3-yl)ethyl)biphenyl-4-carboxamide was obtained following Method C starting from 2-(5-fluoro-1H-indol-3-yl)ethanamine (0.100 g, 0.561 mmol), biphenyl-4-carbonyl chloride (0.130 g; 0.589 mmol), and triethylamine (0.095 mL; 0.673 mmol) in dichloromethane (5 mL). Flash chromatography on silica gel (eluent 2 to 20% ethyl acetate in dichloromethane) furnished 0.152 g (76%) of N-(2-(5-Fluoro-1H-indol-3-yl)ethyl)biphenyl-4-carboxamide as a white solid.
ESI/APCI(+): 359 (M+H), 381 (M+Na); ESI/APCI(−): 357 (M−H).
$^1$H NMR (DMSO-$d_6$) δ 10.94 (s, 1H); 8.68 (t, 1H); 7.75 (m, 4H); 7.50 (t, 2H); 7.42 (d, 1H); 7.36 (m, 2H); 7.28 (d, 1H); 6.91 (td, 1H); 3.54 (q, 2H); 2.94 (t, 2H).

Example 3

Preparation of N-(2-(5-Methyl-1H-indol-3-yl)ethyl) biphenyl-4-carboxamide

N-(2-(5-Methyl-1H-indol-3-yl)ethyl)biphenyl-4-carboxamide was obtained following Method C starting from 2-(5-methyl-1H-indol-3-yl)ethanamine hydrochloride (0.080 g, 0.372 mmol), biphenyl-4-carbonyl chloride (0.0864 g; 0.391 mmol), and triethylamine (0.131 mL; 0.930 mmol) in dichloromethane (5 mL). Flash chromatography on silica gel eluting with 1 to 10% ethyl acetate in dichloromethane furnished 0.096 g (73%) of N-(2-(5-Methyl-1H-indol-3-yl)ethyl)biphenyl-4-carboxamide as a white solid.
ESI/APCI(+): 355 (M+H), 377 (M+Na); ESI/APCI(−): 353 (M−H).
$^1$H NMR (DMSO-$d_6$) δ 10.68 (s, 1H); 8.66 (t, 1H); 7.95 (d, 2H); 7.75 (m, 4H); 7.50 (t, 2H); 7.39 m, 2H); 7.22 (d, 1H); 7.14 (d, 1H); 6.88 (d, 1H); 3.54 (q, 2H); 2.94 (t, 2H); 2.36 (s, 3H).

Example 4

Preparation of N-(2-(5-Methoxy-1H-indol-3-yl) ethyl)biphenyl-4-carboxamide

N-(2-(5-Methoxy-1H-indol-3-yl)ethyl)biphenyl-4-carboxamide was obtained following Method C starting from 2-(5-methoxy-1H-indol-3-yl)ethanamine (0.100 g, 0.515 mmol), biphenyl-4-carbonyl chloride (0.120 g; 0.541 mmol), and triethylamine (0.087 mL; 0.616 mmol) in dichloromethane (5 mL). Flash chromatography on silica gel (eluent with 10% ethyl acetate in dichloromethane) furnished 0.122 g (64%) of N-(2-(5-Methoxy-1H-indol-3-yl)ethyl)biphenyl-4-carboxamide as a white solid.
ESI/APCI(+): 371 (M+H); ESI/APCI(−): 369 (M−H).

Example 5

Preparation of N-(2-(5-chloro-1H-Indol-3-yl)ethyl) biphenyl-2-carboxamide

N-(2-(5-chloro-1H-Indol-3-yl)ethyl)biphenyl-2-carboxamide was prepared following Method A starting from 2-(5-chloro-1H-indol-3-yl)ethanamine hydrochloride (0.100 g; 0.424 mmol), biphenyl-2-carboxylic acid (0.0943 g; 0.466 mmol), HATU (0.193 g; 0.508 mmol) and N,N-diisopropylethylamine (0.179 mL; 1.06 mmol) in DMF (5 mL). Flash chromatography on silica gel (eluent 1 to 10% ethyl acetate in dichloromethane) furnished 0.109 g (68%) of N-(2-(5-chloro-1H-Indol-3-yl)ethyl)biphenyl-2-carboxamide as a white solid.
ESI/APCI(+): 375 (M+H), 397 (M+Na); ESI/APCI(−): 373 (M−H).

Example 6

Preparation of N-(2-(5-Chloro-1H-indol-3-yl)ethyl) biphenyl-3-carboxamide

N-(2-(5-Chloro-1H-indol-3-yl)ethyl)biphenyl-3-carboxamide was obtained following Method C starting from 2-(5-chloro-1H-indol-3-yl)ethanamine hydrochloride (0.100 g, 0.424 mmol), biphenyl-3-carbonyl chloride (0.0965 g; 0.445 mmol), and triethylamine (0.145 mL; 1.06 mmol) in dichloromethane (5 mL). Flash chromatography on silica gel (eluent 2 to 20% ethyl acetate in dichloromethane) furnished 0.0565 g (36%) of N-(2-(5-Chloro-1H-indol-3-yl)ethyl)biphenyl-3-carboxamide as a white solid.
ESI/APCI(+): 375 (M+H), 397 (M+Na).

Example 7

Preparation of N-(2-(5-Chloro-1H-indol-3-yl)ethyl) biphenyl-4-carboxamide

N-(2-(5-Chloro-1H-indol-3-yl)ethyl)biphenyl-4-carboxamide was obtained following Method C starting from 2-(5-chloro-1H-indol-3-yl)ethanamine hydrochloride (0.100 g, 0.424 mmol), biphenyl-4-carbonyl chloride (0.098 g; 0.445 mmol), and triethylamine (0.131 mL; 0.934 mmol) in dichloromethane (5 mL). Flash chromatography on silica gel (eluent 10% ethyl acetate in dichloromethane) furnished 0.125 g (79%) of N-(2-(5-Chloro-1H-indol-3-yl)ethyl)biphenyl-4-carboxamide as a white solid.
ESI/APCI(+): 375 (M+H); ESI/APCI(−): 373 (M−H).

Example 8

Preparation of N-(2-(5-Chloro-1H-indol-3-yl)ethyl)-4-(thiophen-2-yl)benzamide

N-(2-(5-Chloro-1H-indol-3-yl)ethyl)-4-(thiophen-2-yl) benzamide was obtained following Method C starting from 2-(5-chloro-1H-indol-3-yl)ethanamine hydrochloride (0.100 g, 0.424 mmol), 4-(thiophen-2-yl)benzoyl chloride (0.102 g; 0.445 mmol), and triethylamine (0.149 mL; 1.06 mmol) in dichloromethane (5 mL). Flash chromatography on silica gel (eluent 1 to 10% ethyl acetate in dichloromethane) furnished 0.058 g (36%) of N-(2-(5-Chloro-1H-indol-3-yl)ethyl)-4-(thiophen-2-yl)benzamide as a white solid.
ESI/APCI(+): 381 (M+H); ESI/APCI(−): 379 (M−H).

Example 9

Preparation of N-(2-(5-chloro-1H-indol-3-yl)ethyl)-2'-methoxybiphenyl-2-carboxamide N-(2-(5-chloro-1H-indol-3-yl)ethyl)-2'-methoxybiphenyl-2-carboxamide was prepared according to method B with N-(2-(5-chloro-1H-indol-3-yl)ethyl)-2-iodobenzamide (0.075 g; 0.176 mmol), 2-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 1 to 20% ethyl acetate in dichloromethane) furnished 0.065 g (90%) of N-(2-(5-chloro-1H-indol-3-yl)ethyl)-2'-methoxybiphenyl-2-carboxamide.
ESI/APCI(+): 405 (M+H), 427 (M+Na); ESI/APCI(−): 403 (M−H).

Example 10

Preparation of N-(2-(5-chloro-1H-indol-3-yl)ethyl)-2'-methoxybiphenyl-3-carboxamide N-(2-(5-chloro-1H-indol-3-yl)ethyl)-2'-methoxybiphenyl-3-carboxamide was prepared according to method B with N-(2-(5-chloro-1H-indol-3-yl)ethyl)-3-iodobenzamide (0.075 g; 0.176 mmol), 2-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 1 to 20% ethyl acetate in dichloromethane) furnished 0.056 g (78%) of N-(2-(5-chloro-1H-indol-3-yl)ethyl)-2'-methoxybiphenyl-3-carboxamide as a white solid.
ESI/APCI(+): 405 (M+H), 427 (M+Na); ESI/APCI(−): 403 (M−H).

Example 11

Preparation of N-(2-(5-chloro-1H-indol-3-yl)ethyl)-2'-methoxybiphenyl-4-carboxamide N-(2-(5-chloro-1H-indol-3-yl)ethyl)-2'-methoxybiphenyl-4-carboxamide was prepared according to method B with N-(2-(5-chloro-1H-indol-3-yl)ethyl)-4-iodobenzamide (0.075 g; 0.176 mmol), 2-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 1 to 20% ethyl acetate in dichloromethane) furnished 0.062 g (87%) of N-(2-(5-chloro-1H-indol-3-yl)ethyl)-2'-methoxybiphenyl-4-carboxamide.
ESI/APCI(+): 405 (M+H), 427 (M+Na); ESI/APCI(−): 403 (M−H).

Example 12

Preparation of N-(2-(5-chloro-1H-indol-3-yl)ethyl)-3'-methoxybiphenyl-2-carboxamide N-(2-(5-chloro-1H-indol-3-yl)ethyl)-3'-methoxybiphenyl-2-carboxamide was prepared according to method B with N-(2-(5-chloro-1H-indol-3-yl)ethyl)-2-iodobenzamide (0.075 g; 0.176 mmol), 3-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 1 to 20% ethyl acetate in dichloromethane) furnished 0.060 g (83%) of N-(2-(5-chloro-1H-indol-3-yl)ethyl)-3'-methoxybiphenyl-2-carboxamide as a white solid.
ESI/APCI(+): 405 (M+H), 427 (M+Na); ESI/APCI(−): 403 (M−H).

Example 13

Preparation of N-(2-(5-chloro-1H-indol-3-yl)ethyl)-3'-methoxybiphenyl-3-carboxamide N-(2-(5-chloro-1H-indol-3-yl)ethyl)-3'-methoxybiphenyl-3-carboxamide was prepared according to method B with N-(2-(5-chloro-1H-indol-3-yl)ethyl)-3-iodobenzamide (0.075 g; 0.176 mmol), 3-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 1 to 20% ethyl acetate in dichloromethane) furnished 0.062 g (87%) of N-(2-(5-chloro-1H-indol-3-yl)ethyl)-3'-methoxybiphenyl-3-carboxamide as a white solid.
ESI/APCI(+): 405 (M+H), 427 (M+Na); ESI/APCI(−): 403 (M−H).

Example 14

Preparation of N-(2-(5-chloro-1H-indol-3-yl)ethyl)-3'-methoxybiphenyl-4-carboxamide N-(2-(5-chloro-1H-indol-3-yl)ethyl)-3'-methoxybiphenyl-4-carboxamide was prepared according to method B with N-(2-(5-chloro-1H-indol-3-yl)ethyl)-4-iodobenzamide (0.075 g; 0.176 mmol), 3-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.052 g (73%) of N-(2-(5-chloro-1H-indol-3-yl)ethyl)-3'-methoxybiphenyl-4-carboxamide as a white solid.
ESI/APCI(+): 405 (M+H), 427 (M+Na); ESI/APCI(−): 403 (M−H).

Example 15

Preparation of N-(2-(5-chloro-1H-indol-3-yl)ethyl)-4'-methoxybiphenyl-2-carboxamide N-(2-(5-chloro-1H-indol-3-yl)ethyl)-4'-methoxybiphenyl-2-carboxamide was prepared according to method B with N-(2-(5-chloro-1H-indol-3-yl)ethyl)-2-iodobenzamide (0.075 g; 0.176 mmol), 4-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.067 g (94%) of N-(2-(5-chloro-1H-indol-3-yl)ethyl)-4'-methoxybiphenyl-2-carboxamide as a white solid.

ESI/APCI(+): 405 (M+H), 427 (M+Na); ESI/APCI(−): 403 (M−H).

Example 16

Preparation of N-(2-(5-chloro-1H-indol-3-yl)ethyl)-4'-methoxybiphenyl-3-carboxamide N-(2-(5-chloro-1H-indol-3-yl)ethyl)-4'-methoxybiphenyl-3-carboxamide was prepared according to method B with N-(2-(5-chloro-1H-indol-3-yl)ethyl)-3-iodobenzamide (0.075 g; 0.176 mmol), 4-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.057 g (80%) of N-(2-(5-chloro-1H-indol-3-yl)ethyl)-4'-methoxybiphenyl-3-carboxamide as a white solid.

ESI/APCI(+): 405 (M+H), 427 (M+Na); ESI/APCI(−): 403 (M−H).

Example 17

Preparation of N-(2-(5-chloro-1H-indol-3-yl)ethyl)-4'-methoxybiphenyl-4-carboxamide N-(2-(5-chloro-1H-indol-3-yl)ethyl)-4'-methoxybiphenyl-4-carboxamide was prepared according to method B with N-(2-(5-chloro-1H-indol-3-yl)ethyl)-4-iodobenzamide (0.075 g; 0.176 mmol), 4-methoxyphenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.047 g (66%) of N-(2-(5-chloro-1H-indol-3-yl)ethyl)-4'-methoxybiphenyl-4-carboxamide as a white solid.

ESI/APCI(+): 405 (M+H), 427 (M+Na); ESI/APCI(−): 403 (M−H).

Example 18

Preparation of N-(2-(5-chloro-1H-indol-3-yl)ethyl)-2'-fluorobiphenyl-2-carboxamide N-(2-(5-chloro-1H-indol-3-yl)ethyl)-2'-fluorobiphenyl-2-carboxamide was prepared according to method B with N-(2-(5-chloro-1H-indol-3-yl)ethyl)-2-iodobenzamide (0.075 g; 0.176 mmol), 2-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. The crude material was purified by flash chromatography on silica gel (eluent 2 to 20% ethyl acetate in dichloromethane) furnished 0.053 g (77%) of N-(2-(5-chloro-1H-indol-3-yl)ethyl)-2'-fluorobiphenyl-2-carboxamide as a white solid.

ESI/APCI(+): 393 (M+H), 415 (M+Na); ESI/APCI(−): 391 (M−H).

Example 19

Preparation of N-(2-(5-chloro-1H-indol-3-yl)ethyl)-2'-fluorobiphenyl-3-carboxamide N-(2-(5-chloro-1H-indol-3-yl)ethyl)-2'-fluorobiphenyl-3-carboxamide was prepared according to method B with N-(2-(5-chloro-1H-indol-3-yl)ethyl)-3-iodobenzamide (0.075 g; 0.176 mmol), 2-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.051 g (73%) of N-(2-(5-chloro-1H-indol-3-yl)ethyl)-2'-fluorobiphenyl-3-carboxamide as a white solid.

ESI/APCI(+): 393 (M+H), 415 (M+Na); ESI/APCI(−): 391 (M−H).

Example 20

Preparation of N-(2-(5-chloro-1H-indol-3-yl)ethyl)-2'-fluorobiphenyl-4-carboxamide N-(2-(5-chloro-1H-indol-3-yl)ethyl)-2'-fluorobiphenyl-4-carboxamide was prepared according to method B with N-(2-(5-chloro-1H-indol-3-yl)ethyl)-4-iodobenzamide (0.075 g; 0.176 mmol), 2-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.048 g (69%) of N-(2-(5-chloro-1H-indol-3-yl)ethyl)-2'-fluorobiphenyl-4-carboxamide as a white solid.

ESI/APCI(+): 393 (M+H), 415 (M+Na); ESI/APCI(−): 391 (M−H).

Example 21

Preparation of N-(2-(5-chloro-1H-indol-3-yl)ethyl)-3'-fluorobiphenyl-2-carboxamide N-(2-(5-chloro-1H-indol-3-yl)ethyl)-3'-fluorobiphenyl-2-carboxamide was prepared according to method B with N-(2-(5-chloro-1H-indol-3-yl)ethyl)-2-iodobenzamide (0.075 g; 0.176 mmol), 3-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.051 g (74%) of N-(2-(5-chloro-1H-indol-3-yl)ethyl)-3'-fluorobiphenyl-2-carboxamide as a white solid.

ESI/APCI(+): 393 (M+H), 415 (M+Na); ESI/APCI(−): 391 (M−H).

Example 22

Preparation of N-(2-(5-chloro-1H-indol-3-yl)ethyl)-3'-fluorobiphenyl-3-carboxamide N-(2-(5-chloro-1H-indol-3-yl)ethyl)-3'-fluorobiphenyl-3-carboxamide was prepared according to method B with N-(2-(5-chloro-1H-indol-3-yl)ethyl)-3-iodobenzamide (0.075 g; 0.176 mmol), 3-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.044 g (63%) of N-(2-(5-chloro-1H-indol-3-yl)ethyl)-3'-fluorobiphenyl-3-carboxamide as a white solid.
ESI/APCI(+): 393 (M+H); ESI/APCI(−): 391 (M−H).

Example 23

Preparation of N-(2-(5-chloro-1H-indol-3-yl)ethyl)-3'-fluorobiphenyl-4-carboxamide N-(2-(5-chloro-1H-indol-3-yl)ethyl)-3'-fluorobiphenyl-4-carboxamide was prepared according to method B with N-(2-(5-chloro-1H-indol-3-yl)ethyl)-4-iodobenzamide (0.075 g; 0.176 mmol), 3-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.059 g (85%) of N-(2-(5-chloro-1H-indol-3-yl)ethyl)-3'-fluorobiphenyl-4-carboxamide as a white solid.
ESI/APCI(+): 393 (M+H); ESI/APCI(−): 391 (M−H).

Example 24

Preparation of N-(2-(5-chloro-1H-indol-3-yl)ethyl)-4'-fluorobiphenyl-2-carboxamide N-(2-(5-chloro-1H-indol-3-yl)ethyl)-4'-fluorobiphenyl-2-carboxamide was prepared according to method B with N-(2-(5-chloro-1H-indol-3-yl)ethyl)-2-iodobenzamide (0.075 g; 0.176 mmol), 4-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.058 g (84%) of N-(2-(5-chloro-1H-indol-3-yl)ethyl)-4'-fluorobiphenyl-2-carboxamide as a white solid.
ESI/APCI(+): 393 (M+H), 415 (M+Na); ESI/APCI(−): 391 (M−H).

Example 25

Preparation of N-(2-(5-chloro-1H-indol-3-yl)ethyl)-4'-fluorobiphenyl-3-carboxamide N-(2-(5-chloro-1H-indol-3-yl)ethyl)-4'-fluorobiphenyl-2-carboxamide was prepared according to method B with N-(2-(5-chloro-1H-indol-3-yl)ethyl)-3-iodobenzamide (0.075 g; 0.176 mmol), 4-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.053 g (76%) of N-(2-(5-chloro-1H-indol-3-yl)ethyl)-4'-fluorobiphenyl-3-carboxamide as a white solid.
ESI/APCI(+): 393 (M+H), 415 (M+Na), 431 (M+K); ESI/APCI(−): 391 (M−H).

Example 26

Preparation of N-(2-(5-chloro-1H-indol-3-yl)ethyl)-4'-fluorobiphenyl-4-carboxamide N-(2-(5-chloro-1H-indol-3-yl)ethyl)-4'-fluorobiphenyl-4-carboxamide was prepared according to method B with N-(2-(5-chloro-1H-indol-3-yl)ethyl)-4-iodobenzamide (0.075 g; 0.176 mmol), 4-fluorophenylboronic acid (0.026 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.044 g (63%) of N-(2-(5-chloro-1H-indol-3-yl)ethyl)-4'-fluorobiphenyl-4-carboxamide as a white solid.
ESI/APCI(+): 393 (M+H), 415 (M+Na); ESI/APCI(−): 391 (M−H).

Example 27

Preparation of N-(2-(5-chloro-1H-indol-3-yl)ethyl)-2'-cyanobiphenyl-3-carboxamide N-(2-(5-chloro-1H-indol-3-yl)ethyl)-2'-cyanobiphenyl-3-carboxamide was prepared according to method B with N-(2-(5-chloro-1H-indol-3-yl)ethyl)-3-iodobenzamide (0.075 g; 0.176 mmol), 2-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.033 g (46%) of N-(2-(5-chloro-1H-indol-3-yl)ethyl)-2'-cyanobiphenyl-3-carboxamide as a white solid.
ESI/APCI(+): 400 (M+H), 422 (M+Na); ESI/APCI(−): 398 (M−H).

Example 28

Preparation of N-(2-(5-chloro-1H-indol-3-yl)ethyl)-2'-cyanobiphenyl-4-carboxamide N-(2-(5-chloro-1H-indol-3-yl)ethyl)-2'-cyanobiphenyl-4-carboxamide was prepared according to method B with N-(2-(5-chloro-1H-indol-3-yl)ethyl)-4-iodobenzamide (0.075 g; 0.176 mmol), 2-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.023 g (33%) of N-(2-(5-chloro-1H-indol-3-yl)ethyl)-2'-cyanobiphenyl-4-carboxamide as a white solid.
ESI/APCI(+): 400 (M+H), 422 (M+Na); ESI/APCI(−): 398 (M−H).

Example 29

Preparation of N-(2-(5-chloro-1H-indol-3-yl)ethyl)-3'-cyanobiphenyl-2-carboxamide N-(2-(5-chloro-1H-indol-3-yl)ethyl)-3'-cyanobiphenyl-2-carboxamide was prepared according to method B with N-(2-(5-chloro-1H-indol-3-yl)ethyl)-2-iodobenzamide (0.075 g; 0.176 mmol), 3-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.036 g (51%) of N-(2-(5-chloro-1H-indol-3-yl)ethyl)-3'-cyanobiphenyl-2-carboxamide as a white solid.
ESI/APCI(+): 400 (M+H), 422 (M+Na); ESI/APCI(−): 398 (M−H).

Example 30

Preparation of N-(2-(5-chloro-1H-indol-3-yl)ethyl)-3'-cyanobiphenyl-3-carboxamide N-(2-(5-chloro-1H-indol-3-yl)ethyl)-3'-cyanobiphenyl-3-carboxamide was prepared according to method B with N-(2-(5-chloro-1H-indol-3-yl)ethyl)-3-iodobenzamide (0.075 g; 0.176 mmol), 3-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.035 g (49%) of N-(2-(5-chloro-1H-indol-3-yl)ethyl)-3'-cyanobiphenyl-3-carboxamide compound as a white solid.
ESI/APCI(+): 400 (M+H), 422 (M+Na); ESI/APCI(−): 398 (M−H).

Example 31

Preparation of N-(2-(5-chloro-1H-indol-3-yl)ethyl)-3'-cyanobiphenyl-4-carboxamide N-(2-(5-chloro-1H-indol-3-yl)ethyl)-3'-cyanobiphenyl-4-carboxamide was prepared according to method B with N-(2-(5-chloro-1H-indol-3-yl)ethyl)-4-iodobenzamide (0.075 g; 0.176 mmol), 3-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.022 g (31%) of N-(2-(5-chloro-1H-indol-3-yl)ethyl)-3'-cyanobiphenyl-4-carboxamide as a white solid.
ESI/APCI(+):422 (M+Na); ESI/APCI(−): 398 (M−H).

Example 32

Preparation of N-(2-(5-chloro-1H-indol-3-yl)ethyl)-4'-cyanobiphenyl-2-carboxamide N-(2-(5-chloro-1H-indol-3-yl)ethyl)-4'-cyanobiphenyl-2-carboxamide was prepared according to method B with N-(2-(5-chloro-1H-indol-3-yl)ethyl)-2-iodobenzamide (0.075 g; 0.176 mmol), 4-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.032 g (46%) of N-(2-(5-chloro-1H-indol-3-yl)ethyl)-4'-cyanobiphenyl-2-carboxamide as a white solid.
ESI/APCI(+):422 (M+Na); ESI/APCI(−): 398 (M−H).

Example 33

Preparation of N-(2-(5-chloro-1H-indol-3-yl)ethyl)-4'-cyanobiphenyl-3-carboxamide N-(2-(5-chloro-1H-indol-3-yl)ethyl)-4'-cyanobiphenyl-3-carboxamide was prepared according to method B with N-(2-(5-chloro-1H-indol-3-yl)ethyl)-3-iodobenzamide (0.075 g; 0.176 mmol), 4-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.017 g (24%) of N-(2-(5-chloro-1H-indol-3-yl)ethyl)-4'-cyanobiphenyl-3-carboxamide as a white solid.
ESI/APCI(+): 400 (M+H), 422 (M+Na); ESI/APCI(−): 398 (M−H).

Example 34

Preparation of N-(2-(5-chloro-1H-indol-3-yl)ethyl)-4'-cyanobiphenyl-4-carboxamide N-(2-(5-chloro-1H-indol-3-yl)ethyl)-4'-cyanobiphenyl-4-carboxamide was prepared according to method B with N-(2-(5-chloro-1H-indol-3-yl)ethyl)-4-iodobenzamide (0.075 g; 0.176 mmol), 4-cyanophenylboronic acid (0.027 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 20% ethyl acetate in dichloromethane) furnished 0.034 g (48%) of N-(2-(5-chloro-1H-indol-3-yl)ethyl)-4'-cyanobiphenyl-4-carboxamide as a white solid.
ESI/APCI(+): 400 (M+H), 422 (M+Na); ESI/APCI(−): 398 (M−H).

Example 35

Preparation of 2'-chloro-N-(2-(5-chloro-1H-indol-3-yl)ethyl)biphenyl-2-carboxamide 2'-chloro-N-(2-(5-chloro-1H-indol-3-yl)ethyl)biphenyl-2-carboxamide was prepared according to method B with N-(2-(5-chloro-1H-indol-3-yl)ethyl)-2-iodobenzamide (0.075 g; 0.176 mmol), 2-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.043 g (60%) of 2'-chloro-N-(2-(5-chloro-1H-indol-3-yl)ethyl)biphenyl-2-carboxamide as a white solid.

ESI/APCI(+): 431 (M+Na); ESI/APCI(−): 407 (M−H).

Example 36

Preparation of 2'-chloro-N-(2-(5-chloro-1H-indol-3-yl)ethyl)biphenyl-3-carboxamide 2'-chloro-N-(2-(5-chloro-1H-indol-3-yl)ethyl)biphenyl-3-carboxamide was prepared according to method B with N-(2-(5-chloro-1H-indol-3-yl)ethyl)-3-iodobenzamide (0.075 g; 0.176 mmol), 2-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.051 g (70%) of 2'-chloro-N-(2-(5-chloro-1H-indol-3-yl)ethyl)biphenyl-3-carboxamide as a white solid.

ESI/APCI(+): 431 (M+Na); ESI/APCI(−): 407 (M−H).

Example 37

Preparation of 2'-chloro-N-(2-(5-chloro-1H-indol-3-yl)ethyl)biphenyl-4-carboxamide 2'-chloro-N-(2-(5-chloro-1H-indol-3-yl)ethyl)biphenyl-4-carboxamide was prepared according to method B with N-(2-(5-chloro-1H-indol-3-yl)ethyl)-4-iodobenzamide (0.075 g; 0.176 mmol), 2-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.060 g (82%) of 2'-chloro-N-(2-(5-chloro-1H-indol-3-yl)ethyl)biphenyl-4-carboxamide as a white solid.

ESI/APCI(+): 409 (M+H), 431 (M+Na); ESI/APCI(−): 407 (M−H).

Example 38

Preparation of 3'-chloro-N-(2-(5-chloro-1H-indol-3-yl)ethyl)biphenyl-2-carboxamide 3'-chloro-N-(2-(5-chloro-1H-indol-3-yl)ethyl)biphenyl-2-carboxamide was prepared according to method B with N-(2-(5-chloro-1H-indol-3-yl)ethyl)-2-iodobenzamide (0.075 g; 0.176 mmol), 2-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.032 g (44%) of 3'-chloro-N-(2-(5-chloro-1H-indol-3-yl)ethyl)biphenyl-2-carboxamide as a white solid.

ESI/APCI(+):409 (M+H), 431 (M+Na); ESI/APCI(−): 407 (M−H).

Example 39

Preparation of 3'-chloro-N-(2-(5-chloro-1H-indol-3-yl)ethyl)biphenyl-3-carboxamide 3'-chloro-N-(2-(5-chloro-1H-indol-3-yl)ethyl)biphenyl-3-carboxamide was prepared according to method B with N-(2-(5-chloro-1H-indol-3-yl)ethyl)-3-iodobenzamide (0.075 g; 0.176 mmol), 3-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.048 g (66%) of 3'-chloro-N-(2-(5-chloro-1H-indol-3-yl)ethyl)biphenyl-3-carboxamide as a white solid.

ESI/APCI(+): 409 (M+H), 431 (M+Na); ESI/APCI(−): 407 (M−H).

Example 40

Preparation of 3'-chloro-N-(2-(5-chloro-1H-indol-3-yl)ethyl)biphenyl-4-carboxamide 3'-chloro-N-(2-(5-chloro-1H-indol-3-yl)ethyl)biphenyl-4-carboxamide was prepared according to method B with N-(2-(5-chloro-1H-indol-3-yl)ethyl)-4-iodobenzamide (0.075 g; 0.176 mmol), 3-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.047 g (65%) of 3'-chloro-N-(2-(5-chloro-1H-indol-3-yl)ethyl)biphenyl-4-carboxamide as a white solid.

ESI/APCI(+): 409 (M+H), 431 (M+Na); ESI/APCI(−): 407 (M−H).

Example 41

Preparation of 4'-chloro-N-(2-(5-chloro-1H-indol-3-yl)ethyl)biphenyl-3-carboxamide 4'-chloro-N-(2-(5-chloro-1H-indol-3-yl)ethyl)biphenyl-3-carboxamide was prepared according to method B with N-(2-(5-chloro-1H-indol-3-yl)ethyl)-3-iodobenzamide (0.075 g; 0.176 mmol), 4-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.033 g (45%) of 4'-chloro-N-(2-(5-chloro-1H-indol-3-yl)ethyl)biphenyl-3-carboxamide as a white solid.

ESI/APCI(+): 409 (M+H).

Example 42

Preparation of 4'-chloro-N-(2-(5-chloro-1H-indol-3-yl)ethyl)biphenyl-4-carboxamide 4'-chloro-N-(2-(5-chloro-1H-indol-3-yl)ethyl)biphenyl-4-carboxamide was prepared according to method B with N-(2-(5-chloro-1H-indol-3-yl)ethyl)-4-iodobenzamide (0.075 g; 0.176 mmol), 4-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.029 g (40%) of 4'-chloro-N-(2-(5-chloro-1H-indol-3-yl)ethyl)biphenyl-4-carboxamide as a white solid.

ESI/APCI(+): 409 (M+H).

Example 43

Preparation of 4'-chloro-N-(2-(5-chloro-1H-indol-3-yl)ethyl)biphenyl-2-carboxamide 4'-chloro-N-(2-(5-chloro-1H-indol-3-yl)ethyl)biphenyl-2-carboxamide was prepared according to method B with N-(2-(5-chloro-1H-indol-3-yl)ethyl)-2-iodobenzamide (0.075 g; 0.176 mmol), 4-chlorophenylboronic acid (0.029 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.036 g (50%) of 4'-chloro-N-(2-(5-chloro-1H-indol-3-yl)ethyl)biphenyl-2-carboxamide as a white solid.

ESI/APCI(+): 431 (M+Na); ESI/APCI(−): 407 (M−H).

Example 44

Preparation of N-(2-(5-chloro-1H-indol-3-yl)ethyl)-3'-(trifluoromethyl)biphenyl-2-carboxamide N-(2-(5-chloro-1H-indol-3-yl)ethyl)-3'-(trifluoromethyl)biphenyl-2-carboxamide was prepared according to method B with N-(2-(5-chloro-1H-indol-3-yl)ethyl)-2-iodobenzamide (0.075 g; 0.176 mmol), 3-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.047 g (60%) of N-(2-(5-chloro-1H-indol-3-yl)ethyl)-3'-(trifluoromethyl)biphenyl-2-carboxamide as a white solid.

ESI/APCI(+): 443 (M+H) 465 (M+Na); ESI/APCI(−): 441 (M−H).

Example 45

Preparation of N-(2-(5-chloro-1H-indol-3-yl)ethyl)-2'-(trifluoromethyl)biphenyl-4-carboxamide N-(2-(5-chloro-1H-indol-3-yl)ethyl)-2'-(trifluoromethyl)biphenyl-4-carboxamide was prepared according to method B with N-(2-(5-chloro-1H-indol-3-yl)ethyl)-4-iodobenzamide (0.075 g; 0.176 mmol), 2-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.031 g (40%) of N-(2-(5-chloro-1H-indol-3-yl)ethyl)-2'-(trifluoromethyl)biphenyl-4-carboxamide as a white solid.

ESI/APCI(+): 443 (M+H); ESI/APCI(−): 441 (M−H).

Example 46

Preparation of N-(2-(5-chloro-1H-indol-3-yl)ethyl)-2'-(trifluoromethyl)biphenyl-3-carboxamide N-(2-(5-chloro-1H-indol-3-yl)ethyl)-3'-(trifluoromethyl)biphenyl-2-carboxamide was prepared according to method B with N-(2-(5-chloro-1H-indol-3-yl)ethyl)-3-iodobenzamide (0.075 g; 0.176 mmol), 2-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.057 g (72%) of N-(2-(5-chloro-1H-indol-3-yl)ethyl)-2'-(trifluoromethyl)biphenyl-3-carboxamide as a white solid.

ESI/APCI(+): 443 (M+H) 465 (M+Na); ESI/APCI(−): 441 (M−H).

Example 47

Preparation of N-(2-(5-chloro-1H-indol-3-yl)ethyl)-3'-(trifluoromethyl)biphenyl-4-carboxamide N-(2-(5-chloro-1H-indol-3-yl)ethyl)-3'-(trifluoromethyl)biphenyl-4-carboxamide was prepared according to method B with N-(2-(5-chloro-1H-indol-3-yl)ethyl)-4-iodobenzamide (0.075 g; 0.176 mmol), 3-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.036 g (46%) of N-(2-(5-chloro-1H-indol-3-yl)ethyl)-3'-(trifluoromethyl)biphenyl-4-carboxamide as a white solid.

ESI/APCI(+): 443 (M+H) 465 (M+Na); ESI/APCI(−): 441 (M−H).

Example 48

Preparation of N-(2-(5-chloro-1H-indol-3-yl)ethyl)-4'-(trifluoromethyl)biphenyl-2-carboxamide N-(2-(5-chloro-1H-indol-3-yl)ethyl)-4'-(trifluoromethyl)biphenyl-2-carboxamide was prepared according to method B with N-(2-(5-chloro-1H-indol-3-yl)ethyl)-2-iodobenzamide (0.075 g; 0.176 mmol), 4-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.028 g (35%) of N-(2-(5-chloro-1H-indol-3-yl)ethyl)-4'-(trifluoromethyl)biphenyl-2-carboxamide as a white solid.

ESI/APCI(+): 443 (M+H) 465 (M+Na); ESI/APCI(−): 441 (M−H).

Example 49

Preparation of N-(2-(5-chloro-1H-indol-3-yl)ethyl)-4'-(trifluoromethyl)biphenyl-3-carboxamide N-(2-(5-chloro-1H-indol-3-yl)ethyl)-4'-(trifluoromethyl)biphenyl-3-carboxamide was prepared according to method B with N-(2-(5-chloro-1H-indol-3-yl)ethyl)-3-iodobenzamide (0.075 g; 0.176 mmol), 4-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 180° C. for 5 minutes. Flash chromatography on silica gel (eluent 10 to 80% ethyl acetate in heptane) furnished 0.029 g (37%) of N-(2-(5-chloro-1H-indol-3-yl)ethyl)-4'-(trifluoromethyl)biphenyl-3-carboxamide as a white solid.

ESI/APCI(+): 443 (M+H) 465 (M+Na); ESI/APCI(−): 441 (M−H).

Example 50

Preparation of N-(2-(5-chloro-1H-indol-3-yl)ethyl)-3'-(trifluoromethyl)biphenyl-3-carboxamide N-(2-(5-chloro-1H-indol-3-yl)ethyl)-4'-(trifluoromethyl)biphenyl-3-carboxamide was prepared according to method B with N-(2-(5-chloro-1H-indol-3-yl)ethyl)-3-iodobenzamide (0.075 g; 0.176 mmol), 3-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.016 g (20%) of N-(2-(5-chloro-1H-indol-3-yl)ethyl)-3'-(trifluoromethyl)biphenyl-3-carboxamide as a white solid.

ESI/APCI(+): 443 (M+H) 465 (M+Na); ESI/APCI(−): 441 (M−H).

Example 51

Preparation of N-(2-(5-chloro-1H-indol-3-yl)ethyl)-4'-(trifluoromethyl)biphenyl-4-carboxamide N-(2-(5-chloro-1H-indol-3-yl)ethyl)-4'-(trifluoromethyl)biphenyl-4-carboxamide was prepared according to method B with N-(2-(5-chloro-1H-indol-3-yl)ethyl)-4-iodobenzamide (0.075 g; 0.176 mmol), 4-(trifluoromethyl)phenylboronic acid (0.035 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.038 g (49%) of N-(2-(5-chloro-1H-indol-3-yl)ethyl)-4'-(trifluoromethyl)biphenyl-4-carboxamide as a white solid.

ESI/APCI(+): 443 (M+H), 465 (M+Na); ESI/APCI(−): 441 (M−H).

Example 52

Preparation of N-(2-(5-chloro-1H-indol-3-yl)ethyl)-2',6'-dimethylbiphenyl-3-carboxamide N-(2-(5-chloro-1H-indol-3-yl)ethyl)-2',6'-dimethylbiphenyl-3-carboxamide was prepared according to method B with N-(2-(5-chloro-1H-indol-3-yl)ethyl)-3-iodobenzamide (0.075 g; 0.176 mmol), 2,6-dimethyl phenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.034 g (47%) of N-(2-(5-chloro-1H-indol-3-yl)ethyl)-2',6'-dimethylbiphenyl-3-carboxamide as a white solid.

ESI/APCI(+): 403 (M+H) 425 (M+Na); ESI/APCI(−): 401 (M−H).

Example 53

Preparation of N-(2-(5-chloro-1H-indol-3-yl)ethyl)-2',6'-dimethylbiphenyl-4-carboxamide N-(2-(5-chloro-1H-indol-3-yl)ethyl)-2',6'-dimethylbiphenyl-4-carboxamide was prepared according to method B with N-(2-(5-chloro-1H-indol-3-yl)ethyl)-4-iodobenzamide (0.075 g; 0.176 mmol), 2,6-dimethyl phenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.034 g (47%) of N-(2-(5-chloro-1H-indol-3-yl)ethyl)-2',6'-dimethylbiphenyl-4-carboxamide as a white solid.

ESI/APCI(+): 403 (M+H) 425 (M+Na); ESI/APCI(−): 401 (M−H).

Example 54

Preparation of N-(2-(5-chloro-1H-indol-3-yl)ethyl)-3',4'-dimethylbiphenyl-2-carboxamide N-(2-(5-chloro-1H-indol-3-yl)ethyl)-3',4'-dimethylbiphenyl-2-carboxamide was prepared according to method B with N-(2-(5-chloro-1H-indol-3-yl)ethyl)-2-iodobenzamide (0.075 g; 0.176 mmol), 3,4-dimethyl phenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.045 g (63%) of N-(2-(5-chloro-1H-indol-3-yl)ethyl)-3',4'-dimethylbiphenyl-2-carboxamide as a white solid.

ESI/APCI(+): 403 (M+H) 425 (M+Na).

Example 55

Preparation of N-(2-(5-chloro-1H-indol-3-yl)ethyl)-3',4'-dimethylbiphenyl-3-carboxamide N-(2-(5-chloro-1H-indol-3-yl)ethyl)-3',4'-dimethylbiphenyl-3-carboxamide was prepared according to method B with N-(2-(5-chloro-1H-indol-3-yl)ethyl)-3-iodobenzamide (0.075 g; 0.176 mmol), 3,4-dimethyl phenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.032 g (45%) of N-(2-(5- chloro-1H-indol-3-yl)ethyl)-3',4'-dimethylbiphenyl-3-carboxamide as a white solid.

ESI/APCI(+): 403 (M+H); ESI/APCI(−): 401 (M−H).

Example 56

Preparation of N-(2-(5-chloro-1H-indol-3-yl)ethyl)-3',4'-dimethylbiphenyl-4-carboxamide N-(2-(5-chloro-1H-indol-3-yl)ethyl)-3',4'-dimethylbiphenyl-4-carboxamide was prepared according to method B with N-(2-(5-chloro-1H-indol-3-yl)ethyl)-4-iodobenzamide (0.075 g; 0.176 mmol), 3,4-dimethyl phenylboronic acid (0.028 g; 0.180 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 10 to 80% ethyl acetate in heptane) furnished 0.048 g (68%) of N-(2-(5-chloro-1H-indol-3-yl)ethyl)-3',4'-dimethylbiphenyl-4-carboxamide as a white solid.

ESI/APCI(+): 403 (M+H); ESI/APCI(−): 401 (M−H).

Example 57

Preparation of N-(2-(5-chloro-1H-indol-3-yl)ethyl)-2'-methylbiphenyl-2-carboxamide N-(2-(5-chloro-1H-indol-3-yl)ethyl)-2'-methylbiphenyl-2-carboxamide was prepared according to method B with N-(2-(5-chloro-1H-indol-3-yl)ethyl)-2-iodobenzamide (0.075 g; 0.176 mmol), o-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.043 g (63%) of N-(2-(5-chloro-1H-indol-3-yl)ethyl)-2'-methylbiphenyl-2-carboxamide as a white solid.

ESI/APCI(+): 389 (M+H); ESI/APCI(−): 387 (M−H).

Example 58

Preparation of N-(2-(5-chloro-1H-indol-3-yl)ethyl)-2'-methylbiphenyl-3-carboxamide N-(2-(5-chloro-1H-indol-3-yl)ethyl)-2'-methylbiphenyl-3-carboxamide was prepared according to method B with N-(2-(5-chloro-1H-indol-3-yl)ethyl)-3-iodobenzamide (0.075 g; 0.176 mmol), o-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.054 g (79%) of N-(2-(5-chloro-1H-indol-3-yl)ethyl)-2'-methylbiphenyl-3-carboxamide as a white solid.

ESI/APCI(+): 389 (M+H); ESI/APCI(−): 387 (M−H).
$^1$H NMR (DMSO-d$_6$) δ 11.04 (s, 1H); 8.66 (t, 1H); 7.85 (m; 1H); 7.79 (br s, 1H); 7.60 (d, 1H); 7.56-7.48 (m, 2H); 7.36-7.22 (m, 6H); 7.05 (dd, 1H); 3.51 (app q; 2H); 2.93 (t, 2H); 2.22 (s, 3H).

Example 59

Preparation of N-(2-(5-chloro-1H-indol-3-yl)ethyl)-2'-methylbiphenyl-4-carboxamide N-(2-(5-chloro-1H-indol-3-yl)ethyl)-2'-methylbiphenyl-4-carboxamide was prepared according to method B with N-(2-(5-chloro-1H-indol-3-yl)ethyl)-4-iodobenzamide (0.075 g; 0.176 mmol), o-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.047 g (68%) of N-(2-(5-chloro-1H-indol-3-yl)ethyl)-2'-methylbiphenyl-4-carboxamide as a white solid.

ESI/APCI(+): 389 (M+H); ESI/APCI(−): 387 (M−H).
$^1$H NMR (DMSO-d$_6$) δ 11.05 (s, 1H); 8.67 (br s, 1H) 7.91 (d, 2H); 7.63 (s, 1H); 7.44-7.05 (m, 8H); 7.06 (d, 1H); 3.55 (m, 2H); 2.95 (t; 2H); 2.42 (s; 3H).

Example 60

Preparation of N-(2-(5-chloro-1H-indol-3-yl)ethyl)-3'-methylbiphenyl-2-carboxamide N-(2-(5-chloro-1H-indol-3-yl)ethyl)-3'-methylbiphenyl-2-carboxamide was prepared according to method B with N-(2-(5-chloro-1H-indol-3-yl)ethyl)-2-iodobenzamide (0.075 g; 0.176 mmol), m-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.020 g (30%) of N-(2-(5-chloro-1H-indol-3-yl)ethyl)-3'-methylbiphenyl-2-carboxamide as a white solid.

ESI/APCI(+): 389 (M+H); ESI/APCI(−): 387 (M−H).

Example 61

Preparation of N-(2-(5-chloro-1H-indol-3-yl)ethyl)-3'-methylbiphenyl-3-carboxamide N-(2-(5-chloro-1H-indol-3-yl)ethyl)-3'-methylbiphenyl-3-carboxamide was prepared according to method B with N-(2-(5-chloro-1H-indol-3-yl)ethyl)-3-iodobenzamide (0.075 g; 0.176 mmol), m-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.057 g (83%) of N-(2-(5-chloro-1H-indol-3-yl)ethyl)-3'-methylbiphenyl-3-carboxamide as a white solid.

ESI/APCI(+): 389 (M+H); ESI/APCI(−): 387 (M−H).

Example 62

Preparation of N-(2-(5-chloro-1H-indol-3-yl)ethyl)-3'-methylbiphenyl-4-carboxamide N-(2-(5-chloro-1H-indol-3-yl)ethyl)-3'-methylbiphenyl-4-carboxamide was prepared according to method B with N-(2-(5-chloro-1H-indol-3-yl)ethyl)-4-iodobenzamide (0.075 g; 0.176 mmol), m-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.057 g (83%) of N-(2-(5-chloro-1H-indol-3-yl)ethyl)-3'-methylbiphenyl-4-carboxamide as a white solid.

ESI/APCI(+): 389 (M+H); ESI/APCI(−): 387 (M−H).
$^1$H NMR (DMSO-d$_6$) δ 11.05 (s, 1H); 8.67 (br s, 1H); 7.93 (d, 2H); 7.75 (d, 2H); 7.64 (s, 1H); 7.53 (m, 2H); 7.38 (m, 2H); 7.29 (s, 1H); 7.23 (d, 1H); 7.08 (d, 1H); 3.55 (m, 2H); 2.94 (t, 2H); 2.39 (s; 3H).

Example 63

Preparation of N-(2-(5-chloro-1H-indol-3-yl)ethyl)-4'-methylbiphenyl-2-carboxamide N-(2-(5-chloro-1H-indol-3-yl)ethyl)-4'-methylbiphenyl-2-carboxamide was prepared according to method B with N-(2-(5-chloro-1H-indol-3-yl)ethyl)-2-iodobenzamide (0.075 g; 0.176 mmol), p-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.048 g (70%) of N-(2-(5-chloro-1H-indol-3-yl)ethyl)-4'-methylbiphenyl-2-carboxamide as a white solid.

ESI/APCI(+): 389 (M+H); ESI/APCI(−): 387 (M−H).
$^1$H NMR (DMSO-d$_6$) δ 11.03 (s, 1H); 8.25 (t, 1H); 7.52 (s, 1H); 7.50-7.44 (m, 1H); 7.38-7.35 (m, 4H); 7.25 (d, 2H); 7.18 (s, 1H); 7.14-7.06 (m, 3H); 3.35 (m, 2H); 2.71 (t, 2H); 1.99 (s, 3H).

Example 64

Preparation of N-(2-(5-chloro-1H-indol-3-yl)ethyl)-4'-methylbiphenyl-3-carboxamide N-(2-(5-chloro-1H-indol-3-yl)ethyl)-4'-methylbiphenyl-3-carboxamide was prepared according to method B with N-(2-(5-chloro-1H-indol-3-yl)ethyl)-3-iodobenzamide (0.075 g; 0.176 mmol), p-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.056 g (82%) of N-(2-(5-chloro-1H-indol-3-yl)ethyl)-4'-methylbiphenyl-3-carboxamide as a white solid.

ESI/APCI(+): 389 (M+H); ESI/APCI(−): 387 (M−H).

Example 65

Preparation of N-(2-(5-chloro-1H-indol-3-yl)ethyl)-4'-methylbiphenyl-4-carboxamide N-(2-(5-chloro-1H-indol-3-yl)ethyl)-4'-methylbiphenyl-4-carboxamide was prepared according to method B with N-(2-(5-chloro-1H-indol-3-yl)ethyl)-4-iodobenzamide (0.075 g; 0.176 mmol), p-tolylboronic acid (0.025 g; 0.176 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 15 minutes. Flash chromatography on silica gel (eluent 2 to 10% ethyl acetate in dichloromethane) furnished 0.051 g (74%) of N-(2-(5-chloro-1H-indol-3-yl)ethyl)-4'-methylbiphenyl-4-carboxamide as a white solid.

ESI/APCI(+): 389 (M+H); ESI/APCI(−): 387 (M−H).

Example 66

Preparation of N-(2-(5-chloro-1H-indol-3-yl)ethyl)-4'-hydroxybiphenyl-2-carboxamide N-(2-(5-chloro-1H-indol-3-yl)ethyl)-4'-hydroxybiphenyl-2-carboxamide was prepared according to method B with N-(2-(5-chloro-1H-indol-3-yl)ethyl)-2-iodobenzamide (0.075 g; 0.176 mmol), 4-hydroxyphenylboronic acid (0.024 g; 0.177 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 18 minutes. Flash chromatography on silica gel (eluent 10 to 80% ethyl acetate in heptane) furnished 0.017 g (26%) of N-(2-(5-chloro-1H-indol-3-yl)ethyl)-4'-hydroxybiphenyl-2-carboxamide as a white solid.

ESI/APCI(+): 391 (M+H); ESI/APCI(−): 389 (M−H).
$^1$H NMR (DMSO-d$_6$) δ 11.04 (s, 1H); 9.48 (s, 1H); 8.18 (t, 1H); 7.56-71 (m, 2H); 7.44 (m, 1H); 7.35 (m, 3H); 7.21 (m, 3H); 7.07 (d, 1H); 6.77 (d, 2H); 3.34 (m, 2H); 2.72 (m, 2H).

Example 67

Preparation of N-(2-(5-chloro-1H-indol-3-yl)ethyl)-4'-hydroxybiphenyl-3-carboxamide N-(2-(5-chloro-1H-indol-3-yl)ethyl)-4'-hydroxybiphenyl-3-carboxamide was prepared according to method B with N-(2-(5-chloro-1H-indol-3-yl)ethyl)-3-iodobenzamide (0.075 g; 0.176 mmol), 4-hydroxyphenylboronic acid (0.024 g; 0.177 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 18 minutes. Flash chromatography on silica gel (eluent 10 to 80% ethyl acetate in heptane) furnished 0.010 g (14%) of N-(2-(5-chloro-1H-indol-3-yl)ethyl)-4'-hydroxybiphenyl-3-carboxamide as a white solid.

ESI/APCI(+): 391 (M+H); ESI/APCI(−): 389 (M−H).
$^1$H NMR (DMSO-d$_6$) δ 11.06 (s, 1H); 9.65 (s, 1H); 8.70 (t, 1H); 8.02 (s, 1H); 7.74 (t, 2H); 7.64 (s, 1H); 7.47-7.57 (m, 3H), 7.37 (d, 1H); 7.29 (s, 1H); 7.07 (d, 1H); 6.88 (d, 2H); 3.54 (m, 2H); 2.96 (m, 2H).

Example 68

Preparation of N-(2-(5-chloro-1H-indol-3-yl)ethyl)-4'-hydroxybiphenyl-4-carboxamide N-(2-(5-chloro-1H-indol-3-yl)ethyl)-4'-hydroxybiphenyl-4-carboxamide was prepared according to method B with N-(2-(5-chloro-1H-indol-3-yl)ethyl)-4-iodobenzamide (0.075 g; 0.176 mmol), 4-hydroxyphenylboronic acid (0.024 g; 0.177 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 18 minutes. Flash chromatography on silica gel (eluent 10 to 80% ethyl acetate in heptane) furnished 0.017 g (26%) of N-(2-(5-chloro-1H-indol-3-yl)ethyl)-4'-hydroxybiphenyl-4-carboxamide as a white solid.

ESI/APCI(+): 391 (M+H); ESI/APCI(−): 389 (M−H).

$^1$H NMR (DMSO-$d_6$) δ 11.04 (s, 1H); 9.68 (s, 1H); 8.61 (t, 1H); 7.87 (d, 2H); 7.65 (m, 3H); 7.57 (d, 2H); 7.35 (d, 1H); 7.29 (s, 1H); 7.05 (d, 1H); 6.86 (d, 2H); 3.52 (m, 2H); 2.93 (m, 2H).

Example 69

Preparation of N-(2-(5-chloro-1H-indol-3-yl)ethyl)-3-(pyridin-4-yl)benzamide

N-(2-(5-chloro-1H-indol-3-yl)ethyl)-3-(pyridin-4-yl)benzamide was prepared according to method B with N-(2-(5-chloro-1H-indol-3-yl)ethyl)-3-iodobenzamide (0.075 g; 0.176 mmol), pyridin-4-ylboronic acid (0.025 g; 0.177 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 18 minutes. Flash chromatography on silica gel (eluent 10 to 80% ethyl acetate in heptane) furnished 0.047 g (71%) of N-(2-(5-chloro-1H-indol-3-yl)ethyl)-3-(pyridin-4-yl)benzamide as a white solid.

ESI/APCI(+): 376 (M+H); ESI/APCI(−): 374 (M−H).

$^1$H NMR (DMSO-$d_6$) δ 11.05 (s, 1H); 8.78 (m, 1H); 8.68 (m, 2H); 8.21 (s, 1H); 7.95 (t, 2H); 7.76 (m, 2H); 7.64 (m, 2H); 7.35 (d, 1H); 7.29 (s, 1H); 7.05 (d, 1H); 3.55 (m, 2H); 2.96 (m, 2H).

Example 70

Preparation of N-(2-(5-chloro-1H-indol-3-yl)ethyl)-4-(pyridin-4-yl)benzamide

N-(2-(5-chloro-1H-indol-3-yl)ethyl)-4-(pyridin-4-yl)benzamide was prepared according to method B with N-(2-(5-chloro-1H-indol-3-yl)ethyl)-4-iodobenzamide (0.075 g; 0.176 mmol), pyridin-4-ylboronic acid (0.025 g; 0.177 mmol), tetrakis(triphenylphosphine)palladium (0.010 g; 0.009 mmol), sodium carbonate (0.037 g; 0.353 mmol), in dimethoxyethane (3 mL) and water (1 mL), irradiated in a microwave oven at 130° C. for 18 minutes. Flash chromatography on silica gel (eluent 10 to 80% ethyl acetate in heptane) furnished 0.051 g (77%) of N-(2-(5-chloro-1H-indol-3-yl)ethyl)-4-(pyridin-4-yl)benzamide as a white solid.

ESI/APCI(+): 376 (M+H); ESI/APCI(−): 374 (M−H).

$^1$H NMR (DMSO-$d_6$) δ 11.06 (s, 1H); 8.74 (m, 1H); 8.69 (m, 2H); 7.98 (m, 4H); 7.80 (m, 2H); 7.64 (s, 1H); 7.37 (d, 1H); 7.29 (s, 1H); 7.05 (d, 1H); 3.54 (m, 2H); 2.96 (m, 2H).

Example 71

Preparation N-(2-(5-Chloro-1H-indol-3-yl)ethyl)-2-(1H-pyrazol-1-yl)benzamide

A mixture of N-(2-(5-chloro-1H-indol-3-yl)ethyl)-2-iodobenzamide (0.080 g; 0.188 mmol), 1H-pyrazole (0.065 g; 0.942 mmol), copper (I) iodide (0.0036 g; 0.002 mmol), and potassium carbonate (0.032 g; 0.226 mmol) in 2-propanol (3 ml) was irradiated in a microwave oven microwave for 20 minutes at 150° C. The volatiles were removed under reduced pressure and the residue was partitioned between water and ethyl acetate. The aqueous layer was then extracted several times with ethyl acetate. The combined organic layers were evaporated to dryness and the residue was purified by flash chromatography on silica gel (eluent 1 to 10% methanol in dichloromethane) to afford 0.028 g (41%) of N-(2-(5-Chloro-1H-indol-3-yl)ethyl)-2-(1H-pyrazol-1-yl)benzamide as a white solid.

ESI/APCI(+): 365 (M+H); ESI/APCI(−): 363 (M−H).

Example 72

Preparation of N-(2-(5-chloro-1H-indol-3-yl)ethyl)-6-phenylpyridazine-3-carboxamide A mixture of phenylboronic acid (0.022 g; 0.179 mmol), 6-chloro-N-(2-(5-chloro-1H-indol-3-yl)ethyl)pyridazine-3-carboxamide (0.050 g; 0.149 mmol), [1,1'-Bis(diphenylphosphino)ferrocene]palladium(II) chloride (0.012 g; 0.015 mmol), sodium iodide (0.044 g; 0.298 mmol) and sodium carbonate (0.032 g; 0.298 mmol) in dimethoxyethane (3 mL) and water (1 mL) was irradiated in the microwave oven at 130° C. for 15 minutes. The resulting solution was reported between water and ethyl acetate and the organic layer was concentrated under reduced pressure. The crude material was purified by flash chromatography on silica gel (eluent 20 to 80% ethyl acetate in heptane) to afford 0.0038 g (7%) of N-(2-(5-chloro-1H-indol-3-yl)ethyl)-6-phenylpyridazine-3-carboxamide as a white solid.

ESI/APCI(+): 377 (M+H); ESI/APCI(−): 375 (M−H).

It is known to the skilled in the art that many additional compounds of the invention can be prepared with the same procedures as described herein. Additional examples of such other compounds of present invention include: 2-(1H-pyrazol-1-yl)-N-(2-(5-(trifluoromethyl)-1H-indol-3-yl)ethyl)benzamide; 3-(pyridin-3-yl)-N-(2-(5-(trifluoromethyl)-1H-indol-3-yl)ethyl)benzamide; 4-(furan-2-yl)-N-(2-(5-(trifluoromethyl)-1H-indol-3-yl)ethyl)benzamide; N-(2-(5-cyano-1H-indol-3-yl)ethyl)-3'-fluorobiphenyl-2-carboxamide; N-(2-(5-cyano-1H-indol-3-yl)ethyl)-3-(1H-imidazol-5-yl)benzamide; N-(2-(5-cyano-1H-indol-3-yl)ethyl)-4-(thiophen-3-yl)benzamide; N-(2-(5,6-dichloro-1H-indol-3-yl)ethyl)-2-(1H-pyrazol-1-yl)benzamide; N-(2-(5,6-dichloro-1H-indol-3-yl)ethyl)-2'-methylbiphenyl-3-carboxamide; N-(2-(5,6-dichloro-1H-indol-3-yl)ethyl)-4-(pyridin-4-yl)benzamide; 3'-chloro-N-(2-(6-chloro-5-methyl-1H-indol-3-yl)ethyl)biphenyl-2-carboxamide; N-(2-(6-chloro-5-methyl-1H-indol-3-yl)ethyl)-2'-cyanobiphenyl-3-carboxamide; N-(2-(6-chloro-5-methyl-1H-indol-3-yl)ethyl)-4-(pyridin-2-yl)benzamide; N-(2-(5-acetyl-1H-indol-3-yl)ethyl)-2-(oxazol-5-yl)benzamide; N-(2-(5-acetyl-1H-indol-3-yl)ethyl)-4'-hydroxybiphenyl-3-carboxamide; N-(2-(5-acetyl-1H-indol-3-yl)ethyl)-2'-chlorobiphenyl-4-carboxamide; N-(2-(5-chloro-1H-pyrrolo[2,3-b]pyridin-3-yl)ethyl)-2-(oxazol-2-yl)benzamide; N-(2-(5-chloro-1H-pyrrolo[2,3-b]pyridin-3-yl)ethyl)-3'-hydroxybiphenyl-3-carboxamide; N-(2-(5-chloro-1H-pyrrolo[2,3-b]pyridin-3-yl)ethyl)-4-(thiophen-2-yl)benzamide; N-(2-(5-chloro-1H-indol-3-yl)ethyl)-2-(thiophen-3-yl)benzamide; N-(2-(5-chloro-1H-indol-3-yl)ethyl)-3-(pyridin-2-yl)benzamide; N-(2-(5-chloro-1H-indol-3-yl)ethyl)-4-(oxazol-2-yl)benzamide; N-(2-(5-chloro-1H-indol-3-yl)ethyl)-6-(pyridin-3-yl)pyridazine-3-carboxamide; N-(2-(6-chloro-5-methyl-1H-indol-3-yl)ethyl)-6-(1-methyl-1H-pyrazol-4-yl)pyridazine-3-carboxamide; N-((5-chloro-1H-indol-3-yl)methyl)-3'-fluorobiphenyl-3-carboxamide; N-((5-chloro-1H-indol-3-yl)methyl)-4-(oxazol-5-yl)benzamide; N-((5-chloro-1H-indol-3-yl)methyl)-6-(pyridin-4-yl)pyridazine-3-carboxamide; N-(3-(5-chloro-1H-indol-3-yl)propyl)-2-(1H-pyrazol-1-yl)

benzamide; N-(3-(5-chloro-1H-indol-3-yl)propyl)-3'-fluorobiphenyl-3-carboxamide; N-(3-(5-chloro-1H-indol-3-yl)propyl)-4-(oxazol-2-yl)benzamide.

Part B

Example 73

Construction of a TAU Gene Over-Expressing Cell Line

A TAU expression plasmid was constructed by sub-cloning the cDNA of human TAU-P301L (encoding for TAU with proline 301 substituted by a leucine residue) into mammalian expression vector pcDNA3.1 resulting in plasmid pcDNA3.1-TAU P301L. Plasmids pcDNA3.1 and pcDNA3.1-TAU P301L were transfected to human neuroblastoma cells (BM17; ATCC No. CRL-2267) and independent clonal lines with the plasmids stably integrated into the genome were selected. These resulted in cell lines named M17-3.1 and M17-TAU(P301L) (transfected with pcDNA3.1 and pcDNA3.1-TAU P301L, respectively). Expression of the TAU P301L genes in the cell lines was confirmed by Western analysis.

Example 74

Use of TAU Expressing Cells as a Model of Neuronal Degradation

The expression of TAU P301L in M17-TAU(P301L) cells was found to confer increased toxicity relative to control cells expressing wild type TAU (M17-TAUwt). In degenerated or dead cells lactate dehydrogenase (LDH) is leaked out of the cells into the extracellular environment due to a loss of plasma-membrane integrity. This principle was used to determine cytotoxicity by quantifying the level of leaked LDH into the growth medium.

The detailed method for determining TAU cytotoxicity was as follows: From appropriate precultures of M17-3.1 and M17-TAU(P301L) cells were seeded at 2500 cells/cm2 in Optimem Reduced Serum without phenol red (Gibco, Cat. 31985-047) supplemented with 1% fetal calf serum, 1 mM sodium pyruvate, 1× non-essential amino acids, 500 µg/ml G418 0.5× antibiotic/antimycotic. After 3 h of incubation at 37° C./5% CO2 1 volume of Optimem Reduced Serum (same as described above; except without fetal calf serum) supplemented with 2.5 µM retinoic acid (RA) was added. The cells were further incubated for 7 days. Subsequently, LDH activity was determined using Promega Cytotox 96 Non-Radioactive cytotoxicity assay, (Cat. G1780) according the supplier's instructions. FIG. 1 shows that of M17-TAU P301L cells, but not of M17-3.1 cells display a relatively high level of LDH leaked into the medium demonstrating toxicity specifically provoked by TAU P301.

Example 75

Use of the TAU Expressing Cells for the Testing of Exemplary Compounds of this Invention The M17-TAU P301L cell line made it possible to assess the ability of novel compounds to counteract TAU cytotoxicity. Active inhibitors of TAU cytotoxicity were found to inhibit LDH leakage of M17-TAU P301L cells treated as described in Example 75 Efficacy (potency) of the compounds was determined by testing compounds at different concentrations ranging from non-effective (thus at a relatively low concentration) to an effective concentration for their ability to reduce LDH activity of retinoic acid incubated M17-TAU P301L cells. These measurements were used to calculate EC50 values of table 2.

Example 76

In-Vivo Inhibition of Pathological TAU-Phosphorylation

Human TAU R406W transgenic mice (Zhang et al, J. of Neuroscience 24(19):4657-4667, 2004) are treated once-a-day subcutaneously for 4 weeks with a compound of the invention (for example see table 1) dissolved in a formulation such as arachidin oil at a dose of for example 35 mg/kg. Correspondingly vehicle treated transgenics are included as controls. At the end of the treatment period mice are sacrificed and brainstem is stereotactically collected. Soluble protein fractions are prepared (Terwel et al, J Biol Chem 280(5): 3963-73, 2005) from the brain stem and subjected to Western analysis using antibodies directed against TAU and several different phospho-isoforms thereof.

Quantitative analysis of the Western blots can reveal that in treated animals a robust and statistically significant reduction is detected for TAU phosphorylated at certain amino acids which are phospho-epitopes (for example serine 202, tyrosine 205 or tyrosine 231) and are pathologically relevant for disease since in Alzheimer's disease patients TAU is hyperphosphorylated at and hyperphosphorylation at these sites has been implicated in aggregation and toxicity of TAU (Bertrand et al, Neuroscience 168(2):323-34, 2010; Luna-Muños et al, J Alzheimers Dis. 12(4):365-75, 2007, Augustinack et al, Acta Neuropathol. 103(1):26-35, 2002).

Example 77

In Vivo Inhibition of Tau-Instigated Pathologies

Human TAU R406W transgenic mice (J. of Neuroscience 24(19): 4657-4667, 2004) are chronically treated between 2 weeks and 12 months with either an exemplary compound of this invention or vehicle only. The compound treated mice possess a longer average lifespan and display a delayed onset or progression of motor weakness compared to the vehicle controls. In addition compound treated mice have improved learning and memory capabilities when performing the Morris water maze test.

At the end of the treatment period, mice are sacrificed and the corresponding brains are used for biochemical and immunohistochemical analysis. The brains of compound treated mice are heavier than brains of the control group. In compound treated mice Western analysis shows that TAU phosphorylation is reduced suggesting lowered formation of pathological TAU species. Also a reduced accumulation of TAU is found in the insoluble fraction of total brain extracts and/or the cerebral spine fluid (CSF) of compound treated mice. Immunohistochemical analysis showed that compound treated mice have reduced accumulation of filamentous TAU aggregates in cerebral cortex, hippocampus, cerebellum, and spinal cord neurons.

Example 78

Construction of an α-Synuclein Over-Expressing Cell Line

An α-synuclein expression plasmid was constructed by sub-cloning the NcoI/XhoI fragment from 212T-SYN(WT)

(Griffioen et al., Biochem Biophys Acta (2006) 1762(3):312-318) containing the cDNA of human wild type α-synuclein correspondingly into a standard mammalian expression vector pcDNA3.1 resulting in plasmid pcDNA3.1-SYNwt. Plasmid pcDNA3.1 and pcDNA3.1-SYNwt were transfected to human neuroblastoma cells (ATCC No. CRL-2267) and independent clonal lines with the plasmids stably integrated into the genome were selected. These resulted in cell lines named M17 (transfected with pcDNA3.1) and M17-SYNwt (transfected with pcDNA3.1-SYNwt). Over-expression of α-synuclein in M17-SYNwt cell lines was confirmed by Western analysis.

Example 79

Use of α-Synuclein Expressing Cells as a Model for Neuronal Degradation

Due to the high levels of α-synuclein M17-SYNwt cells are exquisitely sensitivity to paraquat, a well-known risk factor of synuclein-dependent neuronal degeneration. In degenerated or dead cells lactate dehydrogenase (LDH) is leaked out of the cells into the extracellular environment due to a loss of plasma-membrane integrity. This principle is used to determine cytotoxicity by quantifying the level of leaked LDH into the growth medium.

The detailed method for determining α-synuclein cytotoxicity is as follows: From appropriate precultures of M17 and M17-SYN cells are seeded at 50000 cells/cm$^2$ in Optimem Reduced Serum without phenol red (InVitrogen, Cat. 31985-047) supplemented with 5% fetal calf serum, 1 mM sodium pyruvate, 1× non-essential amino acids, 500 µg/ml G418 0.5× antibiotic/antimycotic. After 3 h of incubation at 37° C./5% $CO_2$ paraquat is added to the cells (final concentration of 32 mM), together with the test compound and the cells are further incubated for 40 hours. Subsequently, LDH activity is determined using Promega Cytotox 96 Non-Radioactive cytotoxicity assay, (Cat. G1780) according the supplier's instructions.

Figure 2:
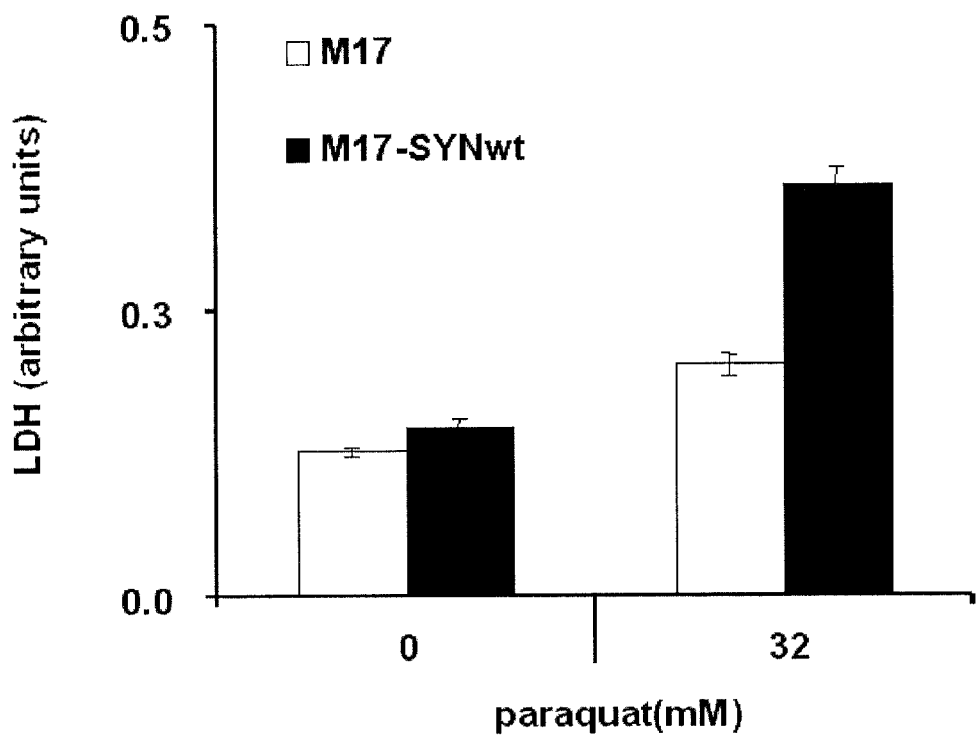
FIG. 2 shows the sensitivity of an α-synuclein expressing neuroblastoma cell line to paraquat.

FIG. 2 shows that treatment of M17-SYNwt cells, but not of M17 cells with paraquat led to a relatively high level of LDH leaked into the medium demonstrating that α-synuclein mediates cellular degeneration or cell death in response to paraquat.

Example 80

Use of the α-Synuclein Expressing Cells in Screening Compounds

This α-synuclein expressing neuroblastoma cells make it possible to assess the ability of novel compounds to counteract α-synuclein cytotoxicity. Active inhibitors of α-synuclein cytotoxicity are found to provoke a decrease of LDH leakage in paraquat-treated M17-SYNwt cells. Since this method monitors leaked LDH from degenerated or dead cells only non-toxic compounds will be identified as active inhibitors of α-synuclein-mediated cytotoxicity. Lack of toxicity is an important characteristic for compounds to be used as a medicament to patients in need. A compound is considered to be active in this test when it inhibits α-synuclein cytotoxicity by more than 25% relative to untreated M17-SYNwt cells at a concentration of 20 µg/mL or lower. In the experiments, the control group consists of M17-SYNwt cells treated with DMSO, the untreated paraquat group consists of M17-SYNwt cells treated with paraquat and DMSO, and the treated paraquat group consists of M17-SYNwt cells to be treated with paraquat and the test compound dissolved in DMSO.

In order to determine $EC_{50}$ compounds are tested at different concentrations ranging from non-effective (thus at a relatively low concentration) to an effective (relatively high) concentration of test compound. These data are also used for calculation of percent inhibition (% I). Percent inhibition is calculated as the synuclein toxicity inhibition by the compound in treated paraquat cells, relative to the synuclein cytotoxicity in untreated paraquat cells. This corresponds to the following equation:

(LDH release of treated paraquat cells at non-effective concentration of test cmpd)−(LDH release of treated paraquat cells at most effective concentration of test cmpd)/(LDH release of untreated paraquat cells)−(LDH release control cells)*100%

Example 81

Inhibition of Synuclein-Mediated Toxicity

The compounds are screened for activity using the α-synuclein cytotoxicity assay as described above. Dose responses are carried out on all compounds found to be active (10 point curves in duplicate).

Example 82

In Vivo Inhibition of Synuclein-Mediated Instigated Loss of Substantia Nigra Neurons In order to model neuronal loss in the substantia nigra region of the brain, mice are treated with paraquat (intraperitoneal) at a dose not higher than 8 mg/kg/day for a continuous period of 15-100 days. These mice are also chronically co-treated during that period with a compound from table 1 administered at a dose (probably not higher than 20 mg/kg body weight/day), or by vehicle only (no active compound). Mice treatment by means of vehicle or a compound of the invention start 2 days before administration of paraquat.

At the end of the treatment period, mice are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosin hydroxylase), tyrosine hydroxylase containing neurons in the brains are detected. Quantitative and comparative analysis of the tyrosin hydroxylase-positive stained substantia nigra areas reveal a significantly larger TH-positive area in mice treated with compound versus vehicle treated mice.

Example 83

In Vivo Inhibition of 6-Hydroxydopamine (6-OHDA) Instigated Loss of Substantia Nigra Neurons Unilateral substantia nigra lesions are obtained by stereotactic striatal injections of 6-hydroxydopamine in brains of living rats as described by Vercammen et al. in *Molecular Therapy*, 14(5) 716-723 (2006). These rats are also chronically co-treated with a compound of table 1 or by vehicle only (no active compound). Daily treatment of compound or vehicle is started preferably 1 or 2 days before administration of 6-OHDA and lasts between 7 to 30 days after the 6-OHDA injection.

At the end of the treatment period, rats are sacrificed and the corresponding brains are used for immunohistochemical analysis. The substantia nigra brain region has a relatively high percentage of cells with high levels of tyrosine hydroxylase. Using antibodies raised against tyrosin hydroxylase (anti-tyrosine hydroxylase) tyrosine hydroxylase containing neurons in the brains are detected. The nigral lesion volumes and/or the tyrosine hydroxylase positive cell numbers are quantified as described in Vercammen et al. (cited supra). This analysis reveals that:

- the nigral lesion volumes are significantly reduced in rats treated with a compound according to this invention, as compared to vehicle treated rats, thus indicating that the compound is able to inhibit 6-OHDA triggered degeneration of substantia nigra cells in vivo; and
- tyrosine hydroxylase positive cell numbers are higher in rats treated with a compound according to this invention as compared to vehicle treated rats, thus providing confirmation that the compound is able to inhibit 6-OHDA triggered degeneration of substantia nigra cells in vivo.

Example 84

In Vitro Inhibition of α-Synuclein Aggregation

α-Synucleinopathies are characterised by aggregation of α-synuclein in neurons. Aggregation of purified α-synuclein is performed essentially as described by Gerard et al. *FASEB*. 20(3):524-6 (2006). 20-100 µg purified α-synuclein (Sigma; S7820) at a concentration of about 2.5 µg/mL is incubated in the presence of spermin (250 µM) or paraquat (32 mM) or 6-hydroxydopamine (400 µM) or vehicle in a 384 well plate. Spermin, paraquat and 6-hydroxydopamine promote the α-synuclein aggregation process. Aggregation kinetics is determined by measuring turbidity at 340 nm, every 1-15 minutes for at least one hour. The same compounds, or vehicle only, is added to the different α-synuclein mixtures described above. This analysis reveals that, when a compound is present, the measured turbidity is lower compared to reactions containing vehicle only. This finding shows that the compound is able to inhibit aggregation of α-synuclein.

Exemplary compounds of the present invention are shown in table 2, with their chemical name and their $EC_{50}$ value (expressed in nM) as determined from example 75 in the Tau-induced toxicity experiment.

TABLE 2

| CODE | NAME | $EC_{50}$ (nM) |
|---|---|---|
| Cpd002 | N-(2-(5-chloro-1H-indol-3-yl)ethyl)biphenyl-4-carboxamide | 130 |
| Cpd003 | N-(2-(5-fluoro-1H-indol-3-yl)ethyl)biphenyl-4-carboxamide | 448 |
| Cpd004 | N-(2-(5-methyl-1H-indol-3-yl)ethyl)biphenyl-4-carboxamide | 238 |
| Cpd005 | ethyl 5-amino-1-(4-(2-(5-methyl-1H-indol-3-yl)ethylcarbamoyl)phenyl)-1H-pyrazole-4-carboxylate | 297 |
| Cpd006 | N-(2-(5-chloro-1H-indol-3-yl)ethyl)-2-morpholinoisonicotinamide | 876 |
| Cpd007 | N-(2-(5-fluoro-1H-indol-3-yl)ethyl)-2-morpholinoisonicotinamide | 1078 |
| Cpd008 | N-(2-(5-chloro-1H-indol-3-yl)ethyl)biphenyl-2-carboxamide | 249 |
| Cpd010 | N-(2-(5-chloro-1H-indol-3-yl)ethyl)biphenyl-3-carboxamide | 187 |

TABLE 2-continued

| CODE | NAME | $EC_{50}$ (nM) |
|---|---|---|
| Cpd011 | N-(2-(5-chloro-1H-indol-3-yDethyl)-2',6'-dimethylbiphenyl-4-carboxamide | 236 |
| Cpd013 | N-(2-(5-chloro-1H-indol-3-yl)ethyl)-4'-hydroxybiphenyl-3-carboxamide | 77 |
| Cpd014 | N-(2-(5-chloro-1H-indol-3-yl)ethyl)-4'-hydroxybiphenyl-4-carboxamide | 57 |
| Cpd015 | N-(2-(5-chloro-1H-indol-3-yl)ethyl)-2'-methylbiphenyl-2-carboxamide | 381 |
| Cpd019 | N-(2-(5-chloro-1H-indol-3-yl)ethyl)-3'-methylbiphenyl-3-carboxamide | 709 |
| Cpd021 | N-(2-(5-chloro-1H-indol-3-yl)ethyl)-4'-methylbiphenyl-2-carboxamide | 237 |
| Cpd022 | N-(2-(5-chloro-1H-indol-3-yl)ethyl)-4'-methylbiphenyl-3-carboxamide | 354 |
| Cpd023 | N-(2-(5-chloro-1H-indol-3-yl)ethyl)-4'-methylbiphenyl-4-carboxamide | 235 |
| Cpd024 | N-(2-(5-chloro-1H-indol-3-yl)ethyl)-6-morpholinonicotinamide | 765 |
| Cpd025 | N-(2-(5-chloro-1H-indol-3-yl)ethyl)-2-(1H-pyrazol-1-yl)benzamide | 760 |
| Cpd029 | N-(2-(5-chloro-1H-indol-3-yl)ethyl)-3'-methoxybiphenyl-2-carboxamide | 523 |
| Cpd032 | N-(2-(5-chloro-1H-indol-3-yl)ethyl)-4'-methoxybiphenyl-2-carboxamide | 200 |
| Cpd033 | N-(2-(5-chloro-1H-indol-3-yl)ethyl)-4'-methoxybiphenyl-3-carboxamide | 223 |
| Cpd034 | N-(2-(5-chloro-1H-indol-3-yl)ethyl)-4'-methoxybiphenyl-4-carboxamide | 91 |
| Cpd035 | N-(2-(5-chloro-1H-indol-3-yl)ethyl)-2'-fluorobiphenyl-2-carboxamide | 165 |
| Cpd036 | N-(2-(5-chloro-1H-indol-3-yl)ethyl)-2'-fluorobiphenyl-3-carboxamide | 139 |
| Cpd037 | N-(2-(5-chloro-1H-indol-3-yl)ethyl)-2'-fluorobiphenyl-4-carboxamide | 61 |
| Cpd038 | N-(2-(5-chloro-1H-indol-3-yl)ethyl)-3'-fluorobiphenyl-2-carboxamide | 226 |
| Cpd039 | N-(2-(5-chloro-1H-indol-3-yl)ethyl)-3'-fluorobiphenyl-4-carboxamide | 139 |
| Cpd040 | N-(2-(5-chloro-1H-indol-3-yl)ethyl)-4'-fluorobiphenyl-2-carboxamide | 208 |
| Cpd041 | N-(2-(5-chloro-1H-indol-3-yl)ethyl)-4'-fluorobiphenyl-3-carboxamide | 186 |
| Cpd042 | N-(2-(5-chloro-1H-indol-3-yl)ethyl)-4'-fluorobiphenyl-4-carboxamide | 228 |
| Cpd043 | N-(2-(5-chloro-1H-indol-3-yl)ethyl)-2'-cyanobiphenyl-3-carboxamide | 169 |
| Cpd044 | N-(2-(5-chloro-1H-indol-3-yl)ethyl)-2'-cyanobiphenyl-4-carboxamide | 75 |
| Cpd045 | N-(2-(5-chloro-1H-indol-3-yl)ethyl)-3-(pyridin-4-yl)benzamide | 327 |
| Cpd046 | N-(2-(5-chloro-1H-indol-3-yl)ethyl)-4-(pyridin-4-yl)benzamide | 269 |
| Cpd047 | N-(2-(5-chloro-1H-indol-3-yl)ethyl)-3'-fluorobiphenyl-3-carboxamide | 408 |
| Cpd048 | N-(2-(5-chloro-1H-indol-3-yl)ethyl)-3'-cyanobiphenyl-2-carboxamide | 232 |
| Cpd049 | N-(2-(5-chloro-1H-indol-3-yl)ethyl)-3'-cyanobiphenyl-3-carboxamide | 61 |
| Cpd050 | N-(2-(5-chloro-1H-indol-3-yl)ethyl)-3'-cyanobiphenyl-4-carboxamide | 24 |
| Cpd051 | N-(2-(5-chloro-1H-indol-3-yl)ethyl)-4'-cyanobiphenyl-2-carboxamide | 325 |
| Cpd052 | N-(2-(5-chloro-1H-indol-3-yl)ethyl)-4'-cyanobiphenyl-3-carboxamide | 112 |
| Cpd053 | N-(2-(5-chloro-1H-indol-3-yl)ethyl)-4'-cyanobiphenyl-4-carboxamide | 85 |
| Cpd054 | 2'-chloro-N-(2-(5-chloro-1H-indol-3-yl)ethyl)biphenyl-2-carboxamide | 170 |
| Cpd055 | 2'-chloro-N-(2-(5-chloro-1H-indol-3-yl)ethyl)biphenyl-3-carboxamide | 158 |
| Cpd057 | 3'-chloro-N-(2-(5-chloro-1H-indol-3-yl)ethyl)biphenyl-2-carboxamide | 159 |
| Cpd058 | 3'-chloro-N-(2-(5-chloro-1H-indol-3-yl)ethyl)biphenyl-3-carboxamide | 186 |
| Cpd059 | 3'-chloro-N-(2-(5-chloro-1H-indol-3-yl)ethyl)biphenyl-4-carboxamide | 130 |

TABLE 2-continued

| CODE | NAME | EC$_{50}$ (nM) |
|---|---|---|
| Cpd060 | 4'-chloro-N-(2-(5-chloro-1H-indol-3-yl)ethyl)biphenyl-3-carboxamide | 159 |
| Cpd061 | 4'-chloro-N-(2-(5-chloro-1H-indol-3-yl)ethyl)biphenyl-4-carboxamide | 111 |
| Cpd063 | 4'-chloro-N-(2-(5-chloro-1H-indol-3-yl)ethyl)biphenyl-2-carboxamide | 154 |
| Cpd064 | N-(2-(5-chloro-1H-indol-3-yl)ethyl)-3'-(trifluoromethyl)biphenyl-2-carboxamide | 418 |
| Cpd065 | N-(2-(5-chloro-1H-indol-3-yl)ethyl)-2'-(trifluoromethyl)biphenyl-3-carboxamide | 89 |
| Cpd066 | N-(2-(5-chloro-1H-indol-3-yl)ethyl)-3'-(trifluoromethyl)biphenyl-4-carboxamide | 92 |
| Cpd068 | N-(2-(5-chloro-1H-indol-3-yl)ethyl)-4'-(trifluoromethyl)biphenyl-3-carboxamide | 367 |
| Cpd070 | N-(2-(5-chloro-1H-indol-3-yl)ethyl)-2',6'-dimethylbiphenyl-3-carboxamide | 606 |
| Cpd071 | N-(2-(5-chloro-1H-indol-3-yl)ethyl)-3',4'-dimethylbiphenyl-2-carboxamide | 546 |
| Cpd074 | N-(2-(5-chloro-1H-indol-3-yl)ethyl)-4'-(trifluoromethyl)biphenyl-4-carboxamide | 200 |
| Cpd075 | N-(2-(5-chloro-1H-indol-3-yl)ethyl)-6-phenylpyridazine-3-carboxamide | 81 |

The invention claimed is:

1. A compound of formula (A1) or a stereoisomer, enantiomer or tautomer thereof,

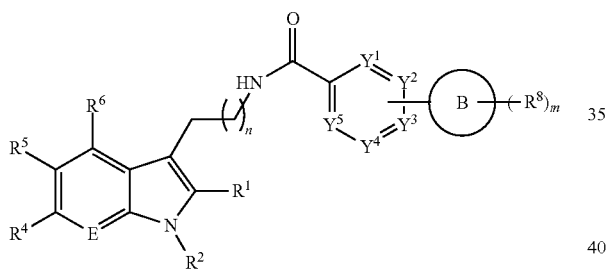

(A1)

wherein,

E is independently selected from CR$^3$; and N;

each R$^1$, R$^3$, R$^4$ and R$^6$ is independently selected from hydrogen; halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene, includes no heteroatom or one or more heteroatoms in the alkyl(ene), alkenyl(ene) or alkynyl(ene) moiety, the heteroatoms being selected from the atoms O, S and N;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene is unsubstituted or substituted with one or more Z;

and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or S(O)$_2$;

R$^2$ is selected from hydrogen; alkyl; alkenyl; and alkynyl;

R$^5$ is independently selected from halogen; —OH; —OR$^{10}$; —SH; —Se; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; —C(O)R$^{11}$; alkyl; alkenyl; alkynyl; aryl; heterocycle; arylalkylene; arylalkenylene; arylalkynylene; heterocycle-alkylene; heterocycle-alkenylene; and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene, includes no heteroatom or one or more heteroatoms in the alkyl(ene), alkenyl(ene) or alkynyl(ene) moiety, the heteroatoms being selected from the atoms O, S and N;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene is unsubstituted or substituted with one or more Z;

and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C=O, C=S, N=O, N=S, S=O or S(O)$_2$;

n is selected from 0; 1; and 2;

each of Y$^1$, Y$^2$, Y$^3$, Y$^4$ and Y$^5$ is independently selected from CZ$^1$; N; NR$^{101}$; and CO; wherein at least two of Y$^1$, Y$^2$, Y$^3$, Y$^4$ and Y$^5$ are selected from CZ$^1$;

B represents a cyclic structure selected from cycloalkyl; cycloalkenyl; cycloalkynyl; aryl; and heterocycle;

m is selected from 0; 1; 2; 3; 4 and 5;

R$^8$ is independently selected from hydrogen; halogen; alkyl; alkenyl; alkynyl; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{10}$S(O)$_2$R$^{20}$; —NR$^{20}$C(O)NR$^{22}$R$^{23}$; —NR$^{22}$R$^{23}$; -cyano; —COOR$^{20}$; —C(O)NR$^{22}$R$^{23}$; and —C(O)R$^{21}$;

wherein the alkyl, alkenyl and alkynyl includes no heteroatom or one or more heteroatoms, the heteroatoms being selected from the atoms O, S and N;

wherein the alkyl, alkenyl and alkynyl is unsubstituted or substituted with one or more Z$^2$;

and wherein a carbon atom or heteroatom of the alkyl, alkenyl and alkynyl, is unoxidized or oxidized to form a C=O, C=S, N=O, N=S, S=O or S(O)$_2$;

each Z is independently selected from halogen; —OH; —OR$^{10}$; —SH; —SR$^{10}$; —S(O)R$^{11}$; —S(O)$_2$R$^{11}$; —SO$_2$NR$^{12}$R$^{13}$; trifluoromethyl; trifluoromethoxy; nitro; —NHC(O)R$^{10}$; —NHS(O)$_2$R$^{10}$; —NHC(O)NR$^{12}$R$^{13}$; —NR$^{10}$C(O)R$^{10}$; —NR$^{10}$S(O)$_2$R$^{10}$; —NR$^{10}$C(O)NR$^{12}$R$^{13}$; —NR$^{12}$R$^{13}$; -cyano; —COOH; —COOR$^{10}$; —C(O)NR$^{12}$R$^{13}$; and —C(O)R$^{11}$;

each Z$^1$ is independently selected from hydrogen; alkyl; and Z$^2$;

each $Z^2$ is independently selected from halogen; —OH; —OR$^{20}$; —SH; —SR$^{20}$; —S(O)R$^{21}$; —S(O)$_2$R$^{21}$; —SO$_2$NR$^{22}$R$^{23}$; trifluoromethyl; trifluoromethoxy; nitro; —NHC(O)R$^{20}$; —NHS(O)$_2$R$^{20}$; —NHC(O)NR$^{22}$R$^{23}$; —NR$^{20}$C(O)R$^{20}$; —NR$^{20}$S(O)$_2$R$^{20}$; —NR$^{20}$C(O)NR$^{22}$R$^{23}$; —NR$^{22}$R$^{23}$; -cyano; —COOH; —COOR$^{20}$; —C(O)NR$^{22}$R$^{23}$; and —C(O)R$^{21}$;

each $R^{10}$ is independently selected from alkyl; alkenyl; alkynyl; aryl; heterocycle; arylalkylene; arylalkenylene; arylalkynylene; heterocycle-alkylene; heterocycle-alkenylene and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;

and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C═O, C═S, N═O, N═S, S═O or S(O)$_2$;

each $R^{101}$ is independently selected from hydrogen and $R^{10}$;

each $R^{11}$ is independently selected from hydroxyl; alkyl; alkenyl; alkynyl; aryl; heterocycle; arylalkylene; arylalkenylene; arylalkynylene; heterocycle-alkylene; heterocycle-alkenylene and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;

and wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C═O, C═S, N═O, N═S, S═O or S(O)$_2$;

each $R^{12}$ and $R^{13}$ is independently selected from hydrogen; alkyl; alkenyl; alkynyl; aryl; heterocycle; arylalkylene; arylalkenylene; arylalkynylene; heterocycle-alkylene; heterocycle-alkenylene and heterocycle-alkynylene;

wherein the alkyl, alkenyl, alkynyl, aryl, heterocycle, arylalkylene, arylalkenylene, arylalkynylene, heterocycle-alkylene, heterocycle-alkenylene or heterocycle-alkynylene includes no heteroatom or one or more heteroatoms in the alkyl(ene), alkenyl(ene) or alkynyl(ene) moiety, the heteroatom selected from O, S and N;

wherein a carbon atom or heteroatom of the alkyl, alkenyl, alkynyl, aryl, heterocycle, arylalkylene, arylalkenylene, arylalkynylene, heterocycle-alkylene, heterocycle-alkenylene or heterocycle-alkynylene, is unoxidized or oxidized to form a C═O, C═S, N═O, N═S, S═O or S(O)$_2$;

and wherein $R^{12}$ and $R^{13}$ can be taken together in order to form a (4-, 5-, 6-, or 7-membered) heterocycle which is unsubstituted or substituted;

each $R^{20}$ is independently selected from alkyl; alkenyl; and alkynyl;

wherein the alkyl, alkenyl, alkynyl includes no heteroatom or one or more heteroatoms in the alkyl, alkenyl or alkynyl moiety, the heteroatom selected from O, S and N;

and wherein a carbon atom or heteroatom of the alkyl, alkenyl, alkynyl is unoxidized or oxidized to form a C═O, C═S, N═O, N═S, S═O or S(O)$_2$;

each $R^{21}$ is independently selected from hydroxyl; alkyl; alkenyl; and alkynyl;

wherein the alkyl, alkenyl or alkynyl includes no heteroatom or one or more heteroatoms in the alkyl, alkenyl or alkynyl moiety, the heteroatom selected from O, S and N;

and wherein a carbon atom or heteroatom of the alkyl, alkenyl or alkynyl is unoxidized or oxidized to form a C═O, C═S, N═O, N═S, S═O or S(O)$_2$;

each $R^{22}$ and $R^{23}$ is independently selected from hydrogen; alkyl; alkenyl; and alkynyl;

wherein the alkyl, alkenyl or alkynyl includes no heteroatom or one or more heteroatoms in the alkyl, alkenyl or alkynyl moiety, the heteroatom selected from O, S and N;

wherein a carbon atom or heteroatom of the alkyl, alkenyl or alkynyl is unoxidized or oxidized to form a C═O, C═S, N═O, N═S, S═O or S(O)$_2$;

and wherein $R^{22}$ and $R^{23}$ can be taken together in order to form a (4-, 5-, 6-, or 7-membered) non-aromatic heterocycle which is unsubstituted or substituted;

and a solvate, hydrate, salt, pharmaceutically acceptable salt, or prodrug thereof.

2. The compound of claim 1, having structural formula (A2) or (A3)

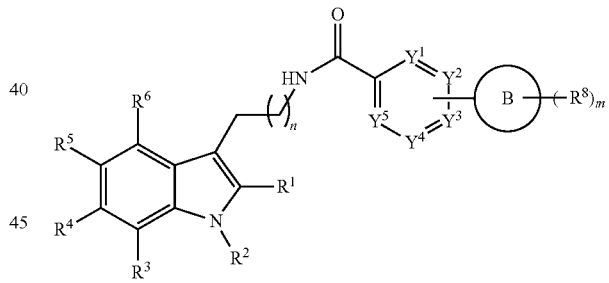

(A2)

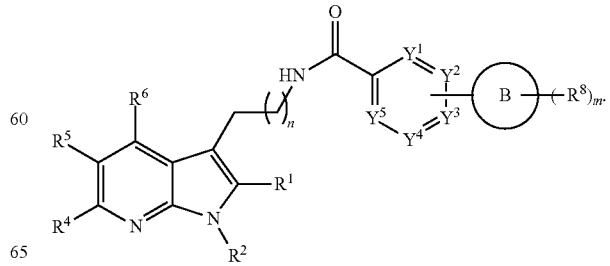

(A3)

3. The compound of claim 1, having structural formula (B1), (B2) or (B3), (B1)
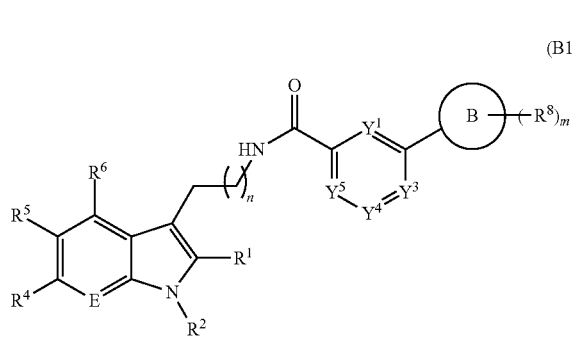

(B2)
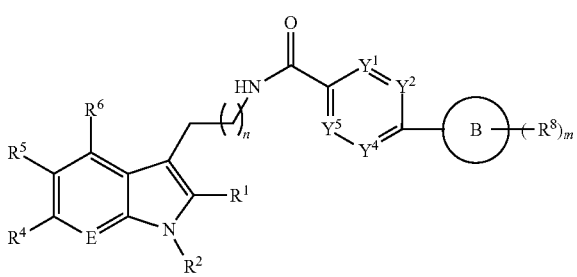

(B3)
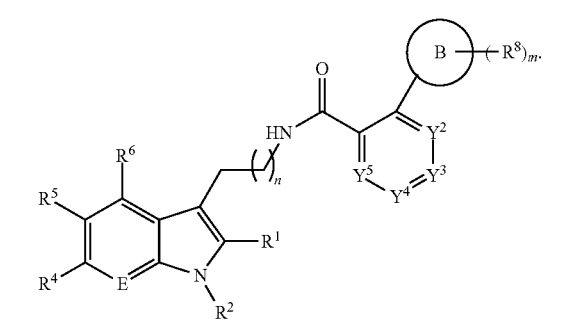

4. The compound of claim 1, having structural formula (C1), (C2), or (C3), (C1)
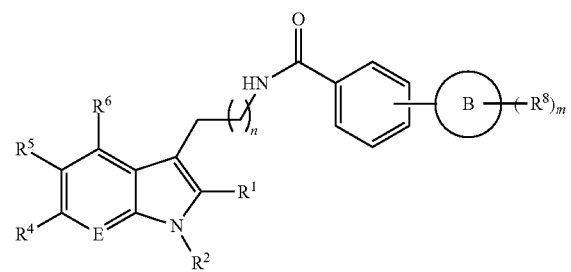

(C2)
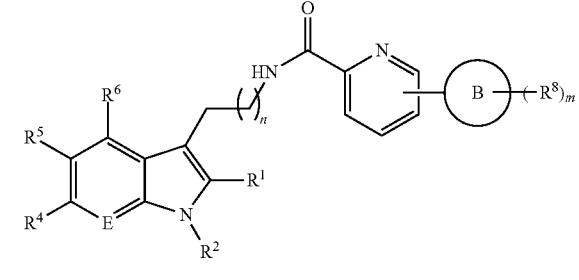

(C3)
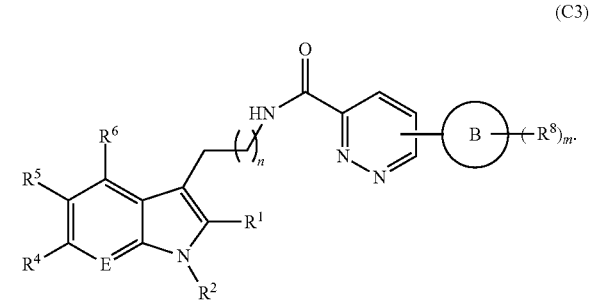

5. The compound of claim 1, wherein B is aryl and $R^8$ is selected from hydrogen, halogen, —OH, cyano, $C_{1-6}$alkyl, $C_{1-6}$alkoxy, $C_{1-6}$alkoxycarbonyl, trifluoromethyl; trifluoromethoxy.

6. The compound of claim 1, wherein each of $R^1$, $R^2$, $R^3$, $R^4$ and $R^6$ are hydrogen.

7. The compound of claim 1, having structural formula (I1), (I2), (I3), or (I4)

(I1)
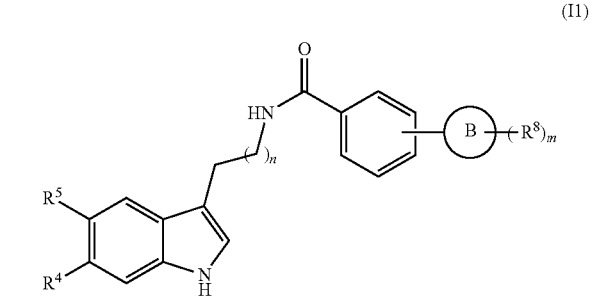

(I2)
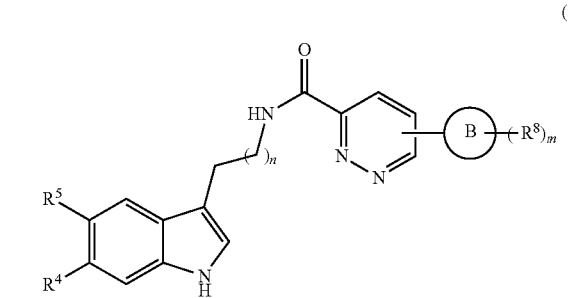

-continued (I3)
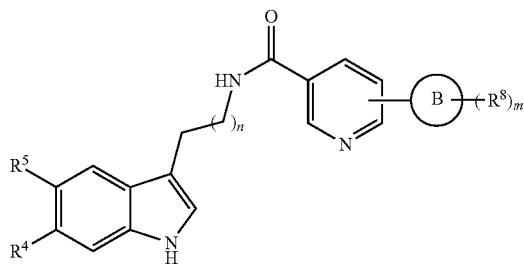

(I4)
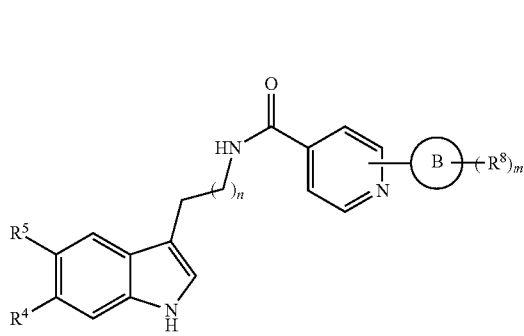

wherein
  R⁴ is selected from hydrogen and halogen;
  R⁵ is selected from halogen; —OH; —OR¹⁰; trifluoromethyl; trifluoromethoxy; cyano; —C(O)R¹¹; and C$_{1-6}$alkyl;
  n is selected from 0; 1; and 2;
  B represents a cyclic structure selected from C$_{3-8}$cycloalkyl; C$_{6-10}$aryl; and heterocycle;
  m is selected from 0; 1; and 2;
  each R⁸ is independently selected from halogen; C$_{1-6}$alkyl; —OH; C$_{1-6}$alkoxy; —COOR²⁰; trifluoromethyl; trifluoromethoxy; and cyano;
  each R¹⁰ is C$_{1-6}$alkyl;
  each R¹¹ is C$_{1-6}$alkyl;
  each R²⁰ is C$_{1-6}$alkyl;
  wherein when B is ortho-phenyl in formula (I1), then m is 1 or 2;
and isomers, solvates, hydrates, or salts thereof.

8. The compound of claim 1, having structural formula (J1), (J2), (J3), or (J4)

(J1)
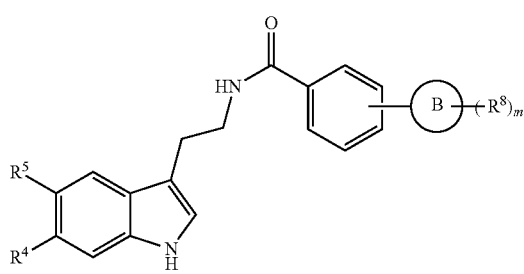

(J2)
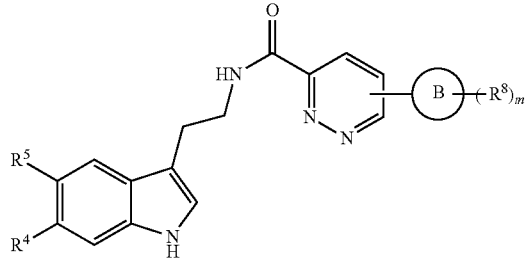

(J3)
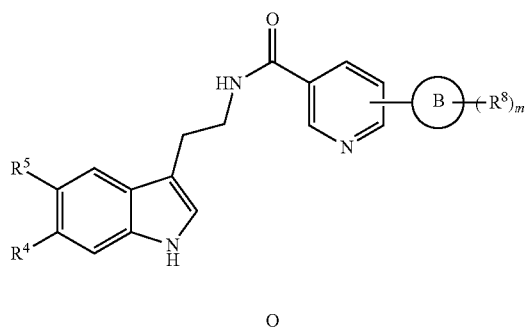

(J4)

wherein
  R⁴ is selected from hydrogen and halogen;
  R⁵ is selected from halogen; —OH; —OR¹⁰; trifluoromethyl; trifluoromethoxy; cyano; —C(O)R¹¹; and C$_{1-6}$alkyl;
  B represents a cyclic structure selected from C$_{3-8}$cycloalkyl; C$_{6-10}$aryl; and heterocycle;
  m is selected from 0; 1; and 2;
  each R⁸ is independently selected from halogen; C$_{1-6}$alkyl; —OH; C$_{1-6}$alkoxy; —COOR²⁰; trifluoromethyl; trifluoromethoxy; and cyano;
  each R¹⁰ is C$_{1-6}$alkyl;
  each R¹¹ is C$_{1-6}$alkyl;
  each R²⁰ is C$_{1-6}$alkyl;
  wherein where B is ortho-phenyl in formula (J1), then m is 1 or 2;
and isomers, solvates, hydrates, or salts thereof.

9. A pharmaceutical composition comprising one or more pharmaceutically acceptable excipients and a therapeutically effective amount of the compound of claim 1.

10. A method for the preparation of the compound of claim 1, and isomers, solvates, hydrates, salts, or prodrugs thereof, the method comprising:
  reacting a substituted or unsubstituted (1H-indol-3-yl)methanamine, 2-(1H-indol-3-yl)ethanamine or 3-(1H-indol-3-yl)propan-1-amine with a correctly substituted six membered ring derivative bearing an acid halide function in a polar aprotic solvent in the presence of a strong base at a temperature between −10° C. to 100° C.;

reacting a substituted or unsubstituted (1H-indol-3-yl)methanamine, 2-(1H-indol-3-yl)ethanamine or 3-(1H-indol-3-yl)propan-1-amine with a correctly substituted six membered ring derivative bearing one carboxylic acid function in a polar aprotic solvent in the presence of a peptide bond formation coupling agent at a temperature between 0° C. to 50° C.

11. The method according to claim 10, further comprising:
wherein the six membered ring bears a leaving group (LG), reacting the compound with suitable nucleophiles and in the presence of a strong base or reacting the compound with derivatives in the presence of a palladium or copper catalyst.

12. The method according to claim 11, wherein the suitable nucleophiles are amines or alcohols.

13. The method according to claim 12, wherein the derivatives are selected from boronic acids, stannane, and organozinc derivatives.

* * * * *